United States Patent
Yu et al.

(10) Patent No.: US 12,188,046 B2
(45) Date of Patent: Jan. 7, 2025

(54) CULTURE MEDIUM, COATING MATRIX AND METHOD FOR EXPANDING MIDBRAIN DOPAMINERGIC PROGENITOR CELLS

(71) Applicant: NUWACELL BIOTECHNOLOGIES CO., LTD., Anhui (CN)

(72) Inventors: Junying Yu, Anhui (CN); Luyan Jiao, Anhui (CN); Yongqiang Zhao, Anhui (CN); Ying Zhang, Anhui (CN)

(73) Assignee: NUWACELL BIOTECHNOLOGIES CO., LTD., Anhui (CN)

( * ) Notice: Subject to any disclaimer, the term of this patent is extended or adjusted under 35 U.S.C. 154(b) by 0 days.

(21) Appl. No.: 18/119,682

(22) Filed: Mar. 9, 2023

(65) Prior Publication Data

US 2024/0200027 A1  Jun. 20, 2024

Related U.S. Application Data

(63) Continuation of application No. PCT/CN2022/136178, filed on Dec. 2, 2022.

(51) Int. Cl.
*C12N 5/0793* (2010.01)

(52) U.S. Cl.
CPC ........ *C12N 5/0619* (2013.01); *C12N 2501/13* (2013.01); *C12N 2501/15* (2013.01); *C12N 2501/727* (2013.01); *C12N 2533/50* (2013.01)

(58) Field of Classification Search
CPC ................................................ C12N 2533/50
See application file for complete search history.

(56) References Cited

U.S. PATENT DOCUMENTS

| 2014/0248696 | A1 | 9/2014 | Zhang et al. |
| 2019/0367877 | A1 | 12/2019 | Kaneko et al. |
| 2020/0263139 | A1* | 8/2020 | Vodyanyk ............ C12N 5/0639 |

FOREIGN PATENT DOCUMENTS

| CN | 109880800 A | 6/2019 |
| CN | 112011510 A | 12/2020 |
| CN | 112725278 A | 4/2021 |
| CN | 107438669 B | 9/2022 |
| WO | 2019023793 A1 | 2/2019 |
| WO | 2021168171 A1 | 8/2021 |
| WO | 2022037570 A1 | 2/2022 |

OTHER PUBLICATIONS

Kirkeby, A., et al., "Generation of Regionally Specified Neural Progenitors and Functional Neurons from Human Embryonic Stem Cells under Defined Conditions", Cell Reports, Jun. 28, 2012, pp. 703-714, 1.
International Search Report and Written Opinion received in PCT/CN2022/136178 dated Aug. 21, 2023, 10 pages.
De Gouville, A,C., et al., "Inhibition of TGF-b signaling by an ALK5 inhibitor protects rats from dimethylnitrosamine-induced liver fibrosis", British Journal of Pharmacology (2005), pp. 166-177, 145.
Dontu, G., et al., "Role of Notch signaling in cell-fate determination of human mammary stem/progenitor cells", Breast Cancer Res 2004, pp. R605-R615, vol. 6, No. 6.
Drew, A.E., et al., "Comparison of 2 Cell-Based Phosphoprotein Assays to Support Screening and Development of an ALK Inhibitor", Journal of Biomolecular Screening, 2011, pp. 164-173, 16(2).
Fedele, S., et al., "Expansion of human midbrain floor plate progenitors from induced pluripotent stem cells increases dopaminergic neuron differentiation potential", Scientific Reports, 2017, pp. 1-11, 7:6036.
Hsieh, J., J.-D., et al., "Truncated Mammalian Notch1 Activates CBF1/RBPJk-Repressed Genes by a Mechanism Resembling That of Epstein-Barr Virus EBNA2", Molecular and Cellular Biology, Mar. 1996, pp. 952-959 vol. 16, No. 3.
Kirikoshi, H., et al., "WNT10A and WNT6, Clustered in Human Chromosome 2q35 Region with Head-to-Tail Manner, Are Strongly Coexpressed in SW480 Cells", Biochemical and Biophysical Research Communications, (2001), pp. 798-805, 283.
Korinek, , "Constitutive Transcriptional Activation by a b-Catenin-Tcf Complex in APC2/2 Colon Carcinoma", Science, Mar. 21, 1997, pp. 1784-1787, vol. 275.
Leost, M., et al., "Paullones are potent inhibitors of glycogen synthase kinase-3b and cyclin-dependent kinase 5/p25", Eur. J. Biochem. (2000), pp. 5983-5994, 267.
Liao, X., et al., "Glycogen Synthase Kinase-3B Activity Is Required for Androgen-Stimulated Gene Expression in Prostate Cancer", Endocrinology, Jun. 2004, pp. 2941-2949, 145(6).
Liu, J., et al., "A Small-Molecule Agonist of the Wnt Signaling Pathway", Angew. Chem. Int. Ed. 2005, pp. 1987-1990, 44.
Meijer, L., et al., "GSK-3-Selective Inhibitors Derived from Tyrian Purple Indirubins", Chemistry & Biology, Dec. 2003, pp. 1255-1266, vol. 10.
Meijer, L., et al., "Pharmacological inhibitors of glycogen synthase kinase 3", TRENDS in Pharmacological Sciences, Sep. 2004, pp. 473-480, vol. 25. No. 9.
Planutis, K., et al., "Regulation of norrin receptor frizzled-4 by Wnt2 in colon-derived cells", BMC Cell Biology 2007, pp. 1-10, 8:12.

* cited by examiner

*Primary Examiner* — Kara D Johnson
(74) *Attorney, Agent, or Firm* — Scully, Scott, Murphy & Presser, P.C.

(57) ABSTRACT

The present disclosure described herein provides, inter alia, an expansion method for expanding mDAPs and a culture medium and a coating matrix combination used in the expansion method, as well as a maturation method for maturing mDAPs and a culture medium used in the maturation method. The present disclosure also provides a substantially homogeneous population of mDAPs and a substantially homogeneous population of mDANs.

21 Claims, 25 Drawing Sheets

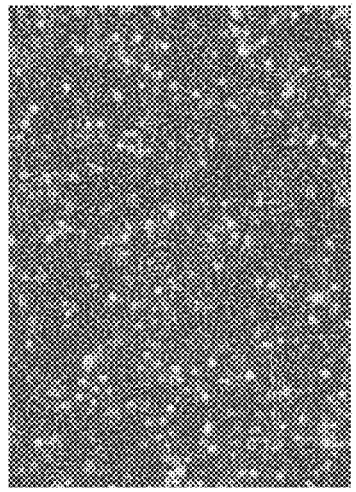
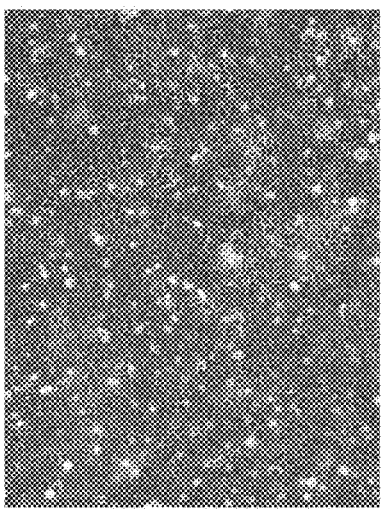

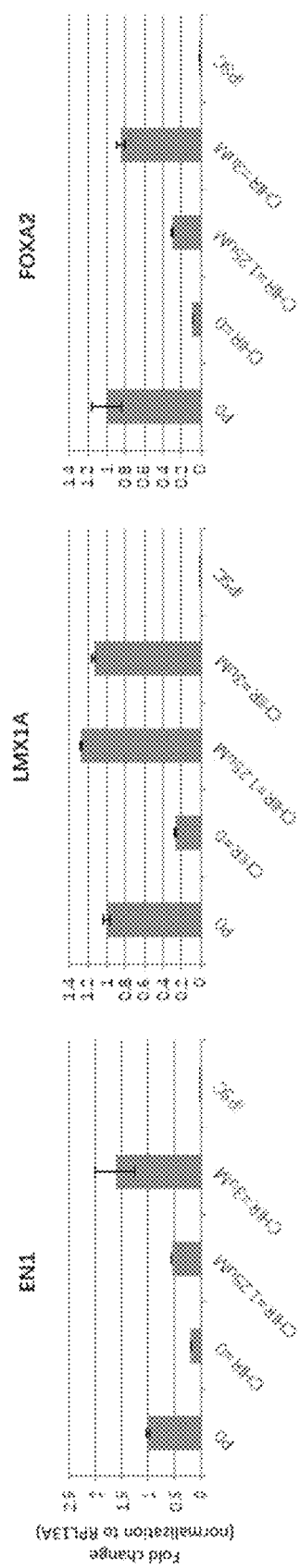
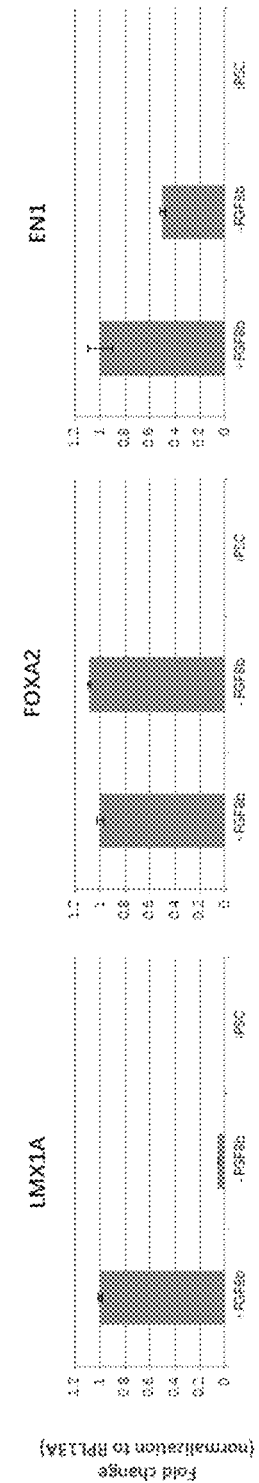
FIG. 1C
FIG. 1D

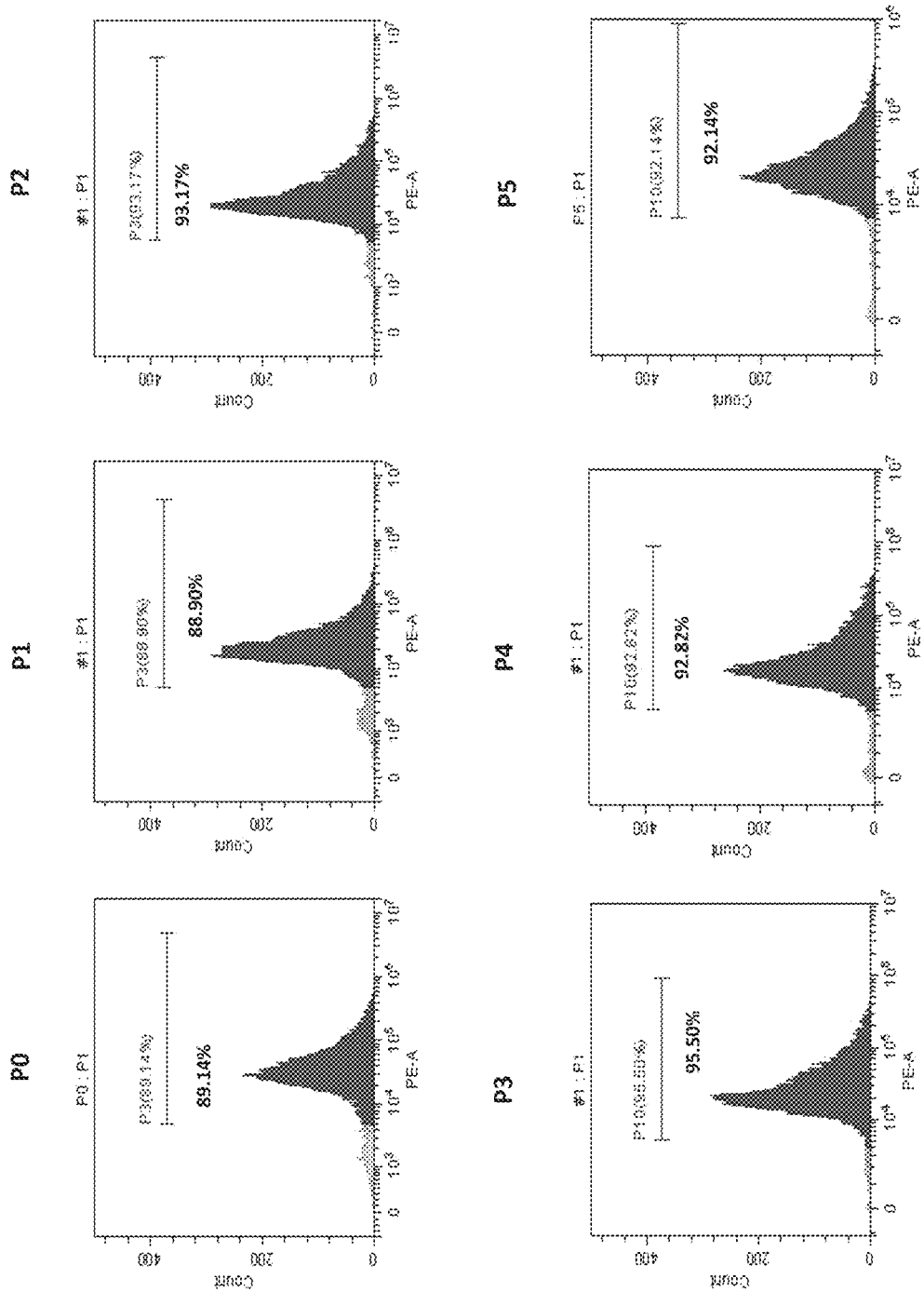

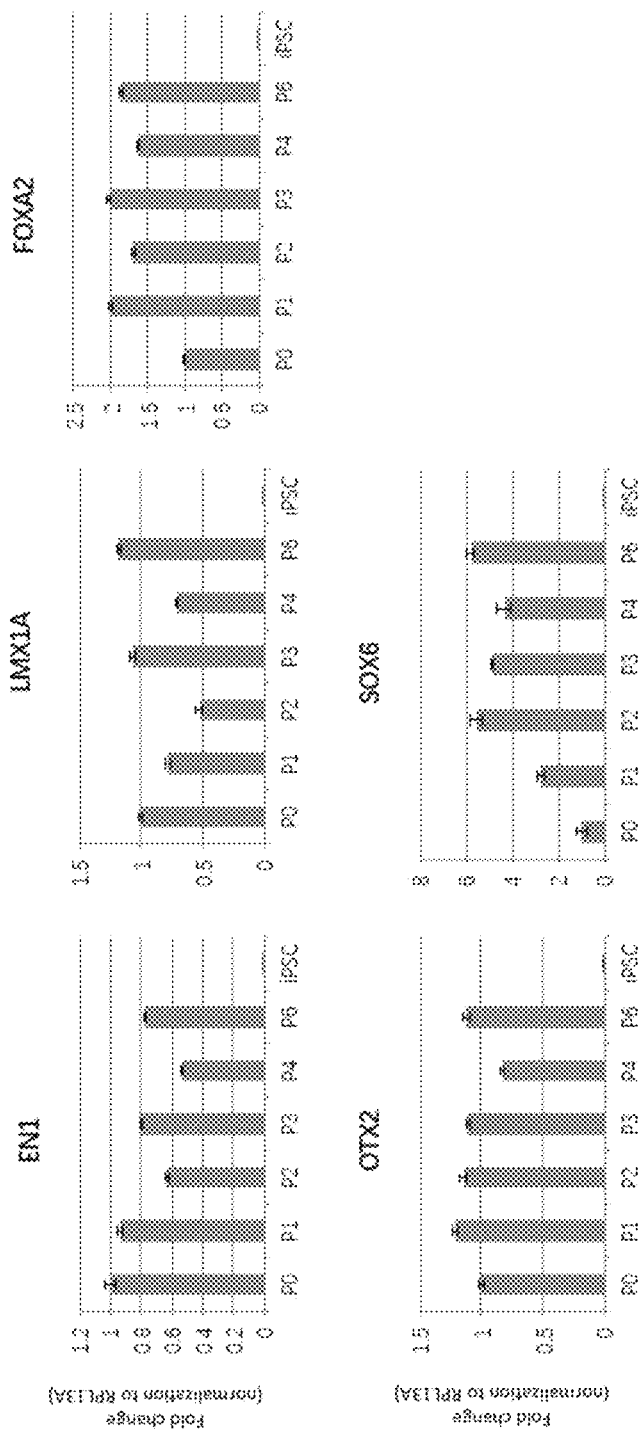

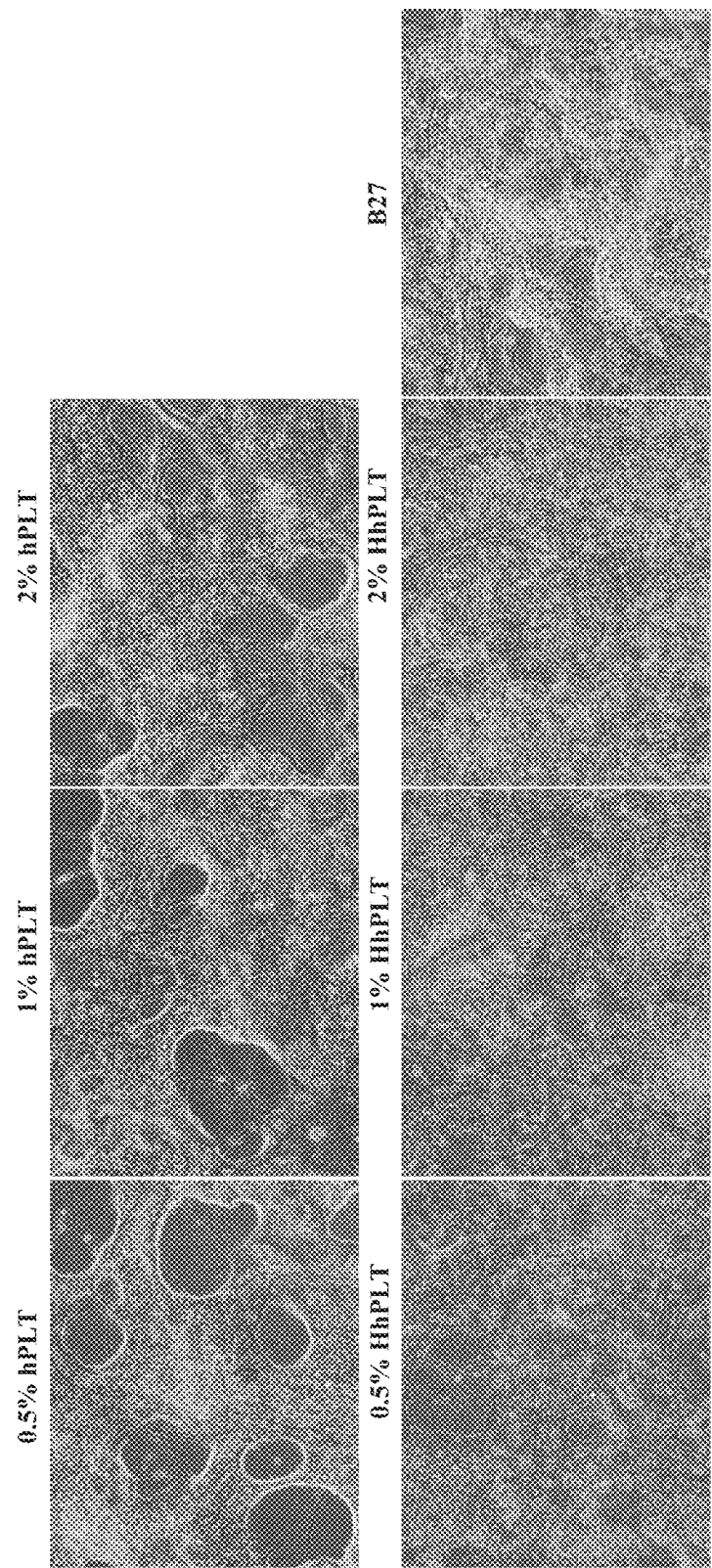

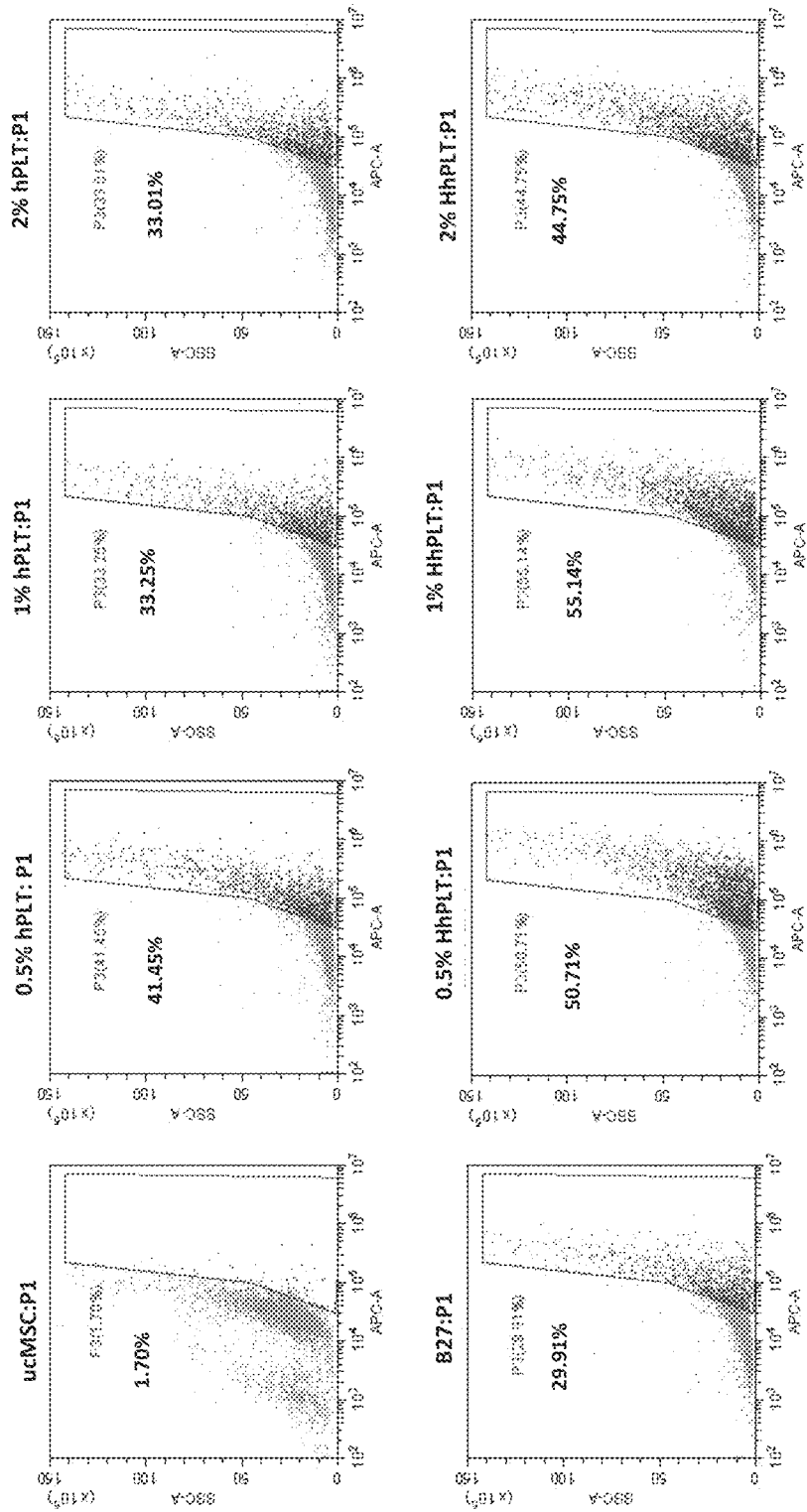

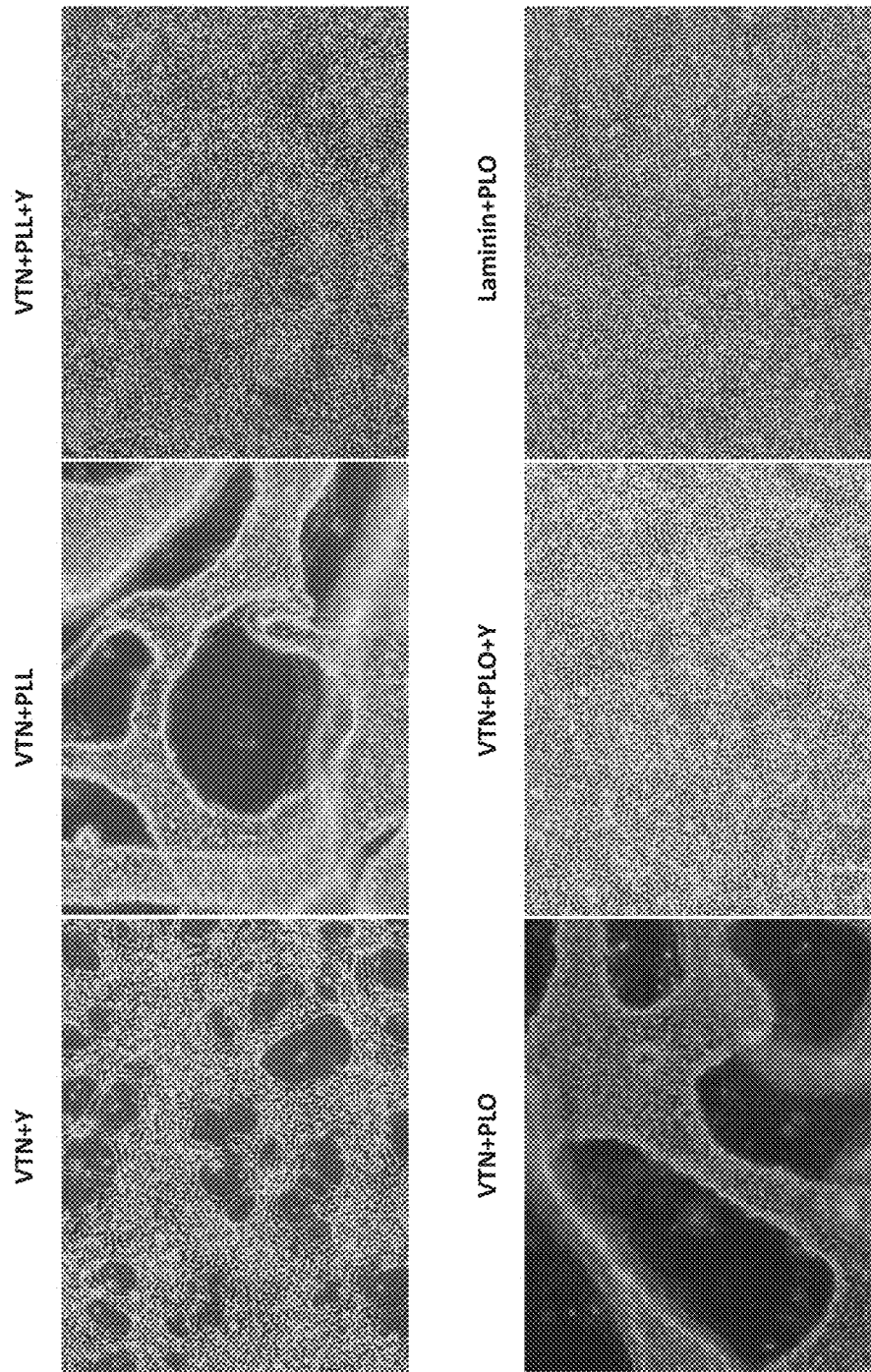

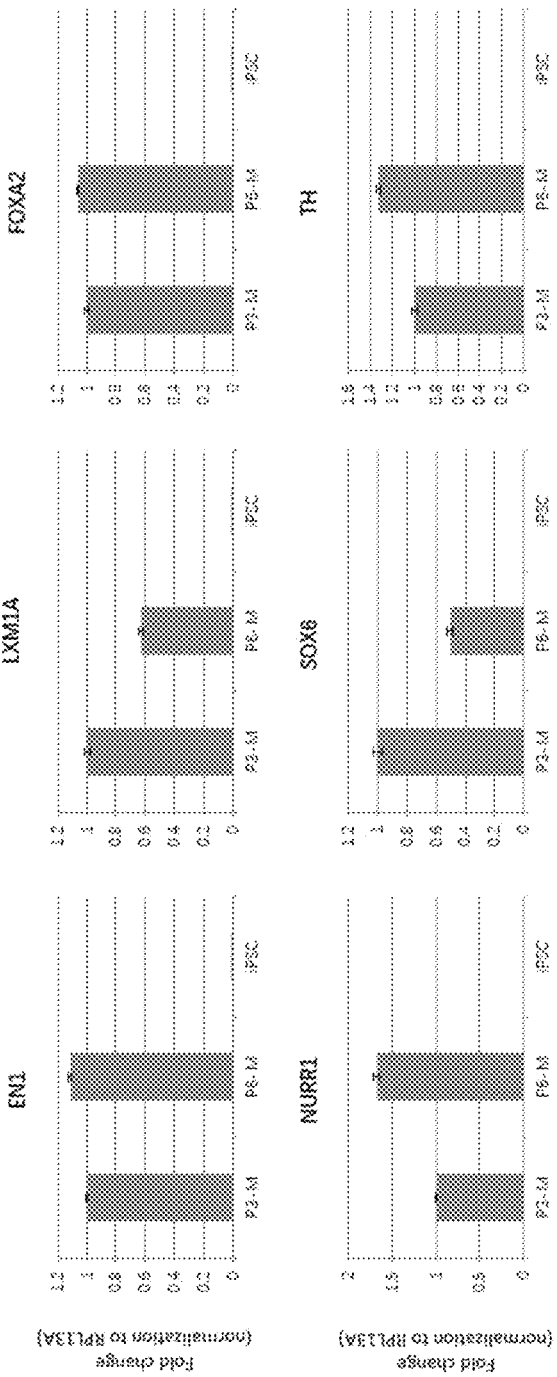

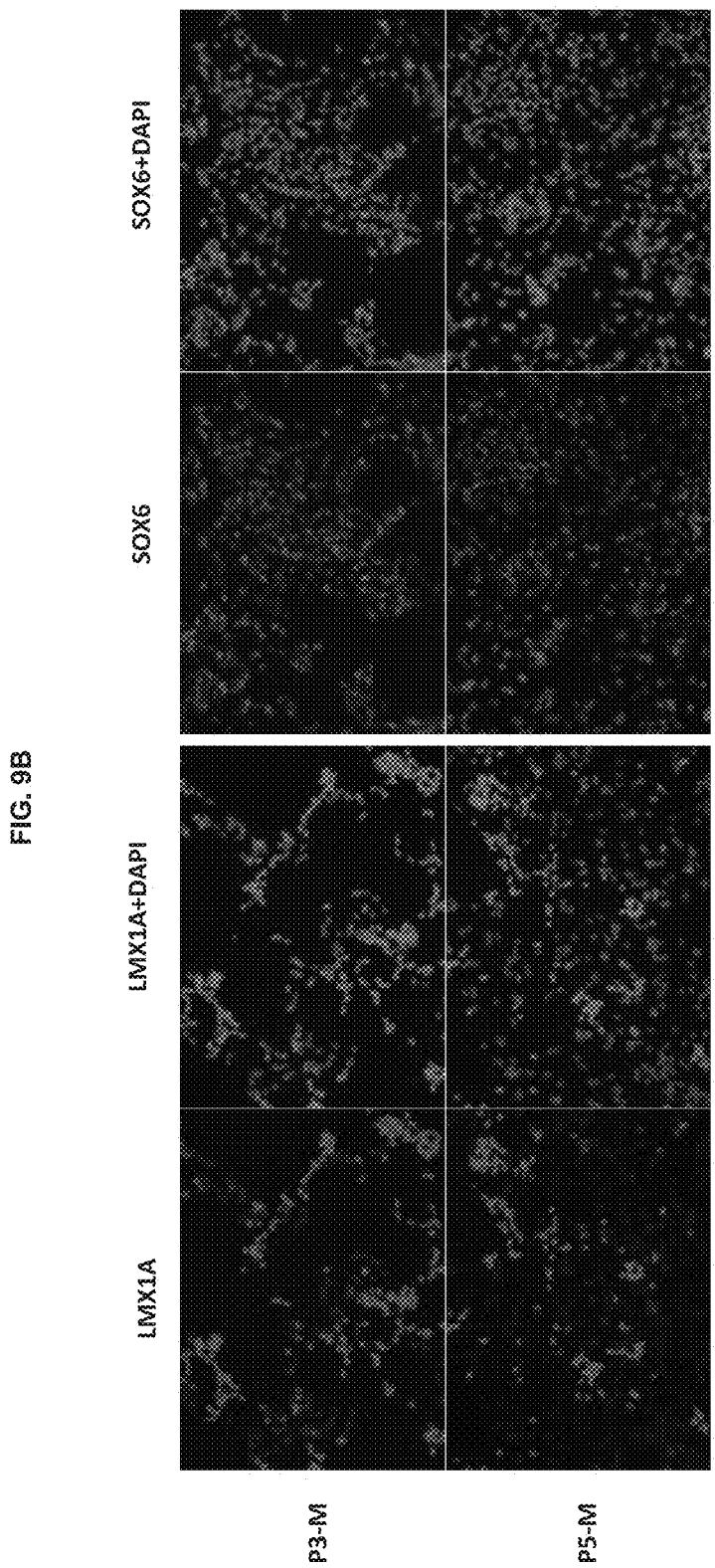

CULTURE MEDIUM, COATING MATRIX AND METHOD FOR EXPANDING MIDBRAIN DOPAMINERGIC PROGENITOR CELLS

CROSS REFERENCE TO RELATED APPLICATIONS

This patent application is a continuation of and claims the benefit of international patent application No. PCT/CN2022/136178, filed on Dec. 2, 2022, the entire content of which is incorporated by reference herein.

TECHNICAL FIELD

The present disclosure generally relates to the field of stem cell technology, in particular to culture media, coating matrices and methods for expanding and maturing midbrain Dopaminergic Progenitor cells (mDAPs).

BACKGROUND

Parkinson's disease (PD) is the second most common neurodegenerative disorder. A hallmark of the disease is the selective loss of dopaminergic neurons (DA neurons) of the substantia nigra of the midbrain. Although recent developments in medical science have greatly advanced the general understanding of the pathogenesis of PD, unfortunately, there are no cures for this devastating disease at present. The main treatment for PD patients is DA analogues and receptor agonists to counteract the reductions in DA.

Thus, there remains a need to further advance the study for the mechanism of PD, its disease progression, and effective clinical intervention approaches to effectively treat PD, and one pre-requisite for such studies is the availability of midbrain Dopaminergic Progenitor cells.

Pluripotent stem cells comprise human pluripotent stem cells (hPSCs), including human embryonic stem cells (hESCs) and human induced pluripotent stem cells (hiPSCs). These pluripotent stem cells can be expanded in vitro and retain their capacity to differentiate into any cell types of the three germ layers, including neuronal cells and tissues. Thus these pluripotent stem cells are invaluable to study developmental processes and disease mechanisms, especially in the brain. In particular, hiPSCs represent an unlimited source of cells for utilities such as mechanism studies, drug screening assays, and eventually cell replacement therapy for the treatment of neurological disorders, such as PD. Numerous protocols have been developed to generate human DA neurons in vitro from hPSCs.

These protocols typically rely on the directed differentiation of pluripotent stem cells into imDAPs using small molecules and growth factors, and the expansion and maturation of imDAPs. They are often laborious, long, and highly variable between batches, resulting in heterogeneous population with relatively low numbers of midbrain DA neurons. However, in clinical and therapeutical applications, a homogeneous and robust populations of cells are strongly desired.

Thus, there remains a need to provide improved reagents, compositions and methods useful for expanding and/or maturing mDAPs.

SUMMARY

In a first aspect, the present disclosure provides a culture medium that is capable of promoting the expansion of midbrain Dopaminergic Progenitor cells (mDAPs), said culture medium comprising: (a) a basal medium; (b) a neural growth supplement; (c) a WNT signaling pathway activator; (d) a Rho Kinase (ROCK) inhibitor; and (e) a Transforming Growth Factor β (TGF-β) inhibitor.

In a second aspect, the present disclosure provides a coating matrix combination that is capable of promoting the expansion of midbrain Dopaminergic Progenitor cells (mDAPs), said coating matrix combination comprising: (a) a first coating matrix that can support cell adhesion for the mDAPs; and, (b) a second coating matrix that can improve the expression of the mDAP-specific markers during the expansion and passaging of the mDAPs, wherein the second coating matrix comprises a Notch agonist.

In a third aspect, the present disclosure provides a method for expanding midbrain Dopaminergic Progenitor cells (mDAPs), comprising contacting the mDAPs with an expansion medium on a culture surface coated with the coating matrix combination of the $2^{nd}$ aspect of the present disclosure described herein.

In a fourth aspect, the present disclosure provides a culture medium that is capable of promoting maturation of mDAPs (midbrain Dopaminergic Progenitor cells), said culture medium comprising: (a) a neural basal medium; (b) a human Platelet Lysate (hPLT); (c) a Transforming Growth Factor β (TGF-β); (d) a γ-secretase inhibitor; and (e) a cAMP-based compound or its cyclase activator.

In a fifth aspect, the present disclosure provides a method for promoting the maturation of midbrain Dopaminergic Progenitor cells (mDAPs), comprising contacting the mDAPs with a ROCK inhibitor-containing maturation medium on a culture surface coated with a coating matrix combination comprising: (a) a first coating matrix that can support cell adhesion for the mDAPs, wherein the first coating matrix is not laminin; and, (b) a second coating matrix that can improve the maturity for the mDAPs, wherein the second coating matrix comprises a polylysine-based compound and/or a polyornithine-based compound.

In a sixth aspect, the present disclosure provides a substantially homogeneous population of mDAPs produced by the method of the $3^{rd}$ aspect of the present disclosure described herein.

In a seventh aspect, the present disclosure provides a substantially homogeneous population of midbrain Dopaminergic neurons (mDANs) produced by the method of the $5^{th}$ aspect of the present disclosure described herein.

In an eighth aspect, the present disclosure provides a kit comprising the culture medium of the $1^{st}$ aspect of the present disclosure described herein.

In certain embodiments, the kit further comprises the coating matrix combination of the $2^{nd}$ aspect of the present disclosure described herein.

In a ninth aspect, the present disclosure provides a kit comprising the culture medium of the $4^{th}$ aspect of the present disclosure described herein.

In certain embodiments, the kit further comprises the coating matrix combination of the $5^{th}$ aspect of the present disclosure described herein.

Various objects and advantages of the reagents, compositions and methods as provided herein will become apparent from the following description taken in conjunction with the accompanying drawings wherein are set forth, by way of illustration and example, certain embodiments of the present disclosure.

BRIEF DESCRIPTION OF THE DRAWINGS

FIG. 1 shows the development and verification of the expansion medium based on the combination of LDN193189/CHIR99021/FGF8b/Blebbistatin according to the Examples 1-5 of the present disclosure, wherein FIG. 1A shows the morphologies of cells expanded in the absence of Blebbistatin (left image), in case where Blebbistatin is removed 24 hrs after plating (middle image), and in case where Blebbistatin is present throughout the culture period (right image) (Scale bar: S0 μm); FIG. 1B shows the morphologies of cells expanded without LDN193189 (left image) and with LDN193189 (right image) (Scale bar: 50 μm); FIG. 1C shows the effect of the concentration of CHIR99021 in the expansion medium on the expression of imDAP-specific markers, EN1, LMX1A, and FOXA2 (a representative marker for mDAPs); FIG. 1D shows the effect of the presence or absence of FGF8b in the expansion medium on the expression of imDAP-specific markers, EN1, LMX1A and FOXA2.

FIG. 3 shows the results of single cell RNA-Seq analysis of imDAPs according to the Example 7 of the present disclosure, wherein

FIG. 4 shows the effects of NOTCH activation and TGF-β inhibition on the expansion of imDAPs according to the Example 8 of the present disclosure, wherein

FIG. 5 shows the effects of LDN193189, FGF8b and FGF2 on the expansion of imDAPs according to the Example 9 of the present disclosure, wherein

FIG. 6 shows the effect of NOTCH activation in combination with TGF-β inhibition on the expansion of imDAPs according to the Example 10 of the present disclosure, wherein FIG. 6C shows the results of FACS analysis of FOXA2 expression in imDAPs at each passage (P0~P5) during long-term expansion; and FIG. 6D shows the results of qRT-PCR analysis of imDAP-specific markers, EN1, LMX1A, FOXA2, OTX2 and SOX6, in imDAPs at each passage (P0~P6) during long-term expansion.

FIGS. 7A-C show the effects of a human Platelet Lysate (hPLT) and a heat-treated human Platelet Lysate (HhPLT) in replacement of B27 on the maturation of imDAPs according to the Example 11 of the present disclosure, wherein FIG. 7A shows bright-field images of imDAPs cultured with different concentration of hPLT or HhPLT, or with B27 in the maturation media (Scale bar: 50 μm); FIG. 7B shows the results of FACS analysis of TH (TH (Tyrosine Hydroxylase) is a representative maturation marker for mDA neurons) expression in imDAPs cultured with different concentration of hPLT or HhPLT, or with B27 in the maturation media; and FIG. 7C shows the results of immunocytochemical analysis of TH in mDA neurons generated by maturation with 1% HhPLT or B27 (Scale bar: 50 μm).

FIGS. 7D-E show the effect of IWR1 on the maturation of imDAPs according to the Example 12 of the present disclosure, wherein FIG. 7D shows the morphologies of cells matured with or without IWR1 in the maturation medium (Scale bar: 50 μm); and FIG. 7E shows the results of qRT-PCR analysis of the expression of markers, EN1, LMX1A, FOXA2, NURR1, SOX6 and TH, in cells matured with or without IWR1 in the maturation medium.

FIGS. 8A-C shows the effects of Y27632 (Y) and PLLH (poly-L-Lysine hydrobromide) or PLOH (Poly-L-Ornithine hydrobromide) on the maturation of imDAPs according to the Example 13 of the present disclosure, wherein FIG. 8A shows bright-field images of cells matured using VTN+Y, VTN+PLLH, VTN+PLLH+Y, VTN+PLOH, VTN+PLOH+Y, or Laminin+PLOH (Scale bar: 50 μm); FIG. 8B shows the yields of cells matured using VTN+Y, VTN+PLLH+Y, VTN+PLOH+Y, or Laminin+PLOH; and FIG. 8C shows the results of qRT-PCR analysis of the expression of maturation associated markers, EN1, LMX1A, FOXA2, SOX6, NURR1, and TH, in cells following 7-day maturation.

FIG. 9 shows the differentiation capabilities of the expanded imDAPs at early and late passage, wherein FIG. 9A shows the results of RT-qPCR analysis of the expression of specific markers, EN1, LMX1A, FOXA2, NURR1, SOX6 and TH, in early-stage mDA neurons matured from expanded P3 and P6 imDAPs; FIG. 9B shows the results of immunocytochemical analysis of the expression of LMX1A and SOX6 in early-stage mDA neurons matured from expanded P3 and P5 imDAPs.

DETAILED DESCRIPTION

Figure 1E:
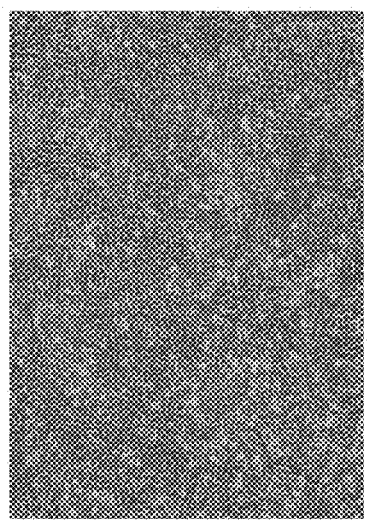
FIG. 1E shows typical morphology of expanded imDAPs at each passage (P1~P6) 4-5 days after passaging (Scale bar: 50 μm)
Figure 1E:
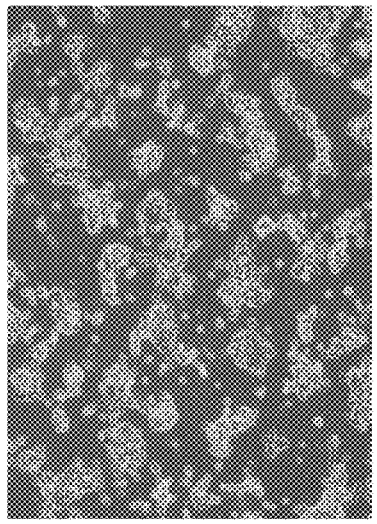
Figure 1E:
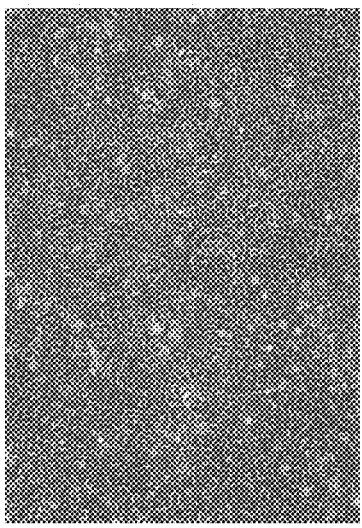
Figure 1E:
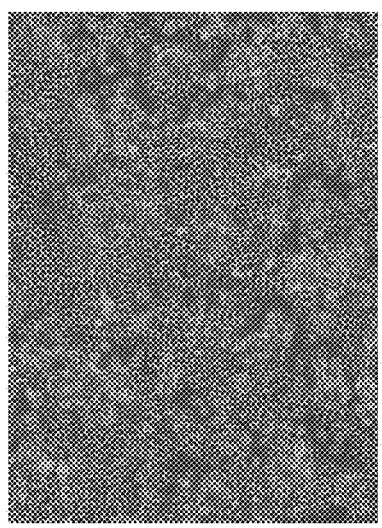
Figure 1E:
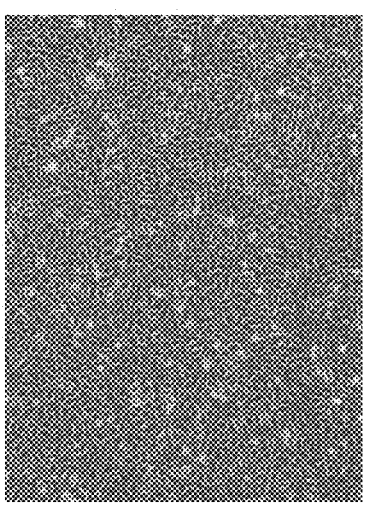
Figure 1E:
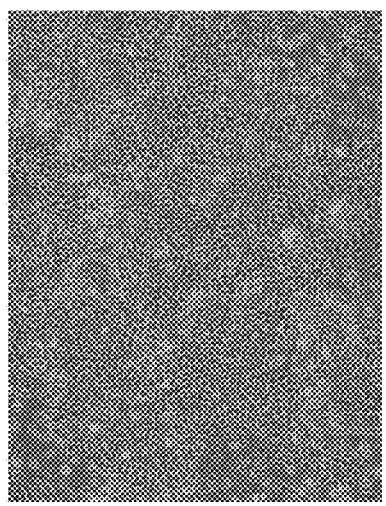

It is to be appreciated that certain aspects, modes, embodiments, variations and features of the present disclosure are described below in various levels of detail in order to provide a substantial understanding of the present technology.

Reference throughout this specification to "first", "second", "third", "fourth", "fifth", "sixth", "seventh", "eighth", or "ninth", does not mean the order or sequence of the feature, structure (e.g., medium or composition) or characteristic described in connection with the reference and can be used only for the purpose of distinction.

Reference throughout this specification to "a first aspect", "a second aspect", "a third aspect", "a fourth aspect", "a fifth aspect", "a sixth aspect", "a seventh aspect", "an eighth aspect", or "a ninth aspect", means that a particular feature, structure or characteristic described in connection with the aspect is included in at least one or more aspects of the present disclosure. Also, the particular feature(s), structure(s), characteristic(s) or embodiment(s) in one aspect may be combined with those in one or more other aspects in any suitable manner.

Reference throughout this specification to "one embodiment", "another embodiment", "a preferred embodiment(s)", "some embodiments", or "a certain embodiment(s)", means that a particular feature, structure or characteristic described in connection with the embodiment(s) is included in at least one or more embodiments of the present disclosure. Also, the particular feature(s), structure(s), or characteristic(s) in one embodiment may be combined with those in one or more other embodiments in any suitable manner.

The present disclosure illustratively described herein suitably may be practiced in the absence of any element or elements, limitation or limitations that are not specifically disclosed herein. As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of). Further, in each instance herein any of the terms "comprising", "consisting essentially of", and "consisting of", may be replaced with either of the other two terms.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

1. Culture Medium for Expanding mDAPs

In a first aspect, the present disclosure provides a culture medium (e.g., chemically defined serum-free expansion medium) that is capable of promoting the, robust expansion of midbrain Dopaminergic Progenitor cells (mDAPs), said culture medium comprising: (a) a basal medium; (b) a neural growth supplement; (c) a WNT signaling pathway activator; (d) a Rho Kinase (ROCK) inhibitor; and (e) a Transforming Growth Factor β (TGF-β) inhibitor.

According to the first aspect, due to the inclusion of the TGF-β inhibitor and in particular the ROCK inhibitor and the TGF-β inhibitor, the expansion medium of the present disclosure can improve the expansion efficiency and expression of mDAP-specific markers during the expansion and passaging of the mDAPs.

The expansion medium of the present disclosure may be contacted with the mDAPs on a cell culture surface. The cell culture surface may be coated with any common expansion coating matrix in the art or any other suitable expansion coating matrix. Examples of common coating matrix comprise vitronectin (VTN), Matrigel, Fibronectin, Gelatin, and Laminin.

Any mDAPs may be expanded using the expansion medium of the present disclosure. Examples of mDAPs comprise fetal brain-derived mDAPs; hPSC-derived mDAPs; and mDAPs obtained via transdifferentiation from other cell types. The mDAPs may be derived (e.g., differentiated) from pluripotent stem cells. Pluripotent stems cells can comprise induced pluripotent stem cells (e.g. hiPSCs), embryonic stem cells (e.g., hESCs), naïve PSCs (NPSCs) and extended pluripotent stem cells (EPSCs). In certain embodiments, the mDAPs are ESC-derived midbrain Dopaminergic Progenitor cells (emDAPs). In certain embodiments, the mDAPs are iPSC-derived midbrain Dopaminergic Progenitor cells (imDAPs). In certain embodiments, the mDAPs are NPSC-derived midbrain Dopaminergic Progenitor cells (nmDAPs). In certain embodiments, the mDAPs are EPSC-derived midbrain Dopaminergic Progenitor cells (epmDAPs).

ESCs (e.g., hESCs) and iPSCs (e.g., hiPSCs) are known in the art and can be readily obtained using conventional methods, for example, those described in the existing technologies, or commercially available products. For example, CytoTune iPS 2.0 Sendai Reprogramming Kit (ThermoFisher Scientific) can be used to reliably generate induced pluripotent stem cells (iPSCs) from somatic cells, including PBMCs and T-cells.

Such iPSCs (e.g., hiPSCs) can be cultured under defined conditions to generate mDAPs. For example, iPSCs (e.g., hiPSCs) can be cultured on Matrigel under defined conditions in mTeSR™ medium (Stemcell Technologies, Cat. #85850), and subconfluent hiPSCs are passaged onto fresh Matrigel-coated plates and cultured for additional time (e.g., 24 hours) in iPSC medium to reach 90-100% confluency. Once confluent, the medium can be changed to induce mDAPs for a further period (such as 1-3 days), with optional daily medium change as necessary. e.g., Fedele et al., *Scientific Reports* 7: 6036| DOI:10.1038/s41598-017-05633-1 (2017, incorporated by reference).

As implied by the name, the basal medium can support the survival, maintenance, growth, and proliferation of cells as a medium, and is a basal component for the expansion medium. Generally, the basal medium comprises about 95% to 99% by volume of the expansion medium. The basal medium used in the expansion medium of the present disclosure may be a common basal medium or a basal medium specialized for neural cells such as Neural basal medium.

Examples of the common basal medium comprises DMEM:F12 (e.g., Gibco Cat. #C11330500BT), BME medium (e.g., Gibco Cat. #21010046, or Sigma-Aldrich Cat. #B9638), IMDM medium (e.g., Gibco Cat. #12440053; or Sigma-Aldrich Cat. #13390), Eagle MEM medium (e.g., Minimum Essential Medium (MEM), developed by Harry Eagle, Sigma-Aldrich Cat. #M2414/M2279/M5690), α-MEM medium (e.g., Gibco Cat. #12561056; or, Sigma-Aldrich Cat. #M0894), DMEM medium (e.g., Gibco Cat. #21068028), RPMI 1640 medium (e.g., Gibco Cat. #11875093), Ham's F12 medium (e.g., Gibco Cat. #11765054), or a mixture thereof.

Examples of the Neural basal medium comprises NEUROBASAL™ basal medium (e.g., Gibco Cat. #21103049), NEUROBASAL-A™ basal medium (e.g., Gibco Cat. #10888022), NEUROBASAL PLUS™ basal medium (e.g., Gibco Cat. #A3582901), and/or BRAINPHYS™ basal medium (e.g., STEMCELL Cat. #05790).

In certain embodiments, the basal medium comprises DMEM:F12 and NEUROBASAL™ neural basal medium. In certain embodiments, the neural basal medium is present in the basal medium at about 0% to about 100%, about 25% to about 75%, or about 50% by volume.

In certain embodiments, the neural growth supplement is selected from the group consisting of B27, N1, N2, and any combination thereof. In certain embodiments, the neural growth supplement comprises B27 (e.g., B27 from GIBCO BRL Cat. #12587010).

According to the present disclosure, the concentration of the neural growth supplement is not particularly limited as long as it does not impede the promotion of the expansion of mDAPs. In certain embodiments, the neural growth supplement is present in the culture medium at a concentration of about 0.1% to about 20% by volume, preferably about 0.1% to about 10% by volume, and more preferably about 0.5% to about 5% by volume.

The Wnt signaling pathway is defined by a series of events that occur when a Wnt protein ligand binds to a cell-surface receptor of a Frizzled receptor family member. This results in the activation of Dishevelled (Dsh) family proteins which inhibit a complex of proteins that includes axin, GSK-3, and the protein APC to degrade intracellular β-catenin. The resulting enriched nuclear β-catenin enhances transcription by TCF/LEF family of transcription factors.

As used herein, a Wnt signaling pathway activator refers to an agonist of the Wnt signaling pathway (e.g., agents capable of upregulating activity and/or amount of a component participating in the Wnt signaling pathway) and can be interchanged with a "Wnt signaling pathway agonist," "Wnt agonist," "Wnt pathway activator," or "Wnt activator". The Wnt signaling pathway activator includes an agent that directly or indirectly activates TCF/LEF-mediated transcription in a cell, such as through modulating the activity of any one of the proteins/genes in the Wnt signaling cascade (e.g., enhancing the activity of a positive regulator of the Wnt signaling pathway, or inhibiting the activity of a negative regulator of the Wnt signaling pathway).

Wnt activators are selected from true Wnt activators that bind and activate a Frizzled receptor family member including any and all of the Wnt family proteins, an inhibitor of intracellular β-catenin degradation, and activators of TCF/LEF. The Wnt activator may stimulate a Wnt activity in a cell by at least about 10%, at least about 20%, at least about 30%, at least about 50%, at least about 70%, at least about 90%, at least about 100%, at least about 2-fold, 3-fold, 5-fold, 10-fold, 20-fold, 50-fold, 100-fold, 200-fold, 500-fold, or 1000-fold or more relative to a level of the Wnt activity in the absence of the Wnt activator. As is known to a person of skill in the art, a Wnt activity can be determined by measuring the transcriptional activity of Wnt, for example by pTOPFLASH and pFOPFLASH Tcf luciferase reporter constructs (see Korinek et al., *Science* 275:1784-1787, 1997, incorporated herein by reference).

Representative Wnt activator may comprise a secreted glycoprotein including Wnt-1/Int-1, Wnt-2/Irp (Int-1-related Protein), Wnt-2b/13, Wnt-3/Int-4, Wnt-3a (R&D systems), Wnt-4, Wnt-5a, Wnt-5b, Wnt-6 (Kirikoshi et al., *Biochem. Biophys. Res. Com.*, 283:798-805, 2001), Wnt-7a (R&D systems), Wnt-7b, Wnt-8a/8d, Wnt-8b, Wnt-9a/14, Wnt-9b/14b/15, Wnt-10a, Wnt-10b/12, Wnt-11, and Wnt-16. An overview of human Wnt proteins is provided in "The Wnt Family of Secreted Proteins," R&D Systems Catalog, 2004 (incorporated herein by reference).

Further Wnt activators include the R-spondin family of secreted proteins, which is implicated in the activation and regulation of Wnt signaling pathway, and which comprises at least 4 members, namely R-spondin 1 (NU206, Nuvelo, San Carlos, CA), R-spondin 2 (R&D systems), R-spondin 3, and R-spondin 4. Wnt activators also include Norrin (also known as Norrie Disease Protein or NDP) (R&D systems), which is a secreted regulatory protein that functions like a Wnt protein in that it binds with high affinity to the Frizzled-4 receptor and induces activation of the Wnt signaling pathway (Kestutis Planutis et al., *BMC Cell Biol.* 8:12, 2007).

Wnt activators further include a small-molecule agonist of the Wnt signaling pathway, an aminopyrimidine derivative (N4-(benzo[d][1,3]dioxol-5-ylmethyl)-6-(3-methoxyphenyl)pyrimidine-2,4-diamine), as described in Liu et al. (*Angew Chem. Int. Ed. Engl.* 44(13): 1987-1990, 2005, incorporated herein by reference).

In certain embodiments, the Wnt signaling pathway activator is a GSK-inhibitor, such as GSK-3p inhibitor. GSK3 inhibitors may include, for example and without limitation, polynucleotides, polypeptides, and small molecules.

GSK-inhibitors comprise small-interfering RNAs (siRNA, Cell Signaling), lithium (Sigma), kenpaullone (Biomol International, Leost et al., *Eur. J. Biochem.* 267:5983-5994, 2000), 6-Bromoindirubin-30-acetoxime (Meyer et al., *Chem. Biol.* 10:1255-1266, 2003), SB 216763, and SB 415286 (Sigma-Aldrich), and FRAT-family members and FRAT-derived peptides that prevent interaction of GSK-3 with axin. An overview is provided by Meijer et al. (*Trends in Pharmacological Sciences* 25:471-480, 2004, incorporated herein by reference). Methods and assays for determining a level of GSK-3 inhibition are known in the art, and may comprise, for example, the methods and assay as described in Liao et al. (*Endocrinology* 145(6):2941-2949, 2004, incorporated herein by reference).

In certain embodiments, Wnt activator is selected from: one or more of a Wnt family member, R-spondin 1-4 (such as R-spondin 1), Norrin, Wnt3a, Wnt-6, and a GSK-inhibitor.

In certain embodiments, any of the specific protein-based Wnt activator referenced herein, such as R-spondin 1 to R-spondin 4, any Wnt family member, etc. may be replaced by a natural, synthetic, or recombinantly produced homologs or fragments thereof that retain at least about 80%, 85%, 90%, 95%, 99% of the respective Wnt activator activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

In certain embodiments, the examples of GSK-3p inhibitor comprises: Kenpaullone, 1-Azakenpaullone, CHIR99021, CHIR98014, NPU31112, TWS119, AZD2858, AZD1080, SB415286, LY2090314, AR-A014418, CT20026, SB216763, TDZD-8, BIO, BIO-Acetoxime, (5-Methyl-1H-pyrazol-3-yl)-(2-phenylquinazolin-4-yl) amine, Pyridocarbazole-cyclopenadienylruthenium complex(GSK-3 Inhibitor XV), 2-Thio(3-iodobenzyl)-5-(1-pyridyl)[1,3,4]-oxadiazole, OTDZT, alpha-4-Dibromoacetophenone, 3-(1-(3-Hydroxypropyl)-1H-pyrrolo[2,3-b]pyridin-3-yl]-4-pyrazin-2-yl-pyrrole-2,5-dione, L803 H-KEAPPAPPQSpP-NH2 or its myristoylated form, 2-Chloro-1-(4,5-dibromo-thiophen-2-yl)-ethanone, GF109203X, R0318220 and any combination thereof.

In certain embodiments, the WNT signaling pathway activator is selected from the group consisting of Kenpaullone, 1-Azakenpaullone, CHIR99021, CHIR98014, NP031112, TWS119, AZD2858, AZD1080, SB415286, LY2090314, AR-A014418, SB216763, BIO(GSK 3 Inhibitor IX), BIO-Acetoxime, (5-Methyl-1H-pyrazol-3-yl)-(2-phenylquinazolin-4-yl)amine, 2-Thio(3-iodobenzyl)-5-(1-pyridyl)[1,3,4]-oxadiazole, alpha-4-Dibromoacetophenone, 3-(1-(3-Hydroxypropyl)-1H-pyrrolo[2,3-b]pyridin-3-yl]-4-pyrazin-2-yl-pyrrole-2,5-dione, 2-Chloro-1-(4,5-dibromo-thiophen-2-yl)-ethanone, R0318220, GF109203X and any combination thereof.

Representative structures of certain WNT signaling pathway activators that may be used in the expansion medium of the present disclosure are provided below, many of which are widely commercially available from multiple sources, with indicated Cat. No. from such selected commercial sources.

However, it should be generally understood, in all instances herein where a given source is provided, such source is not limiting. Alternative sources (commercial or non-commercial) of the same or similar materials, chemicals, or compounds, can be readily used in view of the exemplary structures of the materials, chemicals, or compounds.

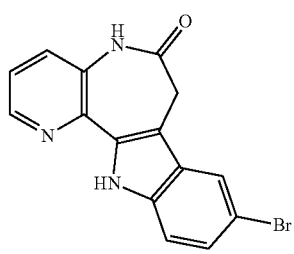 [SMILES: O=C1Cc2c([nH]c3ccc(Br)cc23)-c2ncccc2N1]

Azakenpaullone: MCE, #HY-59090; APExBio, #B3690; Sigma-Aldrich, #A3734; CAS No.: 676586-65-9.

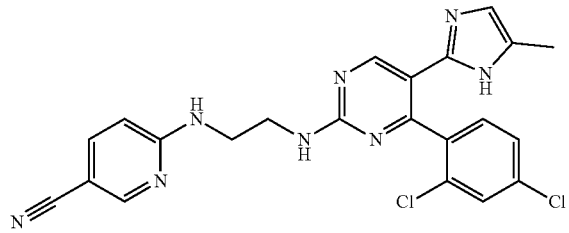 [SMILES: Cc1cnc(-c2cnc(NCCNc3ccc(C#N)cn3)nc2-c2ccc(Cl)cc2Cl)[nH]1]

CHIR99021: APExBio, #A3011.

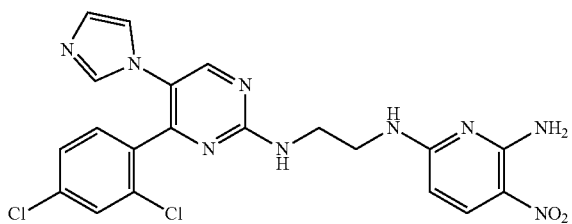 [SMILES: Nc1nc(NCCNc2ncc(-n3ccnc3)c(-c3ccc(Cl)cc3Cl)n2)ccc1[N+](=O)[O-]]

CHIR98014: Sigma-Aldrich, #SML1094; CAS No.: 252935-94-7.

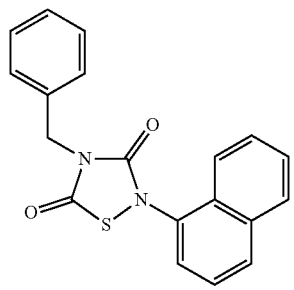 [SMILES: O=c1sn(-c2cccc3ccccc23)c(=O)n1Cc1ccccc1]

NP031112 (Tideglusib): Sigma-Aldrich, #SML0339; APExBio, #B1539; MCE, #HY-14872; CAS No.: 865854-05-3.

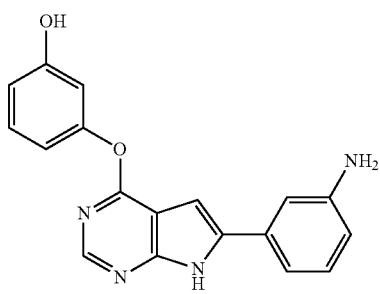 [SMILES: Nc1cccc(-c2cc3c(Oc4cccc(O)c4)ncnc3[nH]2)c1]

TWS119: Sigma-Aldrich, #SML1271; APExBio, #B1540; MCE, #HY-10590; CAS No.: 601514-19-6.

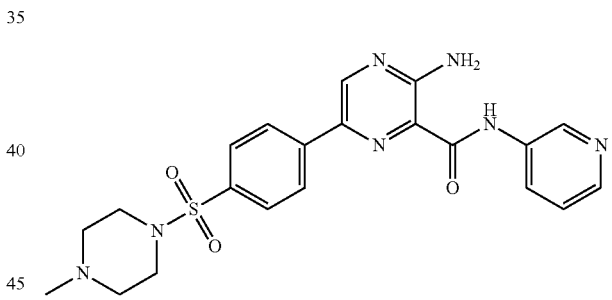

AZD2858: APExBio, #B1537; MCE, #HY-15761; CAS No.: 486424-20-8.

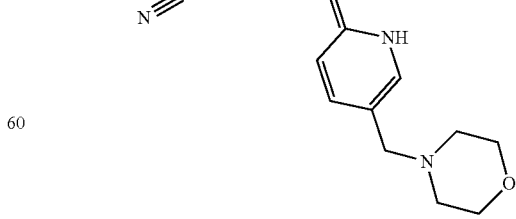

AZD1080: APExBio, #B1536; MCE, #HY-13862, CAS No.: 612487-72-6.

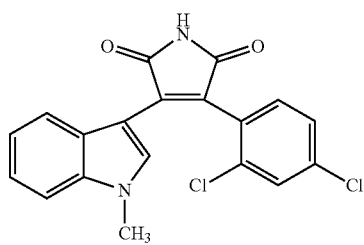 [SMILES: Cn1cc(C2=C(c3ccc(Cl)cc3Cl)C(=O)NC2=O)c2ccccc21]

SB415286: Sigma-Aldrich, #S3567; APExBio, #A8241; MCE, #HY-15438; CAS No.: 280744-09-4.

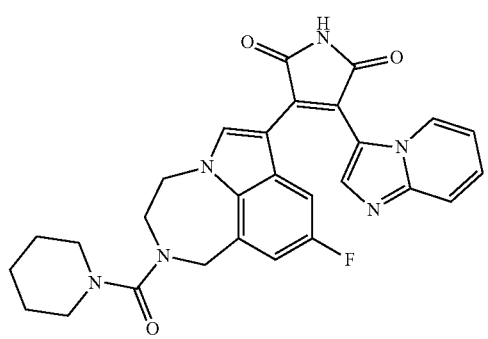 [SMILES: O=C1NC(=O)C(c2cnc3ccccn23)=C1c1cn2c3c(cc(F)cc13)CN(C(=O)N1CCCCC1)CC2]

LY2090314: Sigma-Aldrich, #SML1438; APExBio, #A3570; MCE, #HY-16294; CAS No.: 603288-22-8.

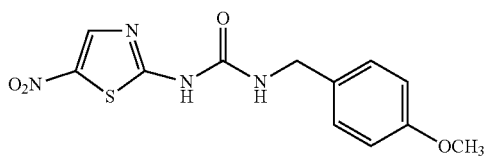 [SMILES: COc1ccc(CNC(=O)Nc2ncc([N+](=O)[O-])s2)cc1]

AR-A014418: Sigma-Aldrich, #A3230; APExBio, #A3184; MCE, #HY-10512; CAS No.: 487021-53-3.

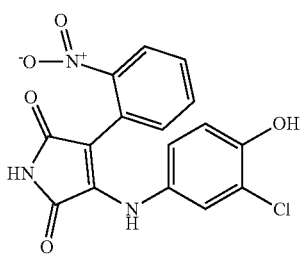

SB216763: Sigma-Aldrich, #S3442; APExBio, #A8240; MCE, #HY-12012; CAS No.: 280744-09-4.

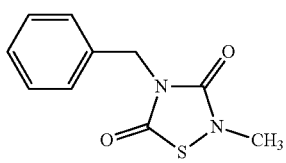

TDZD-8: Sigma-Aldrich, #T8325; APExBio, #B1249; MCE, #HY-11012; CAS No.: 327036-89-5.

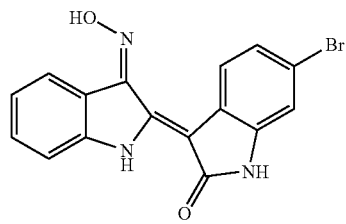 [SMILES: O=C1Nc2cc(Br)ccc2/C1=C1/Nc2ccccc2/C1=N\O]

BIO(GSK 3 Inhibitor IX): Sigma-Aldrich, #B1686; APExBio, #B1538; MCE, #HY-10580; CAS No.: 667463-62-9.

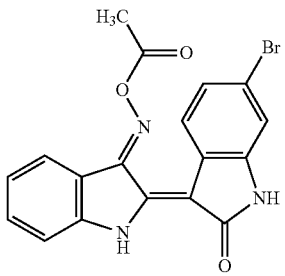 [SMILES: CC(=O)O/N=C1/C(=C2/C(=O)Nc3cc(Br)ccc32)Nc2ccccc21]

BIO-Acetoxime; Sigma-Aldrich, #SML0531; APExBio, #B5488; MCE, #HY-15356; CAS No.: 667463-85-6.

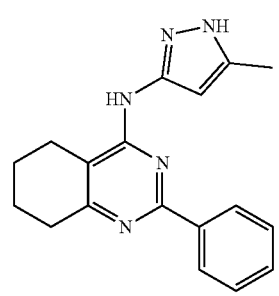 [SMILES: Cc1cc(Nc2nc(-c3ccccc3)nc3c2CCCC3)n[nH]1]

(5-Methyl-1H-pyrazol-3-yl)-(2-phenylquinazolin-4-yl) amine(GSK-3 Inhibitor XIII): MCE, #HY-112392; absin, #abs819580; aladdin, #G338805; CAS No.: 404828-08-6.

13

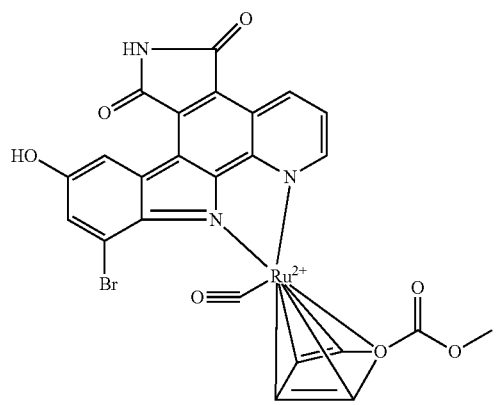

Pyridocarbazole-cyclopenadienylruthenium complex (GSK-3 Inhibitor XV): Sigma-Aldrich, #361558, CAS No.: 936112-69-5.

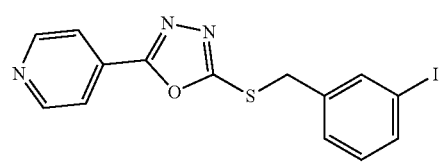 [SMILES: Ic1cccc(CSc2nnc(-c3ccncc3)o2)c1]

2-Thio(3-iodobenzyl)-5-(1-pyridyl)[1,3,4]-oxadiazole (GSK3 Inhibitor II): APExBio, #C4599; CAS No.: 478482-75-6.

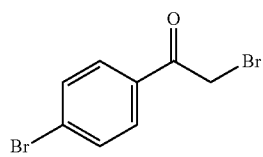 [SMILES: O=C(CBr)c1ccc(Br)cc1]

alpha-4-Dibromoacetophenone (2,4'-Dibromoacetophenone/4'-Bromophenacyl bromide): Sigma-Aldrich, #D38308; CAS No.: 99-73-0.

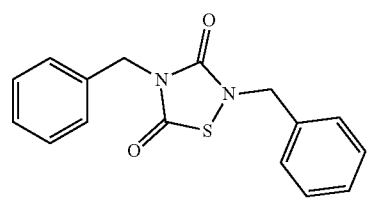 [SMILES: O=c1sn(Cc2ccccc2)c(=O)n1Cc1ccccc1]

OTDZT (2,4-dibenzyl-5-oxo thiadiazolidine-3-thione): CAS No.: 373357-10-9.

14

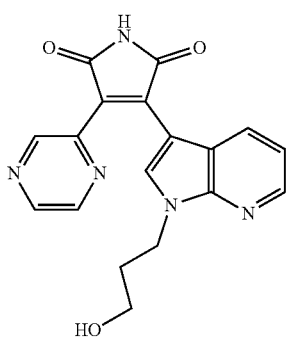 [SMILES: O=C1NC(=O)C(c2cn(CCCO)c3ncccc23)=C1c1cnccn1]

3-(1-(3-Hydroxypropyl)-1H-pyrrolo[2,3-b]pyridin-3-yl]-4-pyrazin-2-yl-pyrrole-2,5-dione (GSK-3β inhibitor XI): Sigma-Aldrich, #361553; aladdin, #G338716-1 mg; CAS No.: 626604-39-5.

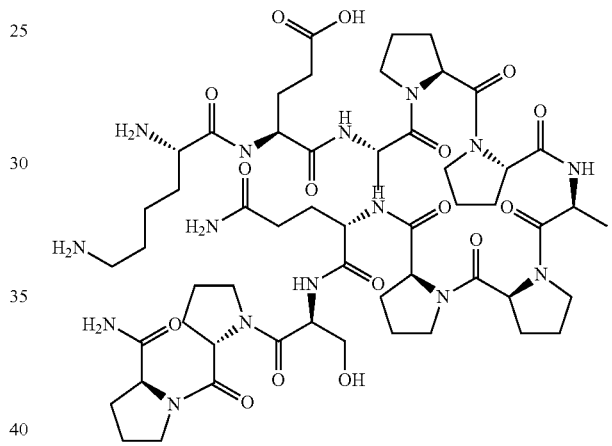

(?) indicates text missing or illegible when filed

L803 H-KEAPPAPPQSpP-NH2: CAS No.: 348089-28-1.

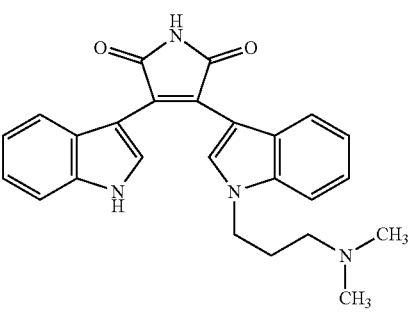 [SMILES: CN(C)CCCn1cc(C2=C(c3c[nH]c4ccccc34)C(=O)NC2=O)c2ccccc21]

GF109203X(Bisindolylmaleimide I): Sigma-Aldrich, #G2911; APExBio, #A8342; MCE, #HY-13867; CAS No.: 133052-90-1.

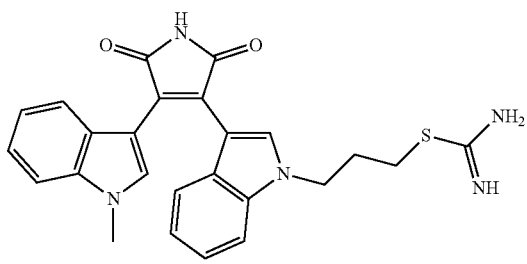 [SMILES: Cn1cc(C2=C(c3cn(CCCSC(=N)N)c4ccccc34)C(=O)NC2=O)c2ccccc21]

RO318220: MCE, #HY-13866A; CAS No.: 125314-64-9.

According to the present disclosure, the concentration of the WNT signaling pathway activator is not particularly limited as long as it does not impede the promotion of the expansion of mDAPs. In certain embodiments, the WNT signaling pathway activator is present in the culture medium at a concentration of about 0.5 µM to about 20 µM, preferably about 0.5 µM to about 10 µM, and more preferably about 0.5 µM to about 5 µM.

In certain embodiments, the WNT signaling pathway activator comprises CHIR99021. In certain embodiments, the WNT signaling pathway activator (e.g., CHIR99021) is present in the expansion medium at about 1 µM to about 5 µM, about 1.25 µM to about 5 µM, about 1.5 µM to about 5 µM, or about 2 µM to about 4 µM.

The ROCK inhibitor comprises an agent which inhibits binding between ROCK and a ROCK receptor. The ROCK inhibitor used in the expansion medium of the present disclosure can facilitate the expansion of mDAPs, for example, increase the expansion efficiency and the expression of the mDAP-specific markers such as FOXA2.

In certain embodiments, the ROCK inhibitor is selected from the group consisting of: Y27632, HA100, HA1152, HA-1077, and any combination thereof.

Y-27632 is also known as (R)-(+)-trans-4-(1-aminoethyl)-N-(4-pyridyl) cyclohexanecarboxamide dihydrochloride (e.g., Sigma-Aldrich). HA100 is also known as 5-(1-piperazinylsulfonyl)-isoquinoline, dihydrochloride. HA1077 is also known as fasudil hydrochloride or 5-(1,4-diazepan-1-ylsulfonyl)isoquinoline hydrochloride (Cayman Chemical). H-1152 is also known as (S)-(+)-2-methyl-1-[(4-methyl-5-isoquinolinyl) sulfonyl]-hexahydro-1H-1,4-diazepine dihydrochloride (Tocris Bioscience). Other ROCK inhibitors include N-(6-fluoro-1H-indazol-5-yl)-2-methyl-6-oxo-4-(4-(trifluoromethyl)phenyl)-1,4,5,6-tetrahydropyridine-3-carboxamide (GSK429286A, Stemgent).

Representative structures of certain ROCK inhibitors that may be used in the expansion medium of the present disclosure are provided below, many of which are widely commercially available from multiple sources, with indicated Cat. No. from such selected commercial sources (though such sources are not limiting).

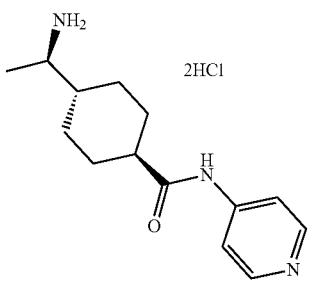 [SMILES: C[C@@H](N)[C@H]1CC[C@H](C(=O)Nc2ccncc2)CC1]

Y-27632 (MCE Cat. #HY-10071, CAS No.: 146986-50-7).

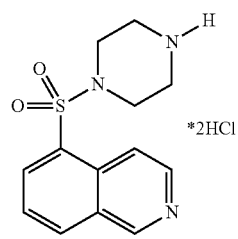 [SMILES: O=S(=O)(c1cccc2cnccc12)N1CCNCC1]

HA-100 (hydrochloride) (absin Cat. #abs47045575).

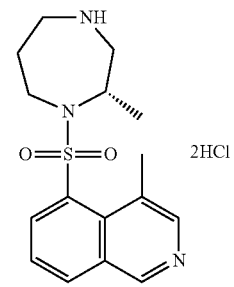 [SMILES: Cc1cncc2cccc(S(=O)(=O)N3CCCNC[C@@H]3C)c12]

H1152 (MCE Cat. #HY-15720, CAS No.: 451462-58-1).

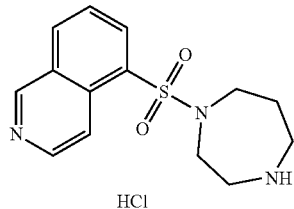 [SMILES: O=S(=O)(c1cccc2cnccc12)N1CCCNCC1 ; Cl]

HA-1077 (Fasudil/AT877) (MCE Cat. #HY-10341A, CAS No.: 103745-39-7).

In certain embodiments, the ROCK inhibitor comprises Y27632. In certain embodiments, the ROCK inhibitor (e.g., Y27632) is present in the expansion medium at about 1 µM to about 50 µM, preferably about 1 µM to about 20 µM, or more preferably about 5 µM to about 15 µM.

TGF-β signaling typically begins with binding of a TGF-β superfamily ligand to a Type II receptor, which recruits and phosphorylates a Type I receptor. The Type I receptor then phosphorylates SMADs, which act as transcription factors in the nucleus and regulate target gene expression. Alternatively, TGF-β signaling can activate MAP kinase signaling pathways, for example, via p38 MAP kinase. The TGF-β inhibitor used in the expansion medium of the present disclosure can facilitate the expansion of mDAPs, for example, increase the expansion efficiency and the expression of the mDAP-specific markers such as FOXA2.

The TGF-β inhibitor as used herein include an agent that reduces the activity of the TGF-β signaling pathway. There are many different ways of disrupting the TGF-β signaling pathway. For example, TGF-β signaling may be disrupted by: inhibition of TGF-β expression by a small-interfering RNA strategy; inhibition of furin (a TGF-β activating protease); inhibition of the pathway by physiological inhibitors, such as inhibition of BMP by Noggin, DAN or DAN-like proteins; neutralization of TGF-β with a monoclonal antibody; inhibition with small-molecule inhibitors of TGF-β receptor kinase 1 (also known as activin receptor-like kinase, ALK5), ALK4, ALK6, ALK7 or other TGF-β-related receptor kinases; inhibition of Smad 2 and Smad 3 signaling by overexpression of their physiological inhibitor, Smad 7, or by using thioredoxin as an Smad anchor disabling Smad from activation For example, a TGF-β inhibitor may target a serine/threonine protein kinase selected from: TGF-β receptor kinase 1, ALK4, ALK5, ALK7, or p38. ALK4, ALK5 and ALK7 are all closely related receptors of the TGF-β superfamily. An inhibitor of any one of these kinases is one that effects a reduction in the enzymatic activity of any one (or more) of these kinases.

In certain embodiments, a TGF-β inhibitor may bind to and inhibit the activity of a Smad protein, such as R-SMAD or SMAD1-5 (i.e., SMAD1, SMAD2, SMAD3, SMAD4 or SMAD5).

In certain embodiments, a TGF-β inhibitor may bind to and reduces the activity of Ser/Thr protein kinase selected from: TGF-β receptor kinase 1, ALK4, ALK5, ALK7, or p38.

In certain embodiments, the expansion medium of the present disclosure comprises an inhibitor of ALK5.

Various methods for determining if a substance is a TGF-β inhibitor are known. For example, a cellular assay may be used in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., *Br. J. Pharmacol.* 145(2): 166-177, 2005, incorporated herein by reference). Another example is the ALPHASCREEN® phosphosensor assay for measurement of kinase activity (Drew et al., *J. Biomol. Screen.* 16(2): 164-173, 2011, incorporated herein by reference).

A TGF-β inhibitor useful for the present disclosure may be a protein, a peptide, a small-molecule, a small-interfering RNA, an antisense oligonucleotide, an aptamer, an antibody or an antigen-binding portion thereof. The inhibitor may be naturally occurring or synthetic. Examples of small-molecule TGF-β inhibitors that can be used in the context of the present disclosure include, but are not limited to, RepSox (2-[5-(6-methylpyridin-2-yl)-1H-pyrazol-4-yl]-1,5-naphthyridine), SB431542, SB505124, LY36494, SJN-2511, A83-01, D4476, GW788388, LY364947, LY580276, SB525334, SD208, GW6604, and any combination thereof.

In certain embodiments, the TGF-β inhibitor is selected from the group consisting of RepSox, A83-01, SB431542, D4476, GW788388, LY364947, SB525334, SB505124, SD208, GW6604, and any combination thereof.

Representative structures of certain TGF-β inhibitors that may be used in the expansion medium of the present disclosure are provided below, many of which are widely commercially available from multiple sources, with indicated Cat. No. from such selected commercial sources (though such sources are not limiting).

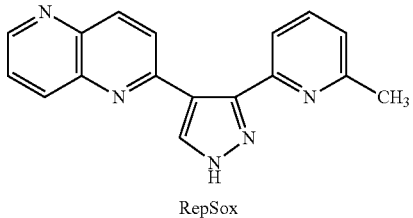 [SMILES: Cc1cccc(-c2n[nH]cc2-c2ccc3ncccc3n2)n1]

RepSox

RepSox (2-[5-(6-methylpyridin-2-yl)-1H-pyrazol-4-yl]-1,5-naphthyridine) (Sigma-Aldrich Cat. #R0158; APExBio Cat. #A3754; MCE Cat. #HY-13012; CAS No.: 446859-33-2).

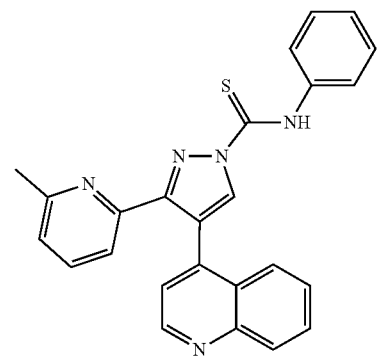 [SMILES: Cc1cccc(Cc2nn(C(=S)Nc3ccccc3)cc2-c2ccnc3ccccc23)n1]

A83-01 (Sigma-Aldrich Cat. #SML0788; APExBio Cat. #A3133; MCE Cat. #HY-10432; CAS No.: 909910-43-6).

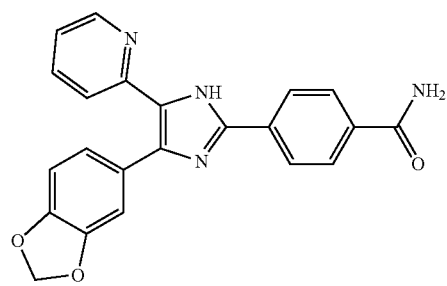 [SMILES: NC(=O)c1ccc(-c2nc(-c3ccc4c(c3)OCO4)c(-c3ccccn3)[nH]2)cc1]

SB431542 (APExBio Cat. #A8249, CAS No.: 301836-41-9).

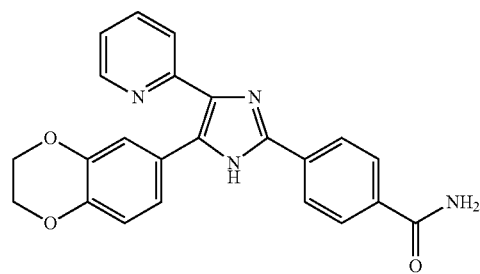 [SMILES: NC(=O)c1ccc(-c2nc(-c3ccccn3)c(-c3ccc4c(c3)OCCO4)[nH]2)cc1]

D4476 (Sigma-Aldrich Cat. #D1944; APExBio Cat. #A3342; MCE Cat. #HY-10324; CAS No.: 301836-43-1).

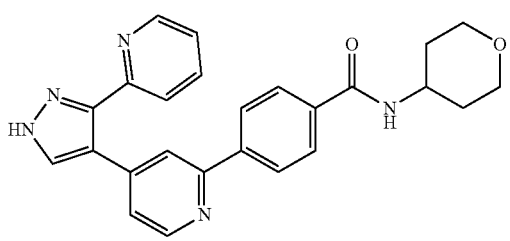 [SMILES: O=C(NC1CCOCC1)c1ccc(-c2cc(-c3c[nH]nc3-c3ccccn3)ccn2)cc1]

GW788388 (APExBio Cat. #A8301; MCE Cat. #HY-10326; CAS No.: 452342-67-5).

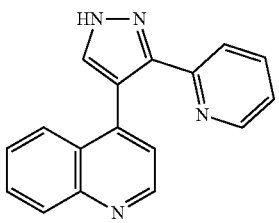 [SMILES: c1ccc(-c2n[nH]cc2-c2ccnc3ccccc23)nc1]

LY364947 (Sigma-Aldrich Cat. #L6293; APExBio Cat. #B2287; MCE Cat. #HY-31462; CAS No.: 396129-53-6).

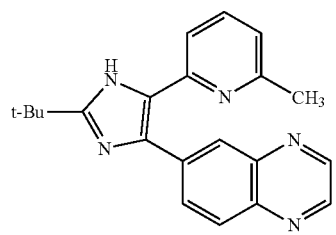 [SMILES: Cc1cccc(-c2[nH]c(C(C)(C)C)nc2-c2ccc3nccnc3c2)n1]

SB525334 (Sigma-Aldrich Cat. #S8822; APExBio Cat. #A5602; MCE Cat. #HY-12043; CAS No.: 356559-20-1).

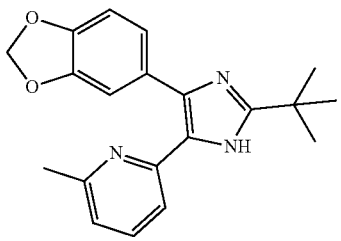 [SMILES: Cc1cccc(-c2[nH]c(C(C)(C)C)nc2-c2ccc3c(c2)OCO3)n1]

SB505124 (APExBio Cat. #B2289; MCE Cat. #HY-13521; CAS No.: 694433-59-5).

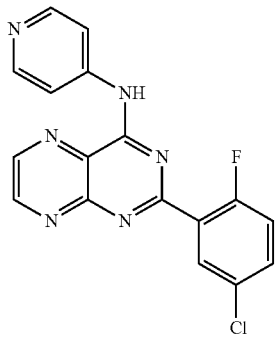 [SMILES: Fc1ccc(Cl)cc1-c1nc(Nc2ccncc2)c2nccnc2n1]

SD208 (Sigma-Aldrich Cat. #S7071; APExBio Cat. #A3808; MCE Cat. #HY-10324; CAS No.: 627536-09-8).

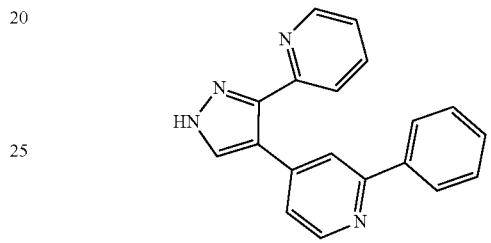

GW6604 (absin Cat. #abs814099; CAS No.: 452342-37-9).

According to the present disclosure, the concentration of the TGF-β inhibitor is not particularly limited as long as it does not impede the promotion of the expansion of mDAPs. In certain embodiments, the TGF-β inhibitor is present in the culture medium at a concentration of about 0.5 μM to about 50 μM, preferably about 1 μM to about 20 μM, and more preferably about 1 μM to about 15 μM.

In certain embodiments, the TGF-β inhibitor comprises SB431542. In certain embodiments, the SB431542 is present in the expansion medium at about 0.5 μM to about 50 μM, about 1 μM to about 20 μM, or about 1 μM to about 15 μM.

In certain embodiments, the culture medium of the present disclosure may optionally further comprise a glutamine or its derivative.

In certain embodiments, the glutamine or its derivative comprises L-alanyl-L-glutamine dipeptide (e.g., GLUTA-MAX™ brand L-alanyl-L-glutamine dipeptide, Gibco Cat. #35050061), L-Glutamine (e.g., Sigma-Aldrich Cat. #G2150/G7513; APExBio Cat. #A8461; MCE Cat. #HY-N0390; CAS No.: 56-85-9), or a mixture thereof.

In certain embodiments, the glutamine or its derivative is present in the culture medium at a concentration of about 0.5% to 5% by volume, and preferably about 0.5% to 2.5% by volume.

In certain embodiments, the culture medium of the present disclosure may optionally further comprise an antioxidant.

In certain embodiments, the antioxidant comprises ascorbic acid (e.g., Sigma Cat. #A8960) or its salt (e.g., Na salt, Mg salt) or its analogue or derivative, SOD (e.g., Sigma Cat. #S7571, S9697, S5395, S8160, S9636, S8409, 57446, CAS No.: 9054-89-1), or a mixture thereof.

In certain embodiments, the antioxidant (e.g, ascorbic acid) is present in the culture medium of the present disclosure at a concentration of about 5 μg/mL to about 200

μg/mL, preferably about 15 μg/mL to about 100 μg/mL, and more preferably about 30 μg/mL to about 80 μg/mL.

In certain embodiments, the culture medium of the present disclosure further comprises a fibroblast growth factor. In certain embodiments, the fibroblast growth factor comprises FGF2 (e.g., Nuwacell), FGF1 (e.g., MCE Cat. #HY-P7001), FGF8 (e.g., MCE Cat. #HY-P7347, MCE Cat. #HY-P7349, MCE Cat. #HY-P7350) and/or FGF20 (e.g., R&D Cat. #2547-FG).

In certain embodiments, the fibroblast growth factor (e.g., FGF2 or FGF8) is present in the expansion medium at about 1 ng/mL to about 2.00 ng/mL, about 5 ng/mL to about 50 ng/mL, or about 5 ng/mL to about 20 ng/mL.

In certain embodiments, the culture medium of the present disclosure further comprises a BMP4 inhibitor.

In certain embodiments, the BMP4 inhibitor comprises Dorsomorphin, LDN193189 or a combination thereof. Representative structures of certain BMP4 inhibitors that may be used in the culture medium of the present disclosure are provided below, many of which are widely commercially available from multiple sources, with indicated Cat. No. from such selected commercial sources.

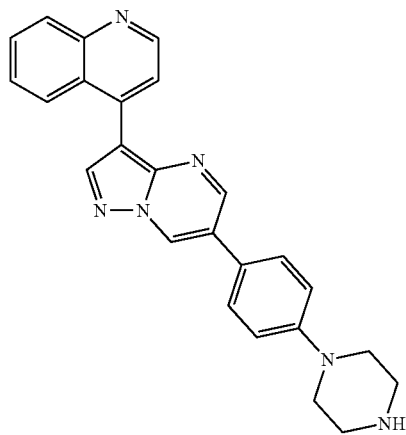 [SMILES: c1ccc2c(-c3cnn4cc(-c5ccc(N6CCNCC6)cc5)cnc34)ccnc2c1]

LDN193189 (MCE Cat. #HY-12071A, CAS No.: 1062368-24-4).

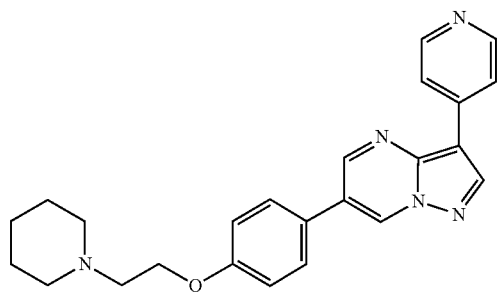 [SMILES: c1cc(-c2cnn3cc(-c4ccc(OCCN5CCCCC5)cc4)cnc23)ccn1]

Dorsomorphin (Sigma-Aldrich Cat. #P5499; APExBio Cat. #B3252; MCE Cat. #HY-13418A; CAS No.: 866405-64-3).

In certain embodiments, the BMP inhibitor (e.g., LDN193189) is present in the culture medium at about 0.05 μM to about 1.0 μM, or about 0.1 μM to about 0.4 μM.

In certain embodiments, the culture medium of the present disclosure does not comprise FGF8, and/or FGF2.

In certain embodiments, the culture medium of the present disclosure comprises: (a) about 1 μM to about 10 μM of the WNT signaling pathway activator; (b) about 1 μM to about 20 μM of the ROCK inhibitor; (c) about 1 μM to about 20 μM of the TGF-β inhibitor; and, (d) about 0.1% to about 10% by volume of the neural growth supplement, in the basal medium.

In certain embodiments, the culture medium of the present disclosure comprises: (a) about 1 μM to about 10 μM of CHIR99021; (b) about 1 μM to about 20 μM of Y27632; (c) about 1 μM to about 20 μM of SB431542; and, (d) about 0.1% to about 10% by volume of B27, in the basal medium.

In certain embodiments, the culture medium of the present disclosure can provide the expansion fold of at least 32-fold, 36-fold, 40-fold or more for each passage of mDAPs, which is at least 3, 4, 5, 6, 7, 8 or more times as high as that of the previous medium without a TGF-β inhibitor and a Rock inhibitor (about 5-10 fold). In certain embodiments, the culture medium of the present disclosure can provide the expansion fold of at least 32-fold, 36-fold, 40-fold or more for each passage of mDAPs, which is at least 1.6, 1.8, 2 or more times as high as that of the same medium without a TGF-β inhibitor (about 20-fold).

Representative example of mDAP-specific markers is FOXA2. Representative example of mDAP-specific markers comprises FOXA2, and one or more selected from LMX1A, EN1, OTX2, and SOX6. In some embodiments, mDAP-specific markers comprises FOXA2, LMX1A, EN1, OTX2, and SOX6.

2. Coating Matrix Combination for Expanding mDAPs

In a second aspect, the present disclosure provides a coating matrix combination that is capable of promoting the robust expansion of midbrain Dopaminergic Progenitor cells (mDAPs), said coating matrix combination comprising: (a) a first coating matrix that can support cell adhesion for the mDAPs; and, (b) a second coating matrix that can improve the expression of the mDAP-specific markers during the expansion and passaging of the mDAPs, wherein the second coating matrix comprises a Notch agonist.

According to the second aspect, due to the inclusion of the second coating matrix, the above coating matrix combination for expansion can improve the expansion efficiency and expression of the mDAP-specific markers during the expansion and passaging of the mDAPs.

According to the second aspect, the coating matrix combination of the present disclosure may be used in combination with any common mDAP expansion medium in the art or any other suitable mDAP expansion medium. Examples of common mDAP expansion medium comprise Gibco™ PSC Dopaminergic Neuron Differentiation Kit and STEMdiff™ Dopaminergic Neuron Differentiation Kit/STEMdiff™ ($405835).

Any mDAPs may be expanded using the coating matrix combination of the present disclosure. Examples of mDAPs comprise fetal brain-derived mDAPs; hPSC-derived mDAPs; and mDAPs obtained via transdifferentiation from other cell types. The mDAPs may be derived (e.g., differentiated) from pluripotent stem cells. Pluripotent stems cells can comprise induced pluripotent stem cells (e.g. hiPSCs), embryonic stem cells (e.g., hESCs), naïve PSCs (NPSCs) and extended pluripotent stem cells (EPSCs). In certain embodiments, the mDAPs are ESC-derived midbrain Dopaminergic Progenitor cells (emDAPs). In certain embodiments, the mDAPs are iPSC-derived midbrain Dopaminergic Progenitor cells (imDAPs). In certain embodiments, the mDAPs are NPSC-derived midbrain Dopaminergic Progenitor cells (nmDAPs). In certain embodiments, the mDAPs are EPSC-derived midbrain Dopaminergic Progenitor cells (epmDAPs).

ESCs (e.g., hESCs) and iPSCs (e.g., hiPSCs) are known in the art and can be readily obtained using conventional methods, for example, those described in the existing technologies, or commercially available products. For example, CytoTune iPS 2.0 Sendai Reprogramming Kit (ThermoFisher Scientific) can be used to reliably generate induced pluripotent stem cells (iPSCs) from somatic cells, including PBMCs and T-cells.

Such iPSCs (e.g., hiPSCs) can be cultured under defined conditions to generate mDAPs. For example, iPSCs (e.g., hiPSCs) can be cultured on Matrigel under defined conditions in mTeSR™ medium (Stemcell Technologies, Cat. #85850), and subconfluent hiPSCs are passaged onto fresh Matrigel-coated plates and cultured for additional time (e.g., 24 hours) in iPSC medium to reach 90-100% confluency. Once confluent, the medium can be changed to induce mDAPs for a further period (such as 1-3 days), with optional daily medium change as necessary. e.g., Fedele et al., *Scientific Reports* 7: 6036 DOI:10.1038/s41598-017-05633-1 (2017, incorporated by reference).

In certain embodiments, the first coating matrix is selected from the group consisting of vitronectin (VTN, e.g., Nuwacell® Vitronectin, #RP01002), collagen (e.g., Gibco Cat. Collagen I, #A1048301; Collagen I, #17100017; Collagen type II, #17101015; Collagen type IV, #17104019), proteoglycan (e.g., Invitrogen Cat. #RP-77523/RP-77524; MCE Cat. #HY-P76323/HY-P71233), fibronectin (e.g., translocation of the intracellular domain of Notch to the nucleus, where it transcriptionally activates downstream genes.

A "Notch agonist" as used herein includes a molecule that stimulates a Notch activity in a cell by at least about 10%, at least about 20%, at least about 30%, at least about 50%, at least about 70%, at least about 90%, at least about 100%, at least about 3-fold, 5-fold, 10-fold, 20-fold, 50-fold, 100-fold, 200-fold, 500-fold, 1000-fold or more, relative to a level of a Notch activity in the absence of the Notch agonist. As is known in the art, Notch activity can be determined by, for example, measuring the transcriptional activity of Notch, by a 4× wtCBF1-luciferase reporter construct described by Hsieh et al. (*Mol. Cell. Biol.* 16:952-959, 1996, incorporated herein by reference).

In certain embodiments, the Notch agonist is selected from: Delta-Like 4 (DLL4, Nuwacell®), Delta-Like 1 (DLL1, e.g., MCE (HEK293, His), #HY-P7841), Jagged-1 (e.g., MCE Cat. #HY-P1846), Jagged-2 (e.g., (JAG2) #BES23045RP), a variant thereof, and any combination thereof. In certain embodiments, the Notch agonist is DSL peptide (Dontu et al., *Breast Cancer Res.,* 6:R605-R615, 2004).

Representative structures of certain Notch agonists that may be used in the coating matrix combination of the present disclosure are provided below, many of which are widely commercially available from multiple sources, with indicated Cat. No. from such selected commercial sources.

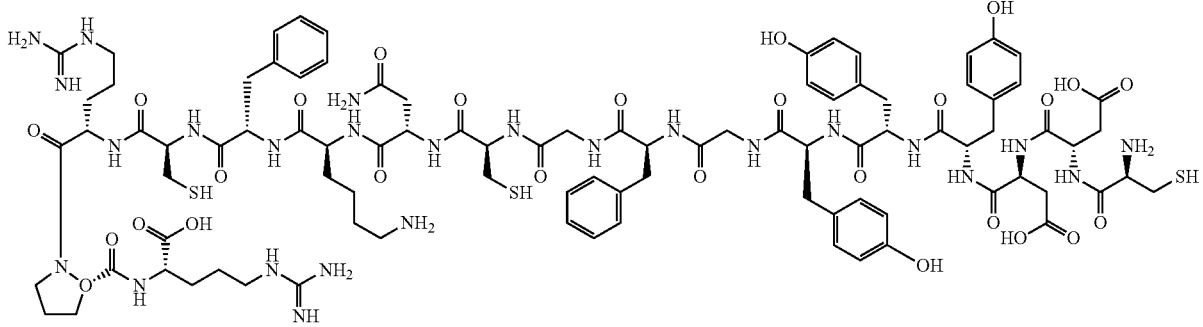

Invitrogen Cat. #RP-43130; MCE Cat. #HY-P70593/HY-P70593G/HY-P73063), entactin (e.g., Sigma-Aldrich Cat. #D8935; MCE Cat. #HY-P71763), elastin (e.g., Sigma-Aldrich Cat. #E7402/E7277/E6902; CAS No.: 9007-58-3), laminin (e.g., Nuwacell® laminin), a functional fragment of any proceeding proteins, hyaluronic acid (e.g., MCE Cat. #HY-B0633A; CAS No.: 9004-61-9), gelatin (e.g., USP, #1288485; MCE Cat. #HY-Y1365; CAS No.: 9000-70-8), and any combination thereof. In certain embodiments, the first coating matrix comprises VTN.

According to the present disclosure, the second coating matrix comprises a Notch agonist. As used herein, Notch agonist refers to an activator of the Notch signaling pathway (e.g., agents capable of upregulating activity and/or amount of a component participating in the Notch signaling pathway). Notch receptor proteins can interact with a number of surface-bound or secreted ligands, including but not limited to Jagged-1, Jagged-2, Delta-like 1, Delta-like 3, Delta-like 4, etc. Upon ligand binding, Notch receptors are activated by serial cleavage events involving members of the ADAM protease family, as well as an intramembranous cleavage regulated by the gamma secretase presinilin. The result is a Jagged-1 (188-204) (e.g., MCE Cat. #HY-P1846; CAS No.: 219127-21-6)

In certain embodiments, the Notch agonist comprises DLL4.

In certain embodiments, any of the specific Notch agonist referenced herein, such as Jagged-1, Jagged-2, Delta-1 and Delta-like 4 may be replaced by a natural, synthetic, or recombinantly produced homologs or fragments thereof that retain at least about 80%, 85%, 90%, 95%, 99% of the respective Notch agonist activity, and/or homologs or fragments thereof that share at least about 60%, 70%, 80%, 90%, 95%, 97%, 99% amino acid sequence identity as measured by any art recognized sequence alignment software based on either a global alignment technique (e.g., the Needleman-Wunsch algorithm) or a local alignment technique (e.g., the Smith-Waterman algorithm).

In certain embodiments, the coating matrix combination comprises VTN and Notch agonist. In certain embodiments, the coating matrix combination comprise VTN and DLL4.

A cell culture surface may be coated with the the expansion coating matrix combination of the present disclosure by conventional technologies in the art. Generally, the first coating matrix and the second coating matrix may be firstly mixed at any ratio and a cell culture surface may be coated with the coating solution. The coating concentrations of the first coating matrix and the second coating matrix may be easily determined by one skilled in the art. For example, the coating concentrations of the first coating matrix and the second coating matrix may be each from 0.5 to 2 μg/cm², such as 1 μg/cm².

In certain embodiments, the coating matrix combination of the present disclosure can provide the expansion fold of at least 36 fold, 38-fold, 40-fold or more for each passage of mDAPs, which is at least 1.8 1.9, 2, or more times as high as that of the previous coating matrix such as VTN (about 20 folds).

Representative example of mDAP-specific markers is FOXA2. Representative example of mDAP-specific markers comprises FOXA2, and one or more selected from LMX1A, EN1, OTX2, and SOX6. In some embodiments, mDAP-specific markers comprise FOXA2, LMX1A, EN1, OTX2, and SOX6.

3. Method for Expanding mDAPs

In a third aspect, the present disclosure provides a method for expanding midbrain Dopaminergic Progenitor cells (mDAPs), comprising contacting the mDAPs with an expansion medium on a culture surface coated with the expansion coating matrix combination of the present disclosure.

According to the third aspect, due to the use of the second coating matrix, the above expansion method can improve the expansion efficiency and expression of the mDAP-specific markers during the expansion and passaging of the mDAPs.

Any mDAPs may be expanded using the expansion method of the present disclosure. Examples of mDAPs comprise fetal brain-derived mDAPs; hPSC-derived mDAPs; and mDAPs obtained via transdifferentiation from other cell types. The mDAPs may be derived (e.g., differentiated) from pluripotent stem cells. Pluripotent stems cells can comprise induced pluripotent stem cells (e.g. hiPSCs), embryonic stem cells (e.g., hESCs), naïve PSCs (NPSCs) and extended pluripotent stem cells (EPSCs). In certain embodiments, the mDAPs are ESC-derived midbrain Dopaminergic Progenitor cells (emDAPs). In certain embodiments, the mDAPs are iPSC-derived midbrain Dopaminergic Progenitor cells (imDAPs). In certain embodiments, the mDAPs are NPSC-derived midbrain Dopaminergic Progenitor cells (nmDAPs). In certain embodiments, the mDAPs are EPSC-derived midbrain Dopaminergic Progenitor cells (epmDAPs).

ESCs (e.g., hESCs) and iPSCs (e.g., hiPSCs) are known in the art and can be readily obtained using conventional methods, for example, those described in the existing technologies, or commercially available products. For example, CytoTune iPS 2.0 Sendai Reprogramming Kit (ThermoFisher Scientific) can be used to reliably generate induced pluripotent stem cells (iPSCs) from somatic cells, including PBMCs and T-cells.

Such iPSCs (e.g., hiPSCs) can be cultured under defined conditions to generate mDAPs. For example, iPSCs (e.g., hiPSCs) can be cultured on Matrigel under defined conditions in mTeSR™ medium (Stemcell Technologies, Cat. #85850), and subconfluent hiPSCs are passaged onto fresh Matrigel-coated plates and cultured for additional time (e.g., 24 hours) in iPSC medium to reach 90-100% confluency. Once confluent, the medium can be changed to induce mDAPs for a further period (such as 1-3 days), with optional daily medium change as necessary. e.g., Fedele et al., *Scientific Reports* 7: 6036|DOI:10.1038/s41598-017-05633-1 (2017, incorporated by reference).

According to the third aspect, any common mDAP expansion medium in the art or any other suitable mDAP expansion medium may be used in the expansion method of the present disclosure. Examples of common mDAP expansion medium comprise Gibco™ PSC Dopaminergic Neuron Differentiation Kit and STEMdiff™ Dopaminergic Neuron Differentiation Kit/STEMdiff™ (#05835).

The expansion coating matrix combination of the present disclosure has been described elsewhere herein (e.g., as described in the Coating Matrix Combination for Expanding mDAPs or the second aspect herein), and these same descriptions are omitted herein for purpose of simplification.

In certain embodiments, the culture surface is in a culture plate, a culture bottle, a culture flask, or a culture vessel. In certain embodiments, the culture plate comprises single or multilayer cell-stacks, 6 wells, 12 wells, 24 wells, 48 wells, 96 wells, 384 wells, 1536 wells or more wells. In certain embodiments, the culture plate comprises flat bottom wells, or round bottom wells.

A cell culture surface may be coated with the the expansion coating matrix combination of the present disclosure by conventional technologies in the art. Generally, the first coating matrix and the second coating matrix may be firstly mixed at any ratio and a cell culture surface may be coated with the coating solution. The coating concentrations of the first coating matrix and the second coating matrix may be easily determined by one skilled in the art. For example, the coating concentrations of the first coating matrix and the second coating matrix may be each from 0.5 to 2 μg/cm², such as 1 μg/cm².

In certain embodiments, the method further comprises replacing the expansion medium with the same medium every several days during the expansion. In certain embodiments, the method further comprises replacing the expansion medium with the same medium every $3^{rd}$ day during the expansion.

In certain embodiments, the mDAPs are contacted with an expansion medium for a total of about 6 days.

In certain embodiments, the expansion medium of the present disclosure is used as the above expansion medium. The expansion medium of the present disclosure used in the above embodiments has been described elsewhere herein (e.g., as described in the *Culture Medium for Expanding mDAPs* or the first aspect herein), and these same descriptions are omitted herein for purpose of simplification. According to the above embodiments, the expansion method can support long-term (such as at least 4, 5, 6 or more passages) expansion of mDAPs as a homogeneous population, or the expansion method, even if the mDAPs have been expanded and passaged for one or more times, can maintain or even improve the expansion efficiency and the expression of the mDAP-specific markers after the expansion and passaging than before the expansion and passaging.

In certain embodiments, the mDAPs have been expanded and passaged for at least 1, 2, 3, 4, 5, or 6 times (e.g., P1, P2, P3, P4, P5, P6 or later passages), preferably at least 4, 5, or 6 times (e.g., P4, P5, P6 or later passages), and most preferably at least 6 times (e.g., P6 or later passages).

In certain embodiments, the mDAPs are seeded on the culture surface at a density of about $1\times10^3$ cells/cm² to about $1\times10^5$ cells/cm². As compared with a higher seeding density, such low seeding density is beneficial for improving the expansion fold of plated cells.

In certain embodiments, the expansion method supports expansion of mDAPs: (1) with a population doubling time (PDT) of between about 25-28 hours and/or (2) with a total cell expansion folds of about 35-40 for imDAP cells which have been expanded and passaged for at least 1, 2, 3, 4, 5, 6, or more times (e.g., P1-P6).

In certain embodiments, the expansion method of the present disclosure can provide the expansion fold of at least 36 fold, 38-fold, 40-fold or more for each passage of mDAPs, which is at least 1.8 1.9, 2, or more times as high as that of the previous expansion method, for example, the method with VTN (about 20 folds).

Representative example of mDAP-specific markers is FOXA2. Representative example of mDAP-specific markers comprises FOXA2, and one or more selected from LMX1A, EN1, OTX2, and SOX6. In some embodiments, mDAP-specific markers comprise FOXA2, LMX1A, EN1, OTX2, and SOX6.

4. Culture Medium for Maturing mDAPs

In a fourth aspect, the present disclosure provides a culture medium (e.g., chemically defined serum-free maturation medium) that is capable of promoting the maturation of mDAPs (midbrain Dopaminergic Progenitor cells), said culture medium comprising: (a) a neural basal medium; (b) a human Platelet Lysate (hPLT); (c) a Transforming Growth Factor β (TGF-β); (d) a γ-secretase inhibitor; and (e) a cAMP-based compound or its cyclase activator.

B27 is commonly used as a medium supplement for neuron maturation in the prior arts. According to the fourth aspect, by replacing B27 with hPLT, the above maturation medium can improve the maturity (the percentage of TH+ cells) for the mDAPs.

According to the fourth aspect, the maturation medium of the present disclosure may be contacted with the mDAPs on a cell culture surface coated with any common maturation coating matrix in the art or any other suitable maturation coating matrix. Examples of common maturation coating matrix comprise vitronectin (VTN), and Laminin/poly-L-ornithine (PLO).

Any mDAPs may be matured using the maturation medium of the present disclosure. Examples of mDAPs comprise fetal brain-derived mDAPs; hPSC-derived mDAPs; and mDAPs obtained via transdifferentiation from other cell types. The mDAPs may be derived (e.g., differentiated) from pluripotent stem cells. Pluripotent stems cells can comprise induced pluripotent stem cells (e.g. hiPSCs), embryonic stem cells (e.g., hESCs), naïve PSCs (NPSCs) and extended pluripotent stem cells (EPSCs). In certain embodiments, the mDAPs are ESC-derived midbrain Dopaminergic Progenitor cells (emDAPs). In certain embodiments, the mDAPs are iPSC-derived midbrain Dopaminergic Progenitor cells (imDAPs). In certain embodiments, the mDAPs are NPSC-derived midbrain Dopaminergic Progenitor cells (nmDAPs). In certain embodiments, the mDAPs are EPSC-derived midbrain Dopaminergic Progenitor cells (epmDAPs).

In certain embodiments, the mDAPs are non-expanded mDAPs. In certain embodiments, the mDAPs are expanded mDAPs such as for example expanded imDAPs. In certain embodiments, the mDAPs are mDAPs which have been expanded and passaged for one or more times, such as for example expanded P1, P2, P3, P4, P5 or P6 imDAPs. In certain embodiments, the mDAPs are non-matured mDAPs. In certain embodiments, the mDAPs are partially matured mDAPs.

ESCs (e.g., hESCs) and iPSCs (e.g., hiPSCs) are known in the art and can be readily obtained using conventional methods, for example, those described in the existing technologies, or commercially available products. For example, CytoTune iPS 2.0 Sendai Reprogramming Kit (ThermoFisher Scientific) can be used to reliably generate induced pluripotent stem cells (iPSCs) from somatic cells, including PBMCs and T-cells.

Such iPSCs (e.g., hiPSCs) can be cultured under defined conditions to generate mDAPs. For example, iPSCs (e.g., hiPSCs) can be cultured on Matrigel under defined conditions in mTeSR™ medium (Stemcell Technologies, Cat. #85850), and subconfluent hiPSCs are passaged onto fresh Matrigel-coated plates and cultured for additional time (e.g., 24 hours) in iPSC medium to reach 90-100% confluency. Once confluent, the medium can be changed to induce mDAPs for a further period (such as 1-3 days), with optional daily medium change as necessary. e.g., Fedele et al., *Scientific Reports* 7: 6036| DOI:10.1038/s41598-017-05633-1 (2017, incorporated by reference).

As implied by the name, the Neural basal medium can support the survival, maintenance, growth, and proliferation of neural cells as a medium, and is a basal component for the maturation medium. Generally, the Neural basal medium comprises about 95% to 99% by volume of the maturation medium.

Examples of the Neural basal medium comprises NEUROBASAL™ basal medium (e.g., Gibco Cat. #21103049), NEUROBASAL-A™ basal medium (e.g., Gibco Cat. #10888022), NEUROBASAL PLUS™ basal medium (e.g., Gibco Cat. #A3582901), and/or BRAINPHYS™ basal medium (e.g., STEMCELL Cat. #05790). hPLT is commercially available, e.g., PLTGold Human Platelet Lysate (Biological Industries, #PLTGOLD500R). However, hPLT from other sources are also available and can be used with the present disclosure.

According to the present disclosure, the concentration of the hPLT is not particularly limited as long as it does not impede the promotion of the maturation of mDAPs. In certain embodiments, the hPLT is present in the culture medium at a concentration of about 0.1% to about 5% by volume, and preferably about 0.1% to about 2% by volume.

In certain embodiments, the TGF-β comprises TGF-01 (e.g., APExBio Cat. #P1039; MCE Cat. #HY-P78168), TGF-β 2 (e.g., R&D Cat. #302-B2), TGF-03 (e.g., Peprotech Cat. #100-36E), and/or TGF-β1β2.

According to the present disclosure, the concentration of the TGF-β is not particularly limited as long as it does not impede the promotion of the maturation of mDAPs. In certain embodiments, the TGF-β (such as TGF-03) is present in the culture medium at a concentration of about 0.1 ng/ml to about 10 ng/ml, preferably about 0.5 ng/mL to about 5 ng/mL, and more preferably about 1 ng/mL to about 2 ng/mL.

In certain embodiments, the γ-secretase inhibitor comprises, or is selected from the group consisting of DAPT, N-[N-(3,5-difluorophenacetyl)]-L-alanyl-3-(S)-amino-1-methyl-5-phenyl-1,3-dihydro-benzo[E](1,4)diazepin-2-one, LY-411575, Dihydroergocristine mesylate, BMS 299897, and any combination thereof.

Representative structures of certain γ-secretase inhibitors that may be used in the medium of the present disclosure are provided below, many of which are widely commercially available from multiple sources, with indicated Cat. No. from such selected commercial sources (though such sources are not limiting).

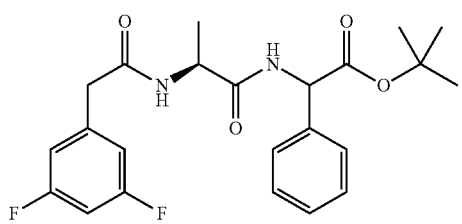 [SMILES: C[C@H](NC(=O)Cc1cc(F)cc(F)c1)C(=O)NC(C(=O)OC(C)(C)C)c1ccccc1]

DAPT (MCE Cat. #HY-13027, CAS No.: 208255-80-5).

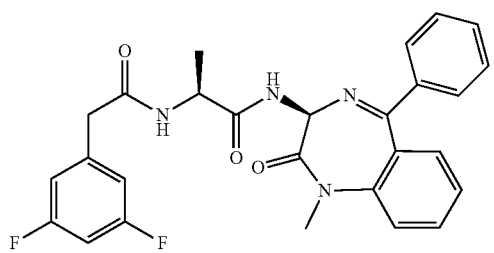 [SMILES: C[C@H](NC(=O)Cc1cc(F)cc(F)c1)C(=O)N[C@H]1N=C(c2ccccc2)c2ccccc2N(C)C1=O]

compound E (N-[N-(3,5-difluorophenacetyl)]-L-alanyl-3-(S)-amino-1-methyl-5-phenyl-1,3-dihydro-benzo[E](1,4)diazepin-2-one) (APExBio Cat. #C3341; MCE Cat. #HY-14176; CAS No.: 209986-17-4).

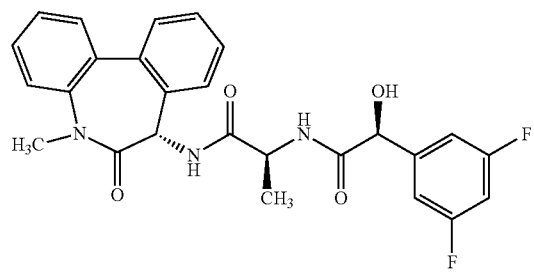 [SMILES: C[C@H](NC(=O)[C@@H](O)c1cc(F)cc(F)c1)C(=O)N[C@@H]1C(=O)N(C)c2ccccc2-c2ccccc21]

LY-411575 (Sigma-Aldrich Cat. #SML0506; APExBio Cat. #A4019, MCE Cat. #HY-50752; CAS No.: 209984-57-6).

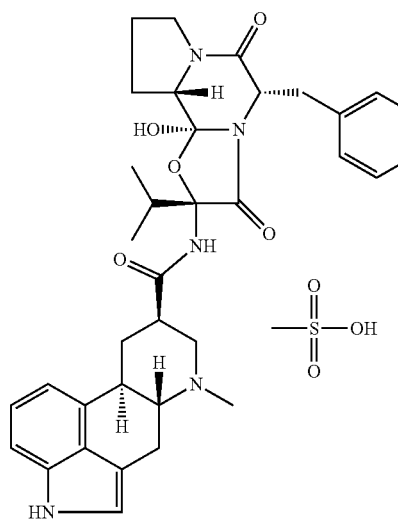

Dihydroergocristine mesylate (APExBio Cat. #B6313; MCE Cat. #HY-N2319; CAS No.: 24730-10-7).

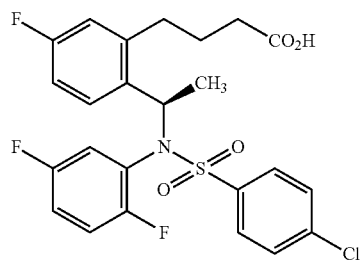 [SMILES: C[C@H](c1ccc(F)cc1CCCC(=O)O)N(c1cc(F)ccc1F)S(=O)(=O)c1ccc(Cl)cc1]

BMS 299897 (Sigma-Aldrich Cat. #SML0210; APExBio Cat. #A4400; MCE Cat. #HY-50883; CAS No.: 290315-45-6).

In certain embodiments, the γ-secretase inhibitor comprises DAPT.

According to the present disclosure, the concentration of the γ-secretase inhibitor is not particularly limited as long as it does not impede the promotion of the maturation of mDAPs. In certain embodiments, the γ-secretase inhibitor (e.g., DAPT) is present in the maturation medium at about 1 μM to about 30 μM, and preferably about 5 μM to about 20 μM.

As used herein, the cAMP-based compound is a cell permeable cAMP-like compound that directly increases the content of intracellular cAMP. In certain embodiments, the cAMP-based compound comprises cAMP, or a derivative thereof or a salt thereof. The examples of the derivative of cAMP or the salt thereof comprise Db-cAMP sodium salt, 8-bromo-cAMP sodium salt, 8-Chloro-cAMP, 6-Bnz-cAMP sodium salt, and Bucladesine calcium salt (Dibutyryl cAMP calcium salt). In addition, the cyclase activator of the cAMP-based compound may be also used in the maturation medium of the present disclosure to generate intracellular c-AMP. The examples of the cyclase activator comprise forskolin and NKH477.

In certain embodiments, the cAMP-based compound or its cyclase activator comprises, or is selected from the group consisting of Db-cAMP sodium salt, cAMP, forskolin, 8-bromo-cAMP sodium salt, NKH477, 8-Chloro-cAMP, 6-Bnz-cAMP sodium salt, Bucladesine calcium salt, and any combination thereof.

Representative structures of certain cAMP-based compounds or cyclase activators thereof that may be used in the maturation medium of the present disclosure are provided below, many of which are widely commercially available from multiple sources, with indicated Cat. No. from such selected commercial sources (though such sources are not limiting).

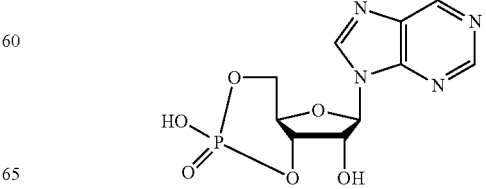

cAMP (Sigma-Aldrich Cat. #20-198; MCE Cat. #HY-B1511, CAS No.: 60-92-4).

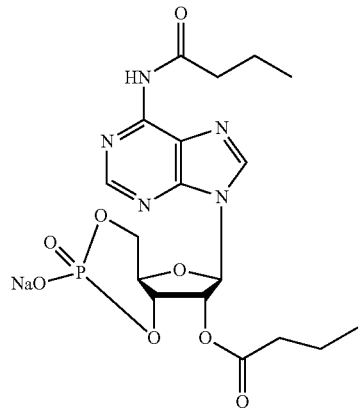

Db-cAMP sodium salt (Sigma Cat. #D0627, CAS No. 16980-89-5)

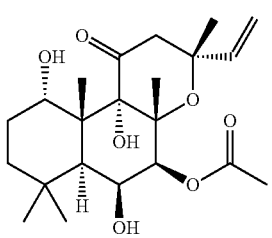

Forskolin (MCE Cat. #HY-15371; CAS No.: 66575-29-9).

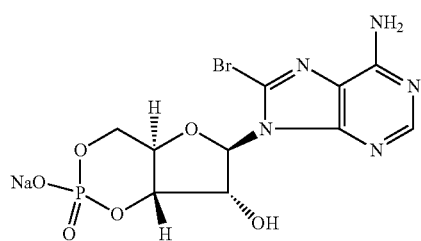

8-bromo-cAMP sodium salt (Sigma-Aldrich Cat. #B7880; APExBio Cat. #B9000; MCE Cat. #HY-12306; CAS No.: 76939-46-3).

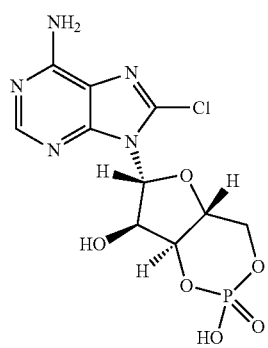 [SMILES: Nc1ncnc2c1nc(Cl)n2[C@@H]1O[C@@H]2COP(=O)(O)O[C@H]2[C@H]1O]

8-Chloro-cAMP (MCE Cat. #HY-123396; CAS No.: 41941-56-4).

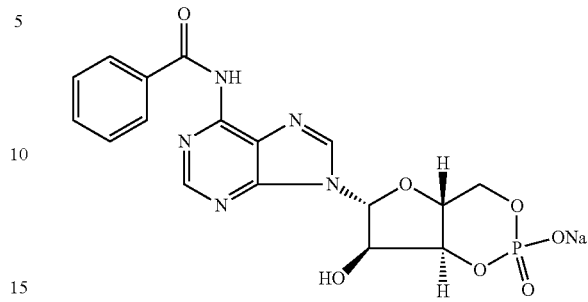

6-Bnz-cAMP sodium salt (MCE Cat. #HY-103322; CAS No.: 1135306-29-4).

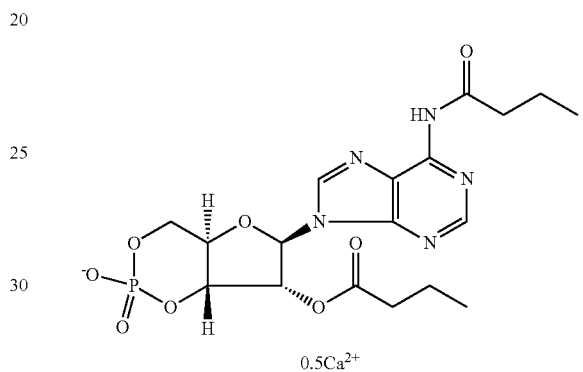

Bucladesine calcium salt (MCE Cat. #HY-B0764A; CAS No.: 938448-87-4).

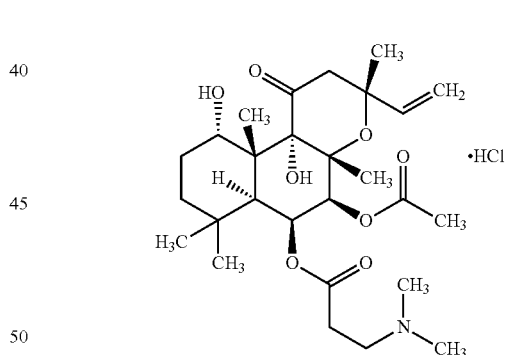

NKH477 (Sigma-Aldrich Cat. #N3290; MCE Cat. #HY-103193; CAS No.: 138605-00-2).

In certain embodiments, the cAMP-based compound or its cyclase activator comprises Db-cAMP sodium salt.

In certain embodiments, the cAMP-based compound (e.g., Db-cAMP sodium salt) or its cyclase activator is present in the culture medium at a concentration of about 0.1 mM to about 5 mM, and preferably about 0.1 mM to about 2 mM.

Optionally, the culture medium may comprise (f) a neurotrophic factor. The neurotrophic factor comprises a ligand for a membrane receptor that promotes in survival and functional maintenance of neurons.

In certain embodiments, the neurotrophic factor comprises Nerve Growth Factor (NGF, e.g., Sigma-Aldrich Cat.

N8898; MCE Cat. (Beta-NGF) #HY-P72488/HY-P3316/HY-P70449), Brain-derived Neurotrophic Factor (BDNF), Neurotrophin 6 (NT-6), Glia cell line-derived Neurotrophic Factor (GDNF), Ciliary Neurotrophic Factor (CNTF, e.g., Sigma-Aldrich Cat. #01-195; MCE Cat. (Beta-NGF) #HY-P7146/HY-P7145/HY-P72943), and/or Insulin Like Growth Factor 2 (IGF2, e.g., APExBio Cat. #P1017; MCE Cat. No. #HY-P7019).

In certain embodiments, the neurotrophic factor comprises, or is selected from the group consisting of BDNF, GDNF, and both.

According to the present disclosure, the concentration of the neurotrophic factor is not particularly limited as long as it does not impede the promotion of the maturation of mDAPs. In certain embodiments, the neurotrophic factor is present in the culture medium at a concentration of about 1 ng/ml to about 100 ng/ml, preferably about 5 ng/ml to about 80 ng/ml, and more preferably about 10 ng/ml to about 50 ng/ml.

In certain embodiments, BNDF is present in the maturation medium at about 1 ng/mL to about 100 ng/mL, about 5 ng/ml to about 80 ng/ml, or about 10 ng/mL to about 50 ng/mL. In certain embodiments, GDNF is present in the maturation medium at about 1 ng/mL to about 100 ng/mL, about 5 ng/ml to about 80 ng/ml, or about 10 ng/mL to about 50 ng/mL.

In certain embodiments, the culture medium further comprises (g) a Rho Kinase (ROCK) inhibitor.

The ROCK inhibitor comprises an agent which inhibits binding between ROCK and a ROCK receptor.

In certain embodiments, the ROCK inhibitor comprises or is selected from the group consisting of: Y27632, HA100, HA1152, HA-1077, and any combination thereof.

Y-27632 is also known as (R)-(+)-trans-4-(1-aminoethyl)-N-(4-pyridyl) cyclohexanecarboxamide dihydrochloride (e.g., Sigma-Aldrich). HA100 is also known as 5-(1-piperazinylsulfonyl)-isoquinoline, dihydrochloride. HA1077 is also known as fasudil hydrochloride or 5-(1,4-diazepan-1-ylsulfonyl)isoquinoline hydrochloride (Cayman Chemical). H-1152 is also known as (S)-(+)-2-methyl-1-[(4-methyl-5-isoquinolinyl) sulfonyl]-hexahydro-1H-1,4-diazepine dihydrochloride (Tocris Bioscience). Other ROCK inhibitors include N-(6-fluoro-1H-indazol-5-yl)-2-methyl-6-oxo-4-(4-(trifluoromethyl)phenyl)-1,4,5,6-tetrahydropyridine-3-carboxamide (GSK429286A, Stemgent).

Representative structures of certain ROCK inhibitors that may be used in the maturation medium of the present disclosure are provided below, many of which are widely commercially available from multiple sources, with indicated Cat. No. from such selected commercial sources (though such sources are not limiting).

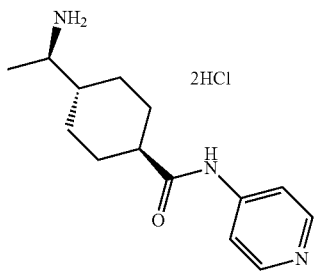 [SMILES: C[C@@H](N)[C@H]1CC[C@H](C(=O)Nc2ccncc2)CC1]

Y-27632 (MCE Cat. #HY-10071, CAS No.: 146986-50-7).

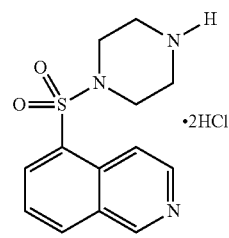 [SMILES: O=S(=O)(c1cccc2cnccc12)N1CCNCC1]

HA-100 (hydrochloride) (absin Cat. #abs47045575).

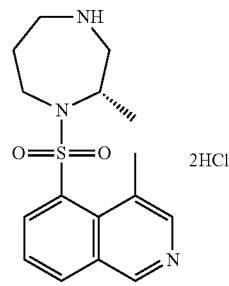 [SMILES: Cc1cncc2cccc(S(=O)(=O)N3CCCNC[C@@H]3C)c12]

H1152 (MCE Cat. #HY-15720, CAS No.: 451462-58-1).

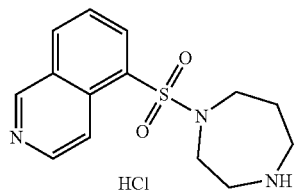 [SMILES: O=S(=O)(c1cccc2cnccc12)N1CCCNCC1 ; Cl]

HA-1077 (Fasudil/AT877) (MCE Cat. #HY-10341A, CAS No.: 103745-39-7).

In certain embodiments, the ROCK inhibitor comprises Y27632. In certain embodiments, the ROCK inhibitor (e.g., Y27632) is present in the maturation medium at about 1 μM to about 50 μM, preferably about 1 μM to about 20 μM, or more preferably about 5 μM to about 15 μM.

In certain embodiments, the hPLT is a heat-treated human Platelet Lysate (HhPLT). According to the above embodiments, the HhPLT can further improve the maturity for the mDAPs as compared with hPLT. While not wishing to be bound by any particular theory, it is believed that HhPLT can reduce batch to batch difference as compared with hPLT.

According to the present disclosure, the HhPLT may be produced by performing the heat treatment to hPLT. In certain embodiments, the HhPLT is produced by firstly centrifuging hPLT, heating the hPLT at about 45-60° C. and then centrifuging the hPLT. In certain embodiments, the hPLT is centrifuged at 3000 g for 30 min at 4° C. to obtain the supernatant, it is heated to 56° C. for 30 min, the suspension is finally cooled down to 4° C. at least 5 min, and spun at 3000 g for 30 min at 4° C., and aliquots are prepared and stored at −80° C. until use.

According to the present disclosure, the concentration of the HhPLT is not particularly limited as long as it does not impede the promotion of the maturation of mDAPs. In certain embodiments, the HhPLT is present in the culture medium at a concentration of about 0.1% to about 5% by volume, and preferably about 0.1% to about 2% by volume.

In certain embodiments, the maturation medium of the present disclosure further comprises (h) a WNT signaling pathway inhibitor. According to the above embodiments, the culture medium can further improve the maturity for the mDAPs as compared with the medium without a WNT signaling pathway inhibitor.

As used herein, a Wnt signaling pathway inhibitor refers to antagonist of the Wnt signaling pathway (e.g., agents capable of downregulating activity and/or amount of a component participating in the Wnt signaling pathway) and can be interchanged with a "Wnt signaling pathway antagonist," "Wnt antagonist," "Wnt pathway inhibitor," or "Wnt inhibitor". Wnt signaling pathway inhibitors can include, for example, an agent that antagonizes one or more human FZD proteins, an FZD-binding agent. The FZD-binding agent may be an antibody or a polypeptide.

Examples of Wnt signaling pathway inhibitors include, without limitation, one or more of the following: a polypeptide comprising an amino acid sequence of a Wnt antagonist, a small organic molecule that inhibits Wnt/β-catenin signaling, a small organic molecule that inhibits the expression or activity of a Wnt agonist, an antibody that binds to and inhibits the activity of a Wnt agonist and preferably a small organic molecule that inhibits Wnt/β-catenin signaling, and a small organic molecule that inhibits the expression or activity of a Wnt agonist.

In certain embodiments, the WNT signaling pathway inhibitor comprises, or is selected from the group consisting of IWR1, iCRT3, IWP-O1, IWP-2, IWP-3, IWP-4, Ciclopirox, Cardamonin, Diethyl benzylphosphonate, Disodium Pamidronate Hydrate, Ginsenoside Rh4, KY-05009, XAV-939, Foscenvivint (ICG-001), Capmatinib, Isoquercitrin, Gigantol, JW55, MSAB, KY02111, FH535, WIKI4, CCT251545, Prodigiosin, KYA1797K, NCB-0846, LF3, iCRT14, Adavivint, Triptonide, M435-1279, and any combination thereof.

Representative structures of certain WNT signaling pathway inhibitors that may be used in the maturation medium of the present disclosure are provided below, many of which are widely commercially available from multiple sources, with indicated Cat. No. from such selected commercial sources (though such sources are not limiting).

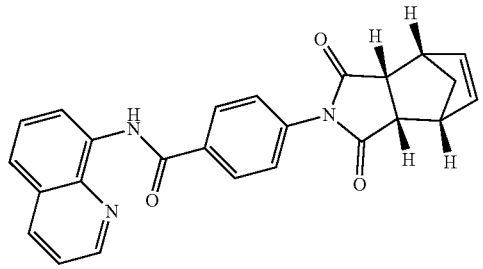 [SMILES: O=C(Nc1cccc2cccnc12)c1ccc(N2C(=O)[C@@H]3[C@H](C2=O)[C@@H]2C=C[C@H]3C2)cc1]

IWR1 (MCE Cat. #HY-12238, CAS No.: 1127442-82-3).

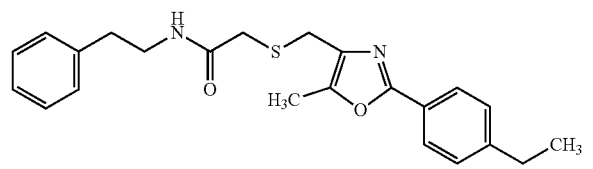 [SMILES: CCc1ccc(-c2nc(CSCC(=O)NCCc3ccccc3)c(C)o2)cc1]

iCRT3 (Sigma-Aldrich Cat. #SML2111/219332; MCE Cat.L #HY-103705; CAS No.: 901751-47-1).

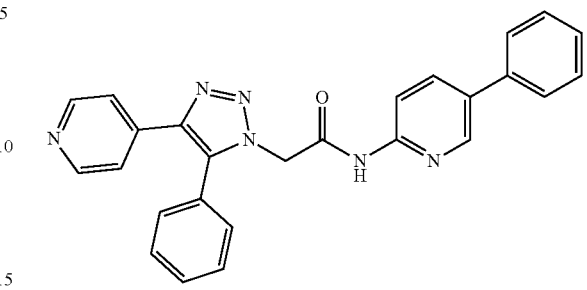

IWP-O1 (Sigma-Aldrich Cat. #SML1962; MCE Cat. #HY-100853; CAS No.: 2074607-48-8).

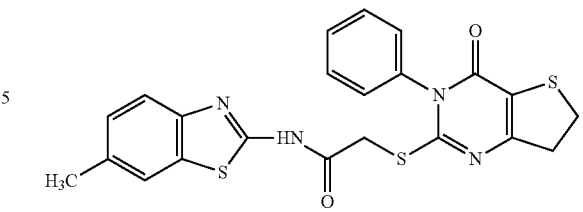

IWP-2 (Sigma-Aldrich Cat. #I0536; APExBio Cat. #A3512; CAS No.: 686770-61-6).

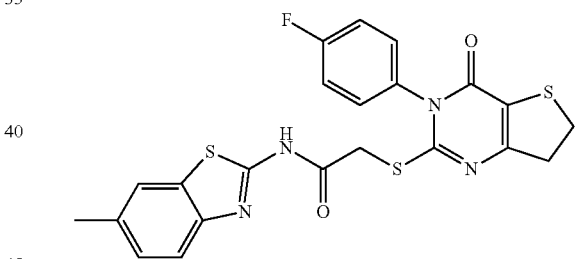

IWP-3 (APExBio Cat. #C3254; MCE Cat. #HY-100536; CAS No.: 687561-60-0).

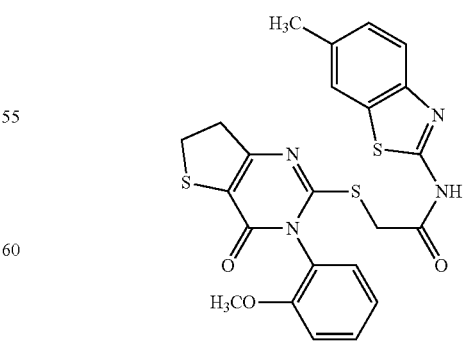

IWP-4 (Sigma-Aldrich Cat. #SML1114; APExBio Cat. #B4922; CAS No.: 686772-17-8).

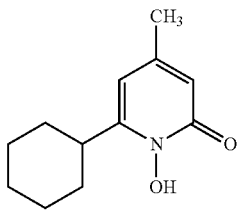

Ciclopirox (Sigma-Aldrich Cat. #SML2011; APExBio Cat. #B2087; MCE Cat. #HY-B0450; CAS No.: 29342-05-0).

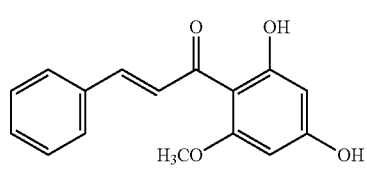 [SMILES: COc1cc(O)cc(O)c1C(=O)/C=C/c1ccccc1]

Cardamonin (Sigma-Aldrich Cat. #C8249; APExBio Cat. #B7085; MCE Cat. #HY-N0279; CAS No.: 18956-16-6).

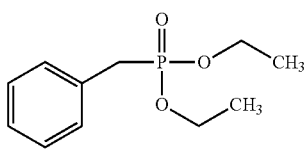

Diethyl benzylphosphonate (Sigma-Aldrich Cat. #D91071; CAS No.: 1080-32-6).

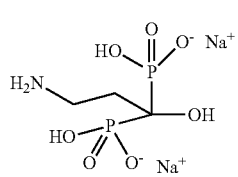 [SMILES: NCCC(O)(P(=O)([O-])O)P(=O)([O-])O ; [Na+] ; [Na+]]

Disodium Pamidronate Hydrate (Sigma-Aldrich Cat. #P2371; APExBio Cat. #A2456; MCE Cat. #HY-B0012A; CAS No.: 57248-88-1

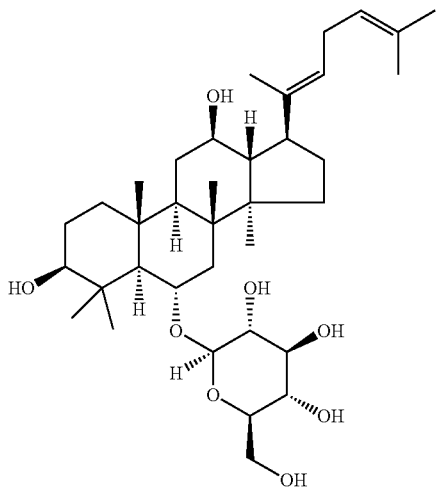

Ginsenoside Rh4 (LeiMeiTian Medicine Cat. #DR0020; CAS No.: 174721-08-5).

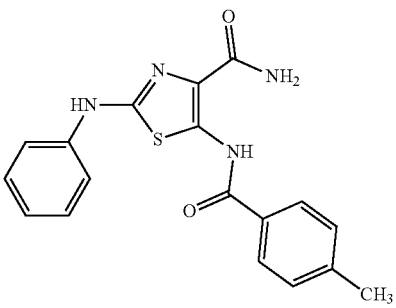 [SMILES: Cc1ccc(C(=O)Nc2sc(Nc3ccccc3)nc2C(N)=O)cc1]

KY-05009 (Sigma-Aldrich Cat. #SML1506; MCE Cat. #HY-05009; CAS No.: 1228280-29-2).

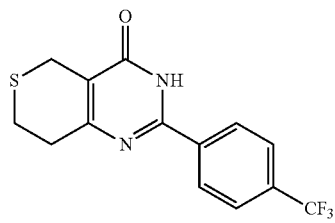 [SMILES: O=c1[nH]c(-c2ccc(C(F)(F)F)cc2)nc2c1CSCC2]

XAV-939 (Sigma-Aldrich Cat. #X3004; APExBio Cat. #A1877; MCE Cat. #HY-14428; CAS No.: 780757-88-2).

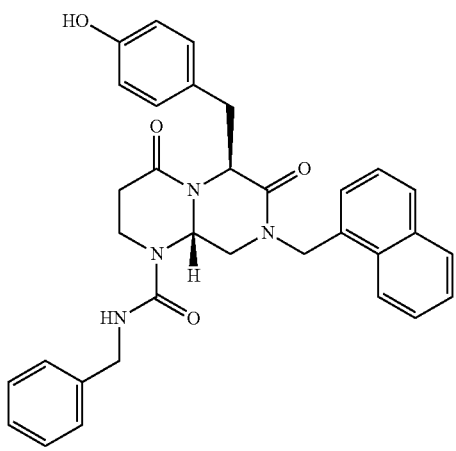 [SMILES: O=C1[C@H](Cc2ccc(O)cc2)N2C(=O)CCN(C(=O)NCc3ccccc3)[C@H]2CN1Cc1cccc2ccccc12]

Foscenvivint (ICG-001) (APExBio Cat. #A8217; MCE Cat. #HY-15147; CAS No.: 284028-89-3).

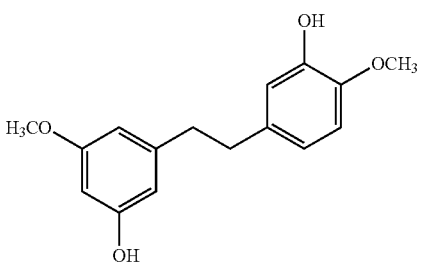 [SMILES: COc1cc(O)cc(CCc2ccc(OC)c(O)c2)c1]

Gigantol (Sigma-Aldrich, #SML2036; MCE Cat. #HY-N2523; CAS No.: 67884-30-4).

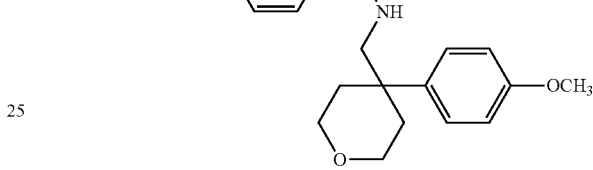

JW55 (Sigma-Aldrich Cat. #SML0630; APExBio Cat. #A4529; MCE Cat. #HY-13968; CAS No.: 664993-53-7).

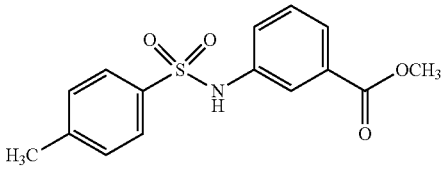 [SMILES: COC(=O)c1cccc(NS(=O)(=O)c2ccc(C)cc2)c1]

MSAB (Sigma-Aldrich Cat. #SML1726; MCE Cat. #HY-120697; CAS No.: 173436-66-3).

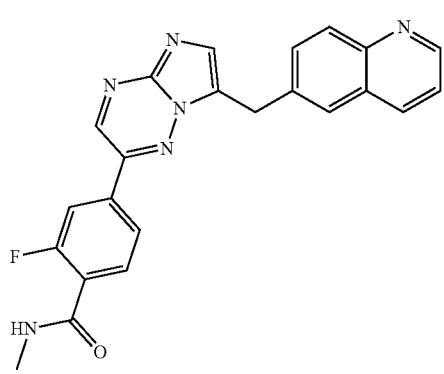

Capmatinib (MCE Cat. #HY-13404; CAS No.: 1029712-80-8).

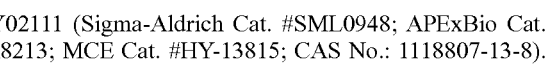

KY02111 (Sigma-Aldrich Cat. #SML0948; APExBio Cat. #A8213; MCE Cat. #HY-13815; CAS No.: 1118807-13-8).

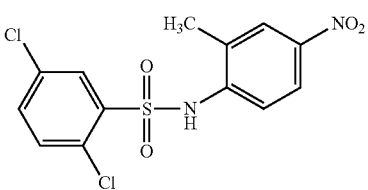 [SMILES: Cc1cc([N+](=O)[O-])ccc1NS(=O)(=O)c1cc(Cl)ccc1Cl]

FH535 (Sigma-Aldrich Cat. #F5682; APExBio Cat. #A3413; MCE Cat. #HY-15721; CAS No.: 108409-83-2).

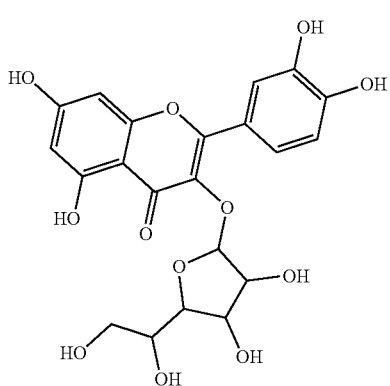

Isoquercitrin (APExBio Cat. #N1945; MCE Cat. #HY-N0768; CAS No.: 21637-25-2).

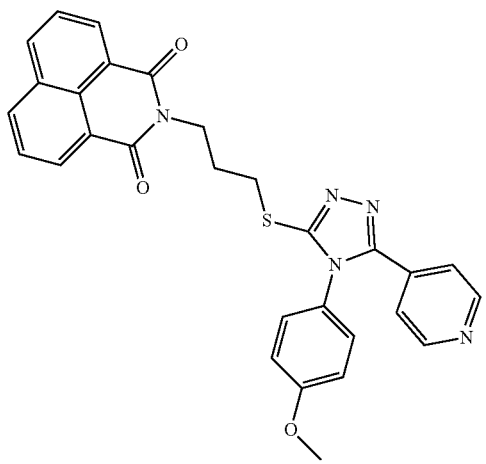 [SMILES: COc1ccc(-n2c(SCCCN3C(=O)c4cccc5cccc(c45)C3=O)nnc2-c2ccncc2)cc1]
WIKI4 (APExBio Cat. #A3413; MCE Cat. #HY-16910; CAS No.: 838818-26-1).
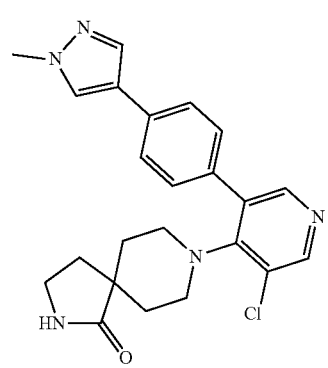 [SMILES: Cn1cc(-c2ccc(-c3cncc(Cl)c3N3CCC4(CCNC4=O)CC3)cc2)cn1]
CCT251545 (APExBio Cat. #A5979; MCE Cat. #HY-12681; CAS No: 166183-9-45-7).
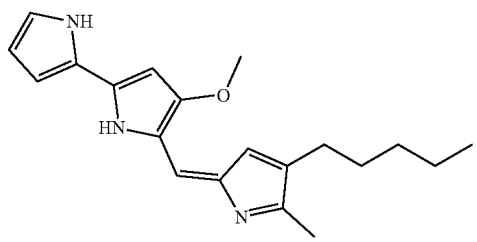 [SMILES: CCCCCC1=C/C(=C\c2[nH]c(-c3ccc[nH]3)cc2OC)N=C1C]
Prodigiosin (APExBio Cat. #C3112; MCE Cat. #HY-100711; CAS No.: 108409-83-2).
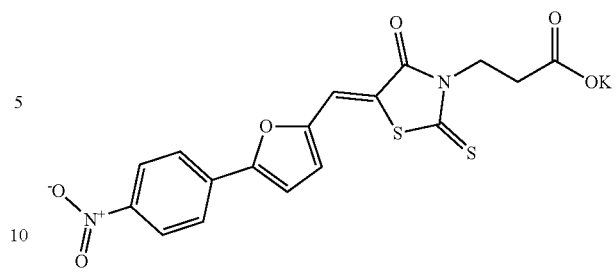
KYA1797K (Sigma-Aldrich Cat. #SML1831; MCE Cat. #HY-101090; CAS No.: 1956356-56-1).
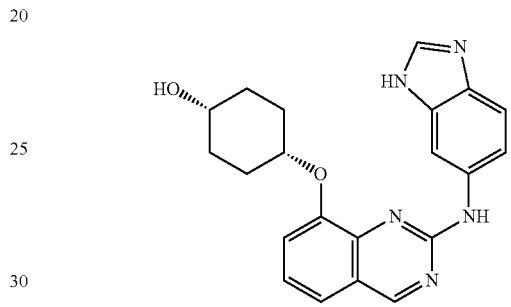
N NCB-0846 (MCE Cat. #HY-100830; CAS No.: 1792999-26-8).
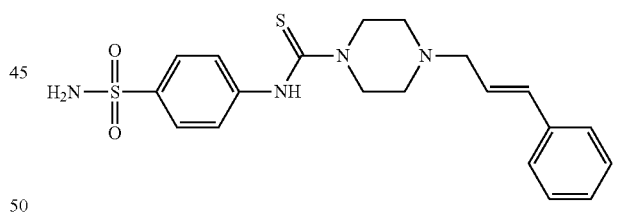
LF3 (Sigma-Aldrich Cat. #SML1752; MCE Cat. #HY-101486; CAS No.: 1956356-56-1).
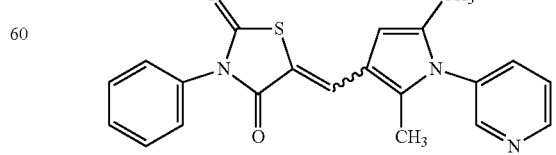
iCRT14 (TOCRIS(R&D) Cat. #677331-12-3).

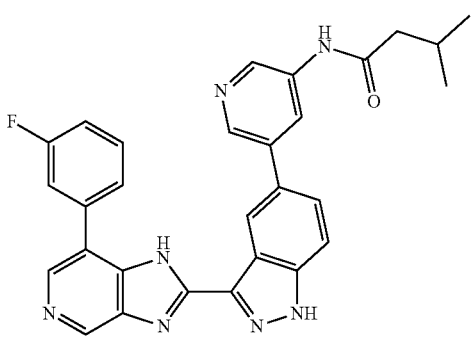 [SMILES: CC(C)CC(=O)Nc1cncc(-c2ccc3[nH]nc(-c4nc5cncc(-c6cccc(F)c6)c5[nH]4)c3c2)c1]

Adavivint (MCE Cat. #HY-109049; CAS No.: 1467093-03-3).

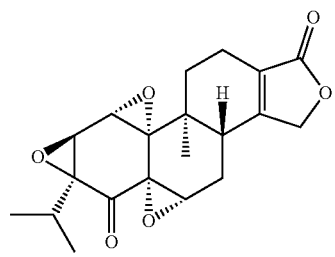

Triptonide (Sigma-Aldrich Cat. #SMB00325; APExBio Cat. #A3892; MCE Cat. #HY-32736; CAS No.: 38647-11-9).

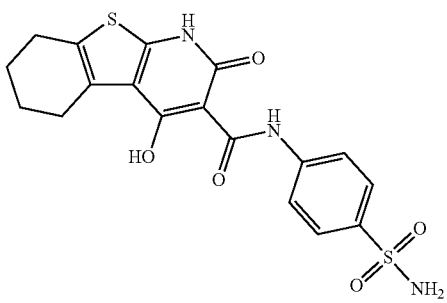 [SMILES: NS(=O)(=O)c1ccc(NC(=O)c2c(O)c3c4c(sc3[nH]c2=O)CCCC4)cc1]

M435-1279 (MCE Cat. #HY-141891; CAS No.: 1359431-16-5).

In certain embodiments, the Wnt signaling pathway inhibitor comprises IWR1.

In certain embodiments, the Wnt signaling pathway inhibitor (e.g., IWR1) is present in the maturation medium at about 0.25 µM to about 10 µM, and preferably about 0.5 µM to about 5 µM.

In certain embodiments, the maturation culture medium of the present disclosure comprises: (a) about 0.1% to about 2% by volume of the hPLT or HhPLT; (b) about 0.1 ng/mL to about 5 ng/mL of the TGF-β; (d) about 5 µM to about 20 µM of the γ-secretase inhibitor; (d) about 0.1 mM to about 2.5 mM of the cAMP-based compound or its cyclase activator; and (e) about 10 ng/ml to about 80 ng/ml of the neurotrophic factor, in the neural basal medium.

In certain embodiments, the maturation culture medium of the present disclosure comprises: (a) about 0.1% to about 2% by volume of the hPLT or HhPLT; (b) about 0.1 ng/mL to about 5 ng/mL of the TGF-β; (d) about 5 µM to about 20 µM of the γ-secretase inhibitor; (d) about 0.1 mM to about 2.5 mM of the cAMP-based compound or its cyclase activator; (e) about 10 ng/ml to about 80 ng/ml of the neurotrophic factor; and (f) about 5 µM to about 15 µM of a ROCK inhibitor, in the neural basal medium.

In certain embodiments, the maturation culture medium of the present disclosure comprises: (a) about 0.1% to about 2% by volume of the hPLT or HhPLT; (b) about 0.1 ng/mL to about 5 ng/mL of the TGF-β; (d) about 5 µM to about 20 µM of the γ-secretase inhibitor; (d) about 0.1 mM to about 2.5 mM of the cAMP-based compound or its cyclase activator; (e) about 10 ng/ml to about 80 ng/ml of the neurotrophic factor; (f) about 5 µM to about 15 µM of a ROCK inhibitor; and (g) about 0.5 µM to about 5 µM of a WNT signaling pathway inhibitor, in the neural basal medium.

In certain embodiments, the maturation culture medium of the present disclosure comprises: (a) about 0.1% to about 2% by volume of the hPLT or HhPLT; (b) about 0.1 ng/mL to about 5 ng/mL of the TGF-β; (c) about 5 µM to about 20 µM of DAPT; (d) about 0.1 mM to about 2.5 mM of Db-cAMP sodium salt; and, (e) about 10 ng/ml to about 80 ng/ml of the combination of BDNF and GDNF, in the neural basal medium.

In certain embodiments, the maturation culture medium of the present disclosure comprises: (a) about 0.1% to about 2% by volume of the hPLT or HhPLT; (b) about 0.1 ng/mL to about 5 ng/mL of the TGF-β; (c) about 5 µM to about 20 µM of DAPT; (d) about 0.1 mM to about 2.5 mM of Db-cAMP sodium salt; (e) about 10 ng/ml to about 80 ng/ml of the combination of BDNF and GDNF; and (f) about 5 µM to about 15 µM of Y27632, in the neural basal medium.

In certain embodiments, the maturation culture medium of the present disclosure comprises: (a) about 0.1% to about 2% by volume of the hPLT or HhPLT; (b) about 0.1 ng/mL to about 5 ng/mL of the TGF-β; (c) about 5 µM to about 20 µM of DAPT; (d) about 0.1 mM to about 2.5 mM of Db-cAMP sodium salt; (e) about 10 ng/ml to about 80 ng/ml of the combination of BDNF and GDNF; (f) about 5 µM to about 15 µM of Y27632; and (g) about 0.5 µM to about 5 µM of IWR1, in the neural basal medium.

In certain embodiments, the maturation medium of the present disclosure may optionally further comprise a glutamine or its derivative.

In certain embodiments, the glutamine or its derivative comprises L-alanyl-L-glutamine dipeptide (e.g., GLUTAMAX™ brand L-alanyl-L-glutamine dipeptide, Gibco Cat. #35050061), L-Glutamine (e.g., Sigma-Aldrich Cat. #G2150/G7513; APExBio Cat. #A8461; MCE Cat. #HY-N0390; CAS No.: 56-85-9), or a mixture thereof.

In certain embodiments, the glutamine or its derivative is present in the maturation medium of the present disclosure at a concentration of about 0.5% to 5% by volume, and preferably about 0.5% to 2.5% by volume.

In certain embodiments, the maturation medium of the present disclosure may optionally further comprise an antioxidant.

In certain embodiments, the antioxidant comprises ascorbic acid (e.g., Sigma Cat. #A8960) or its salt (e.g., Na salt, Mg salt) or its derivative, SOD (e.g., Sigma Cat. #S7571, S9697, S5395, S8160, S9636, 58409, S7446, CAS No.: 9054-89-1), or a mixture thereof.

In certain embodiments, the antioxidant (e.g, ascorbic acid) is present in the maturation medium of the present disclosure at a concentration of about 50 µM to about 500 µM, preferably about 100 µM to about 400 µM, and more preferably about 100 µM to about 300 µM.

In certain embodiments, the maturation medium can improve the expression of TH. In certain embodiments, the maturation medium can improve the expressions of TH and one or more selected from LMX1A, EN1, OTX2, FOX2, NURR1 and SOX6. In certain embodiments, the maturation medium can improve the expressions of TH, LMX1A, EN1, OTX2, FOX2, NURR1 and SOX6.

5. Method for Maturing mDAPs

In a fifth aspect, the present disclosure provides a method for promoting the maturation of midbrain Dopaminergic Progenitor cells (mDAPs), comprising contacting the mDAPs with a ROCK inhibitor-containing maturation medium on a culture surface coated with a coating matrix combination comprising: (a) a first coating matrix that can support cell adhesion for the mDAPs, wherein the first coating matrix is not laminin; and, (b) a second coating matrix that can improve the maturity for the mDAPs, wherein the second coating matrix comprises a polylysine (PL)-based compound and/or a polyornithine (PO)-based compound.

The existing maturation method generally uses the combination of Laminin/PLO as a matrix for mDA neuron maturation, but the cost is too high for large-scale mDA neuron production. According to the fifth aspect, by using the ROCK inhibitor in conjunction with the first coating matrix and the second coating matrix, the above maturation method can improve the maturity (the percentage of TH+ cells) for the mDAPs while reducing the production cost. In addition, the maturation method of the present disclosure can achieve a comparable yield to the maturation method using Laminin/PLO. Therefore, the maturation method of the present disclosure is more applicable for large-scale mDA neuron production.

Any mDAPs may be matured using the maturation method of the present disclosure. Examples of mDAPs comprise fetal brain-derived mDAPs; hPSC-derived mDAPs; and mDAPs obtained via transdifferentiation from other cell types. The mDAPs may be derived (e.g., differentiated) from pluripotent stem cells. Pluripotent stems cells can comprise induced pluripotent stem cells (e.g. hiPSCs), embryonic stem cells (e.g., hESCs), naïve PSCs (NPSCs) and extended pluripotent stem cells (EPSCs). In certain embodiments, the mDAPs are ESC-derived midbrain Dopaminergic Progenitor cells (emDAPs). In certain embodiments, the mDAPs are iPSC-derived midbrain Dopaminergic Progenitor cells (imDAPs). In certain embodiments, the mDAPs are NPSC-derived midbrain Dopaminergic Progenitor cells (nmDAPs). In certain embodiments, the mDAPs are EPSC-derived midbrain Dopaminergic Progenitor cells (epmDAPs).

In certain embodiments, the mDAPs are non-expanded mDAPs. In certain embodiments, the mDAPs are expanded mDAPs such as for example expanded imDAPs. In certain embodiments, the mDAPs are mDAPs which have been expanded and passaged for one or more times, such as for example expanded P1, P2, P3, P4, P5 or P6 imDAPs. In certain embodiments, the mDAPs are non-matured mDAPs. In certain embodiments, the mDAPs are partially matured mDAPs.

ESCs (e.g., hESCs) and iPSCs (e.g., hiPSCs) are known in the art and can be readily obtained using conventional methods, for example, those described in the existing technologies, or commercially available products. For example, CytoTune iPS 2.0 Sendai Reprogramming Kit (ThermoFisher Scientific) can be used to reliably generate induced pluripotent stem cells (iPSCs) from somatic cells, including PBMCs and T-cells.

Such iPSCs (e.g., hiPSCs) can be cultured under defined conditions to generate mDAPs. For example, iPSCs (e.g., hiPSCs) can be cultured on Matrigel under defined conditions in mTeSR™ medium (Stemcell Technologies, Cat. #85850), and subconfluent hiPSCs are passaged onto fresh Matrigel-coated plates and cultured for additional time (e.g., 24 hours) in iPSC medium to reach 90-100% confluency. Once confluent, the medium can be changed to induce mDAPs for a further period (such as 1-3 days), with optional daily medium change as necessary. e.g., Fedele et al., *Scientific Reports* 7: 6036 DOI:10.1038/s41598-017-05633-1 (2017, incorporated by reference).

According to the present disclosure, the ROCK inhibitor-containing maturation medium is not particularly limited as long as this maturation medium contains a ROCK inhibitor. The above maturation medium may be obtained by adding a ROCK inhibitor into a common mDAP maturation medium in the art or any other suitable mDAP maturation medium. Examples of common mDAP maturation medium comprise Gibco™ PSC Dopaminergic Neuron Differentiation Kit and STEMdiff™ Dopaminergic Neuron Differentiation Kit/STEMdiff™ (#08530).

In certain embodiments, the maturation medium of the present disclosure is used as the ROCK inhibitor-containing maturation medium. The maturation medium of the present disclosure used in the above embodiments has been described elsewhere herein (e.g., as described in the Culture Medium for maturing mDAPs or the fourth aspect herein), and these same descriptions are omitted herein for purpose of simplification. According to the above embodiments, the maturation method can further improve the maturity (the percentage of TH+ cells) for the mDAPs.

In certain embodiments, the culture surface is in a culture plate, a culture bottle, a culture flask, or a culture vessel. In certain embodiments, the culture plate comprises single or multilayer cell stacks, 6 wells, 12 wells, 24 wells, 48 wells, 96 wells, 384 wells, 1536 wells or more wells. In certain embodiments, the culture plate comprises flat bottom wells, or round bottom wells.

The coating matrix combination used in the fifth aspect of the present disclosure comprises a first coating matrix and a second coating matrix. This first coating matrix is not particularly limited as long as it is not laminin and can support cell adhesion for the mDAPs. This second coating matrix can improve the maturity for the mDAPs, and comprises a polylysine (PL)-based compound and/or a polyornithine (PO)-based compound.

In certain embodiments, the first coating matrix comprises, or is selected from the group consisting of: vitronectin (VTN), collagen, proteoglycan, fibronectin, entactin, elastin, a functional fragment of any of the preceeding proteins, hyaluronic acid, gelatin, and any combination thereof. In certain embodiments, the first coating matrix comprises VTN.

According to the present disclosure, a polylysine-based compound may comprise polylysine, a derivative thereof, or a salt thereof, all of which can function to improve the maturity for the mDAPs. Examples of polylysine include, without limitation, poly-L-lysine and poly-D-lysine. Examples of the derivative of polylysine include, without limitation, substituted polylysines such as for example TAMRA-PEG-Polylysine, and Polylysine-PEG-Polylysine. Examples of the salt of polylysine or a derivative thereof include, without limitation, poly-L-lysine hydrobromide, poly-L-lysine hydrochloride, and salts of substituted polylysines.

According to the present disclosure, a polyornithine-based compound, may comprise polyornithine, a derivative thereof, or a salt thereof, all of which can function to improve the maturity for the mDAPs. Examples of polyornithine include, without limitation, poly-L-ornithine and poly-D-ornithine. Examples of the derivative of polyornithine include, without limitation, substituted polyornithines such as for example DBCO-PEG-Polyornithine and Chitosan-PEG-Polyornithine, Con A-PEG-Polyornithine, alginate-PEG-Polyornithine, and Vitamin E-PEG-Polyornithine. Examples of the salt of polyornithine, or a derivative thereof include, without limitation, poly-L-ornithine hydrobromide, poly-L-ornithine hydrochloride, and salts of substituted polyornithines.

In certain embodiments, the second coating matrix comprises poly-L-lysine hydrobromide, poly-L-ornithine hydrobromide, or a mixture thereof. Representative structures of the second coating matrix that may be used in the maturation method of the present disclosure are provided below, many of which are widely commercially available from multiple sources, with indicated Cat. No. from such selected commercial sources.

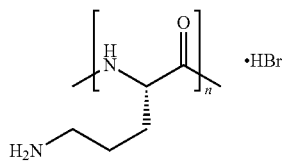

Poly-L-ornithine hydrobromide (Sigma Cat. #P3655, CAS No.: 27378-49-0).

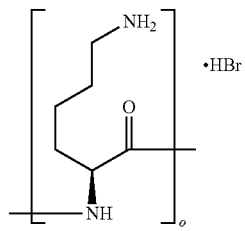

Poly-L-lysine hydrobromide (Sigma Cat. #P2636, CAS No.: 25988-63-0).

In certain embodiments, the coating matrix combination comprises VTN, and one or two of poly-L-lysine hydrobromide and poly-L-ornithine hydrobromide.

A cell culture surface may be coated with the the maturation coating matrix combination of the present disclosure by conventional technologies in the art. Generally, a cell culture surface may be firstly coated with a coating solution comprising the second coating matrix, and then with a coating solution comprising the first coating matrix. Optionally, a washing treatment (e.g., using DPBS) may be performed after the cell culture surface is coated with the second coating matrix. The coating concentrations of the first coating matrix and the second coating matrix may be easily determined by one skilled in the art. For example, the coating concentration of the first coating matrix may be each from 0.5 to 2 µg/cm², such as 1 µg/cm², and the coating concentration of the first coating matrix may be each from 1 to 2 µg/cm², such as 1 µg/cm².

In certain embodiments, the mDAPs are seeded on the culture surface at a density of about $1\times10^3$ cells/cm² to about $1\times10^6$ cells/cm² (e.g., about $5\times10^5$ cells/cm²).

In certain embodiments, the culture surface is in a culture plate, a culture bottle, a culture flask, or a culture vessel. In certain embodiments, the culture plate comprises single or multilayer cell stacks, 6 wells, 12 wells, 24 wells, 48 wells, 96 wells, 384 wells, 1536 wells or more wells. In certain embodiments, the culture plate comprises flat bottom wells, or round bottom wells.

In certain embodiments, the mDAPs are contacted with the ROCK inhibitor-containing maturation medium for a total of about 6 days.

In certain embodiments, the ROCK inhibitor-containing maturation medium does not comprise a Wnt signaling pathway inhibitor, and the method further comprises replacing the maturation medium with the same medium every several days during the maturation. In certain embodiments, the ROCK inhibitor-containing maturation medium does not comprise a Wnt signaling pathway inhibitor, and the method further comprises replacing the maturation medium with the same medium every $3^{rd}$ day during the maturation.

In certain embodiments, the ROCK inhibitor-containing maturation medium comprises the Wnt signaling pathway inhibitor, and the method further comprises replacing the maturation medium with the same medium without any Wnt signaling pathway inhibitor every several days during the maturation. In certain embodiments, the ROCK inhibitor-containing maturation medium comprises the Wnt signaling pathway inhibitor, and the method further comprises replacing the maturation medium with the same medium without any Wnt signaling pathway inhibitor every $3^{rd}$ day during the maturation.

In certain embodiments, the maturation method can improve the expression of TH. In certain embodiments, the maturation method can improve the expressions of TH and one or more selected from LMX1A, EN1, OTX2, FOX2, NURR1 and SOX6. In certain embodiments, the maturation method can improve the expressions of TH, LMX1A, EN1, OTX2, FOX2, NURR1 and SOX6.

6. Cell Populations

A substantially homogeneous population of mDAPs can be provided by using the expansion method of the present disclosure. Thus, in a sixth aspect, the present disclosure provides a substantially homogeneous population of mDAPs produced by the expansion method of the present disclosure. The expansion method of the present disclosure has been described elsewhere herein (e.g., as described in the Method for Expanding mDAPs or the third aspect herein), and these same descriptions are omitted herein for purpose of simplification. The substantially homogeneous population of mDAPs may be expanded P1, P2, P3, P4, P5 or P6 imDAPs. Expanded imDAPs at early and late passage can maintain the similar high capability to differentiate into mDA neurons.

In certain embodiments, the mDAPs in the population express FOXA2. In certain embodiments, the mDAPs in the population express FOXA2, and one or more of OTX2, SOX6, LMX1A and ENL. In certain embodiments, the mDAPs in the population express FOXA2, OTX2, SOX6, LMX1A and EN1. In certain embodiments, at least about 75%, 80%, 85%, 90%, 95% or more of mDAPs in the population express FOXA2. In certain embodiments, the substantially homogeneous population of mDAPs are P1, P2, P3, P4, P5, or P6 mDAPs.

In certain embodiments, the population of the mDAPs of the present disclosure can be cryopreserved or stored for further expansion, maturation and/or differentiation.

A substantially homogeneous population of mDA neurons (mDANs) can be provided by using the maturation method of the present disclosure from mDAPs. Thus, in a seventh aspect, the present disclosure provides a substantially homogeneous population of the mDANs produced by the maturation method of the present disclosure. The maturation method of the present disclosure has been described elsewhere herein (e.g., as described in the Method for Maturing mDAPs or the fifth aspect herein), and these same descriptions are omitted herein for purpose of simplification. mDANs may be at the early or later stage of maturation. mDANs at the early stage of maturation have the potential for terminal maturation.

In certain embodiments, the mDANs in the population express TH and FOXA2. In certain embodiments, the mDANs in the population express TH, FOXA2, and one or more of NURR1, SOX6, LMX1A and EN1. In certain embodiments, the mDANs in the population express TH, FOXA2, NURR1, SOX6, LMX1A and EN1. In certain embodiments, about 33%-55%, 33-51%, 33-42%, or 45-51% of the mDANs in the population express TH.

The population of the mDANs of the present disclosure can be cryopreserved or stored before use. The mDANs may be used for further drug research, drug screening, and clinical and therapeutic uses.

7. Kits

In an eighth aspect, the present disclosure provides a kit comprising the expansion medium of the present disclosure described herein. The expansion medium of the present disclosure has been also described elsewhere herein (e.g., as described in the Culture Medium for Expanding mDAPs or the first aspect herein), and these same descriptions are omitted herein for purpose of simplification. Optionally, the kit may further comprise the expansion coating matrix combination of the present disclosure described herein. The expansion coating matrix combination of the present disclosure has been described elsewhere herein (e.g., as described in the Coating Matrix Combination for Expanding mDAPs or the second aspect herein), and these same descriptions are omitted herein for purpose of simplification. When the kit comprises the expansion medium and the expansion coating matrix combination, they are separately packaged.

In a ninth aspect, the present disclosure provides a kit comprising the maturation medium of the present disclosure described herein. The maturation medium of the present disclosure has been described elsewhere herein (e.g., as described in the Culture Medium for maturing mDAPs or the fourth aspect herein), and these same descriptions are omitted herein for purpose of simplification. Optionally, the kit may further comprise the maturation coating matrix combination of the present disclosure described herein. The maturation coating matrix combination of the present disclosure has been described elsewhere herein (e.g., as described in the Method for Maturing mDAPs or the fifth aspect herein), and these same descriptions are omitted herein for purpose of simplification. When the kit comprises the maturation medium and the maturation coating matrix combination, they are separately packaged.

It should be understood that any aspects or embodiments of the present disclosure described herein, including those described only in the examples or claims, can be combined with any one or more other aspects and/or embodiments of the present disclosure, unless such combination is improper or expressly disclaimed.

EXAMPLES

1. Materials

All reagents and apparatuses utilized throughout the Examples of the present disclosure are commercially available. The sources of these reagents and apparatuses have been also described elsewhere herein.

2. General Test Methods (1) Flow Cytometry Analysis
1. Individualize and collect cells by either Accutase or TrypLE treatment.
2. Wash cells with 1 ml PBS and pellet cells at 250×g for 15 sec.
3. Remove supernatant, add ~200 µl of 4% PFA, mix and fix for 10 min at RT.
4. Pellet cells at 350×g for 5 min.
5. Wash cells by 1 ml of FACS buffer and pellet cells at 350×g for 5 min.
6. Remove supernatant, add 200 µl/tube of FACS buffer/ 0.1% TritonX, mix for 10 min at RT.
7. Wash cells by 1 ml of FACS buffer and pellet cells at 350×g for 5 min.
8. Remove supernatant, add 200 µl/tube of primary antibody diluted in FACS buffer, mix gently, and incubate for 30 min at RT.
9. Wash cells by 1 ml of FACS buffer and pellet cells at 350×g for 5 min.
10. Remove supernatant, and add 200 µl of secondary antibody diluted in FACS buffer, mix gently, and incubate for 30 min at RT.
11. Wash cells by 1 ml of FACS buffer and pellet cells at 300×g for 5 min.
12. Remove supernatant, add 200 µl of FACS buffer, and run samples on the flow cytometry.

(2) qRT-PCR
1. For qRT-PCR analysis of mRNA gene expression, RNA should be harvested from at least $2 \times 10^6$ cells.
2. Harvest cells, add 350 µl of buffer RLT+1% (vol/vol) β-mercaptoethanol to the well, transfer the lysate to a 1.5 ml tube, and put it immediately on ice.
3. Perform RNA extraction using the Tiangen Kit (DP430), and follow the manufacturer's protocol 'Purification of total RNA from animal and human cells'.
4. When the RNA extraction was completed, determine the RNA concentration using a Nanodrop instrument.
5. Perform the first-strand cDNA synthesis reaction with 1 µg of RNA using the HiScript™ II Q RT SuperMIX for qPCR(+gDNA wiper) Kit (Vazyme, #R223-01) for RT-qPCR. Follow the manufacturer's 'First-Strand cDNA Synthesis' protocol. This reaction would yield a 20 µl product.
6. Dilute the 10l cDNA product in 80 µl of nuclease-free water.
7. Pipette the diluted cDNA product (1 µl), Sybr green master mix (5 µl, Transgen, #AQ131) and 0.95 µM reverse/forward primer mix (4 µl) into a 384-well PCR plate in triplicate, either manually or using an automated pipetting robot. The complete primer panel included the target genes and the housekeeping gene (RPL13A). In the analysis, also included a sample of undifferentiated hPSCs to determine the gene expression levels relative to the expression in hPSCs.
8. Analyze the samples by running a quantitative PCR on the LightCycler 480 instrument using a 40× cycle two-step protocol with a 60° C., 60 sec annealing/ elongation step and a 95° C., 30 sec denaturation step. The average CT values from the three technical replicates were used for calculations of relative gene expression using the ΔΔCT method. For each gene, calculate the FC of the differentiated samples relative to the undifferentiated control sample using the housekeeping gene for normalization. Next, calculate the average of the FC values on the basis of the housekeeping gene.

(3) Immunocytochemical Analysis

1. Cell fixation: Remove the medium from the cells and wash with PBS. Add 4% (wt/vol) PFA (e.g., 200 μl to a well in a 48-well plate) and incubate at room temperature (RT) for 15 min. after incubation, wash the cells three times in PBS.
2. Blocking: Remove PBS from the wells and add blocking solution to the cells, add enough volume to cover the cells. Leave the cells in blocking solution for 1 h at RT.
3. Primary antibodies incubation: Remove the blocking solution from the cells and add the primary antibody solutions (~100 μl/cm$^2$). Incubate for 1 h at RT on a shaker.
4. Secondary antibodies incubation: Remove the primary antibody solutions and wash the cells three times in PBS. Add the secondary antibody solution to the cells (~100 μl/cm$^2$), wrap the plate in aluminum foil to avoid bleaching of the fluorophores and incubate for 1 h at RT on a shaker.
5. DAPI incubation: Remove the secondary antibody solution and wash the cells twice in PBS. Add the DAPI solution (1:1000) to the cells (~100 μl/cm$^2$), wrap the plate in aluminum foil to avoid bleaching of the fluorophores and incubate for 10 min at RT on a shaker.
6. Wash the cells three times in PBS and leave the plate wrapped in aluminum foil at 4° C. until analysis.
7. Analyze the immunocytochemically stained cells using a fluorescence microscope and estimate the number of positive cells.

Examples 1-5: Development and Verification of imDAP Expansion Medium Based on the Combination of LDN193189/CHIR99021/FGF8b/Blebbistatin It has been previously shown that LDN193189, CHIR99021, Blebbistatin and FGF8b are necessary to expand mDAPs as a homogeneous population. However, it was unclear whether the expanded imDAPs retained their characteristics in the expansion medium supplemented with Blebbistatin, LDN193189, CHIR99021 and FGF8b. The present examples demonstrated that the expansion medium based on this combination can only expand imDAPs at a limited expansion efficiency, in particular, cannot support the long-term expansion of imDAPs while maintaining imDAP-specific phenotypes.

Example 1 imDAPs were produced according to the method described in CN201910169525.0. The imDAPs (PO) were seeded on VTN-coated plates (1 μg/cm$^2$) at a density of 1×10$^5$ cells/cm$^2$ in the expansion medium (50% DMEM/F12, 50% Neurobasal™ medium, 1% (v/v) Glutamax, 2% (v/v) B27 (50×), 0.2 μM LDN193189, 3 μM CHIR99021, 100 ng/mL FGF8b) in the absence or presence of 5 μM Blebbistatin. In case where Blebbistatin is present, Blebbistatin was either removed 24 hrs after plating or present throughout the culture period. The medium was changed every day for 5 days.

The results were shown in FIG. 1A. FIG. 1A (left image) showed the morphology of cells expanded in the absence of Blebbistatin. FIG. 1A (middle image) showed the morphology of cells expanded in case where Blebbistatin was removed 24 hrs after plating, and FIG. 1A (right image) showed the morphology of cells expanded in case where Blebbistatin was present throughout the culture period. Apparently, adding Blebbistatin throughout culture supported better imDAP expansion compared to medium without Blebbistatin, or adding Blebbistatin at plating day only.

Example 2 imDAPs were produced according to the method described in CN201910169525.0. The imDAPs (PO) were seeded on VTN-coated plates (1 μg/cm$^2$) at a density of 1×10$^5$ cells/cm$^2$ in the expansion medium (50% DMEM/F12, 50% Neurobasal™ medium, 1% (v/v) Glutamax, 2% (v/v) B27 (50×), 3 μM CHIR99021, 100 ng/mL FGF8b, 5 μM Blebbistatin) in the absence or presence of 0.2 μM LDN193189. The medium was changed every day for 5 days.

The results were shown in FIG. 1B. It was apparent that imDAPs cultured without LDN193189 showed more flattened morphology as compared with those cultured with LDN193189.

Example 3 imDAPs were produced according to the method described in CN201910169525.0. The imDAPs (PO) were seeded on VTN-coated plates (1 μg/cm$^2$) at a density of 1×10$^5$ cells/cm$^2$ in the expansion medium (50% DMEM/F12, 50% Neurobasal™ medium, 1% (v/v) Glutamax, 2% (v/v) B27, 0.2 μM LDN193189, 100 ng/mL FGF8b, 5 μM Blebbistatin) with different concentration of CHIR99021 (0, 1.25, 3 μM). The medium was changed every day for 5 days. Cells were collected for RT-qPCR assay.

The results were shown in FIG. 1C. qRT-PCR analysis of expanded imDAPs showed that treatment with 3 μM of CHIR99021 during expansion allowed better maintenance of mDAP marker expression (EN1, LMX1A, FOXA2).

Example 4 imDAPs were produced according to the method described in CN201910169525.0. The imDAPs (PO) were seeded on VTN-coated plates (1 μg/cm$^2$) at a density of 1×10$^5$ cells/cm$^2$ in the expansion medium (50% DMEM/F12, 50% Neurobasal™ medium, 1% (v/v) Glutamax, 2% (v/v) B27 (50×), 0.2 μM LDN193189, 3 μM CHIR99021, 5 μM Blebbistatin) in the absence or presence of 100 ng/mL FGF8b. The medium was changed every day for 5 days. Cells were collected for RT-qPCR assay.

The results were shown in FIG. 1D. qRT-PCR analysis of expanded imDAPs showed that treatment with FGF8b during expansion allowed improvement of mDAP marker expression (EN1, and LMX1A) as compared with treatment without FGF8b, but the improvement of FOXA2 expression was not observed.

Example 5 imDAPs were produced according to the method described in CN201910169525.0. The imDAPs (PO) were seeded on VTN-coated plates (1 μg/cm$^2$) at a density of 1×10$^5$ cells/cm$^2$ in the expansion medium (50% DMEM/

F12, 50% Neurobasal™ medium, 1% (v/v) Glutamax, 2% (v/v) B27 (50×), 0.2 µM LDN193189, 3 µM CHIR99021, 100 ng/mL FGF8b, 5 µM Blebbistatin). The medium was changed every day. When imDAPs reach 100% confluence (4-5 days), cells were passaged enzymatically with 1× TrypLE, centrifuged at 250 g for 5 minutes, counted and replaced on new VTN-coated plates (1 µg/cm$^2$) at a density of $1\times10^5$ cells/cm$^2$ in the expansion medium. imDAPs were continuously expanded for 6 passages. At each passage, imDAPs were harvested at an expansion fold 5-10 (over the initial number of imDAPs plated).

Figure 1F:
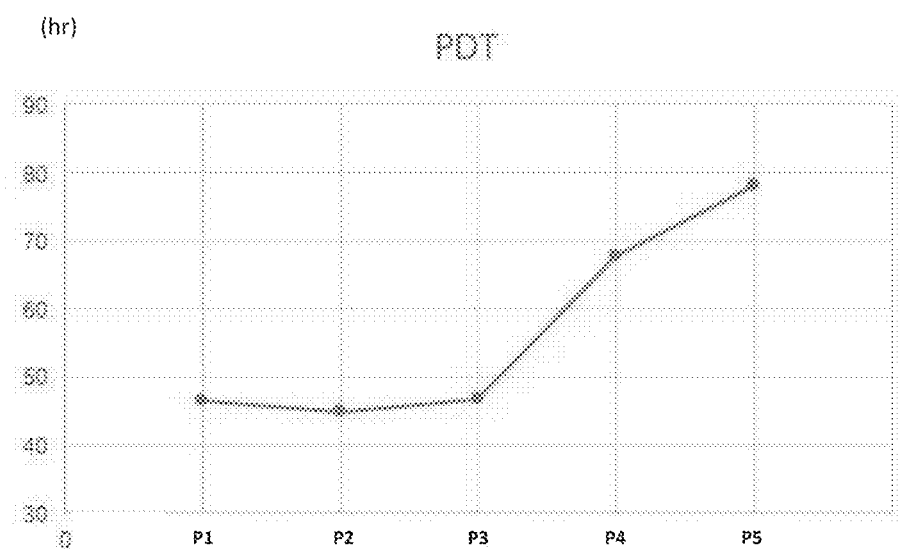
FIG. 1F shows representative Population Doubling Time (PDT) of imDAPs during passaging (P1-P5)
Figure 1G:
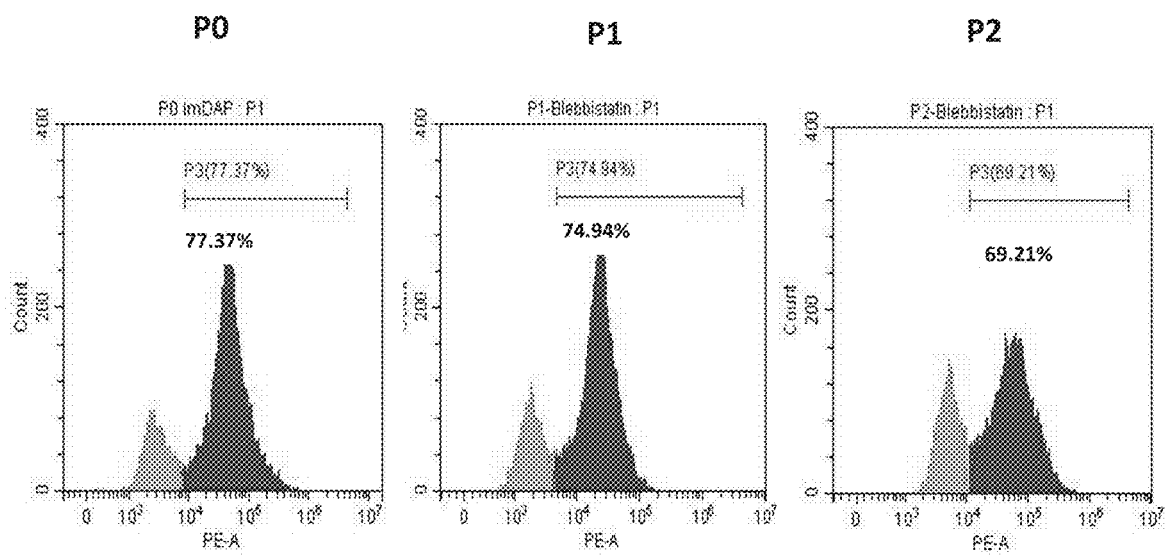
FIG. 1G shows the results of flow cytometry analysis of FOXA2 expression in imDAPs at P0, P1 and P2 (P represents Passage)
Figure 1H:
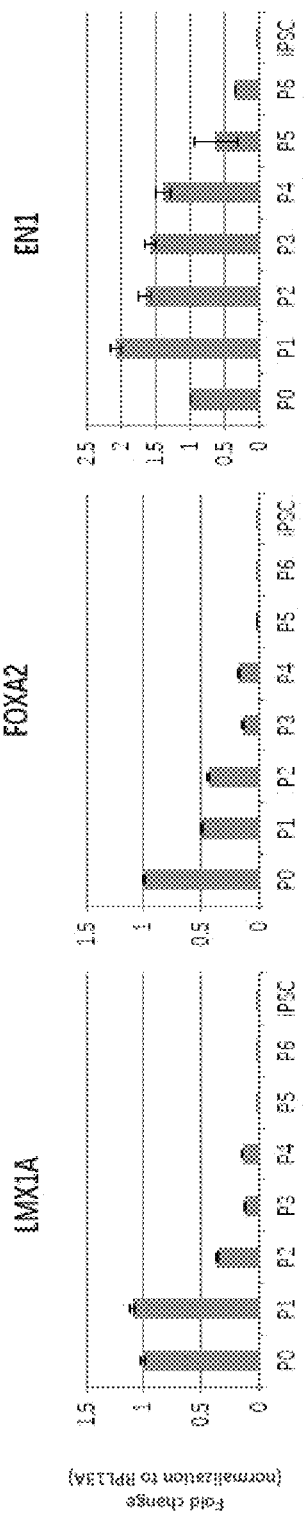
FIG. 1H shows the results of qRT-PCR analysis of the expression of imDAP-specific markers, LMX1A, FOXA2 and EN1 in imDAPs at each passage (P0~P6).

Typical cell morphology of each passage (P1-P6) was shown in FIG. 1E. Population Doubling Time (PDT) of each passage (P1-P5) was shown in FIG. 1F. It was apparent that, from P1 to P3, PDT maintained at a high value of about 48 hrs, which meant a limited expansion efficiency, and from P3 onwards, the proliferation of imDAPs started to slow down significantly. The percentages of Foxa2-expressing cells at P0, P1 and P2 were shown in FIG. 1G. The results showed that the percentage of Foxa2-expressing cells decreased over passaging, in particular, decreased significantly after 2 passages using imDAP expansion medium based on the combination of LDN193189/CHIR99021/FGF8b/Blebbistatin. FIG. 1H showed the RT-qPCR results of mDAP specific markers (EN1, LMX1A and FOXA2) at each passage. The expression of LMXIA/FOXA2/EN1, in particular FOXA, decreased significantly over passages.

Example 6 Y27632 Promoted imDAP Expansion

This example demonstrated that the expansion medium supplemented with Y27632 was capable of improving the expression of Foxa2 for imDAP cells than the expansion medium supplemented with Blebbistatin.

imDAPs were produced according to the method described in CN201910169525.0. The imDAPs (P0) were seeded on VTN-coated plates (1 µg/cm$^2$) at a low density of $1\times10^4$ cells/cm$^2$, and cultured in the expansion medium (50% DMEM/F12, 50% Neurobasal™ medium, 1% (v/v) Glutamax, 2% (v/v) B27 (50×), 0.2 µM LDN193189, 3 µM CHIR99021, 100 ng/mL FGF8b) with either 5 µM Blebbistatin or 10 µM Y27632. Medium was replaced every 3$^{rd}$ day. At Day 6, cells were collected for FACS analysis.

Figure 2:
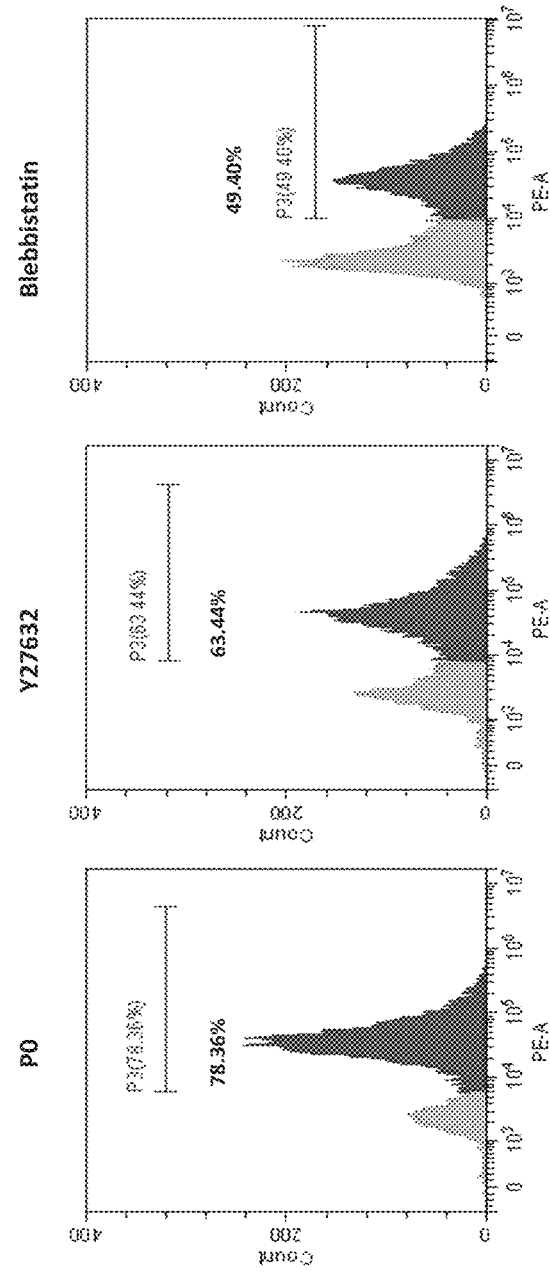
FIG. 2 shows the comparison of the effects of Y27632 and Blebbistatin on the expression of imDAP-specific marker FOXA2 according to the Example 6 of the present disclosure.

The results were shown in FIG. 2. The data clearly showed that the expansion medium supplemented with Y27632 was capable of improving the percentage of Foxa2-expressing cells than Blebbistatin. On the other hand, however, even though Y27632 could improve Foxa2 expression compared to Blebbistatin, the percentage of Foxa2-expressing cells still decreased during passages.

Example 7 NOTCH2/TGFβ2 Enriched in imDAPs

The example demonstrated that NOTCH2/TGF02 were enriched in imDAPs. Manipulations of these signaling pathways may allow efficient imDAP expansion while maintain mDAP phenotypes.

Single cells were encapsulated in droplets using 10×Genomics Technology and processed according to the following procedures. Briefly, every cell and every transcript were uniquely barcoded using a unique molecular identifier (UMI). Libraries were generated and sequenced from the cDNA and the 10× barcodes were used to associate individual reads back to the individual partitions. Then, the cDNAs were collected together, amplified and sequenced according to the standard procedure of Illumina-ready sequencing libraries.

Figure 3A:
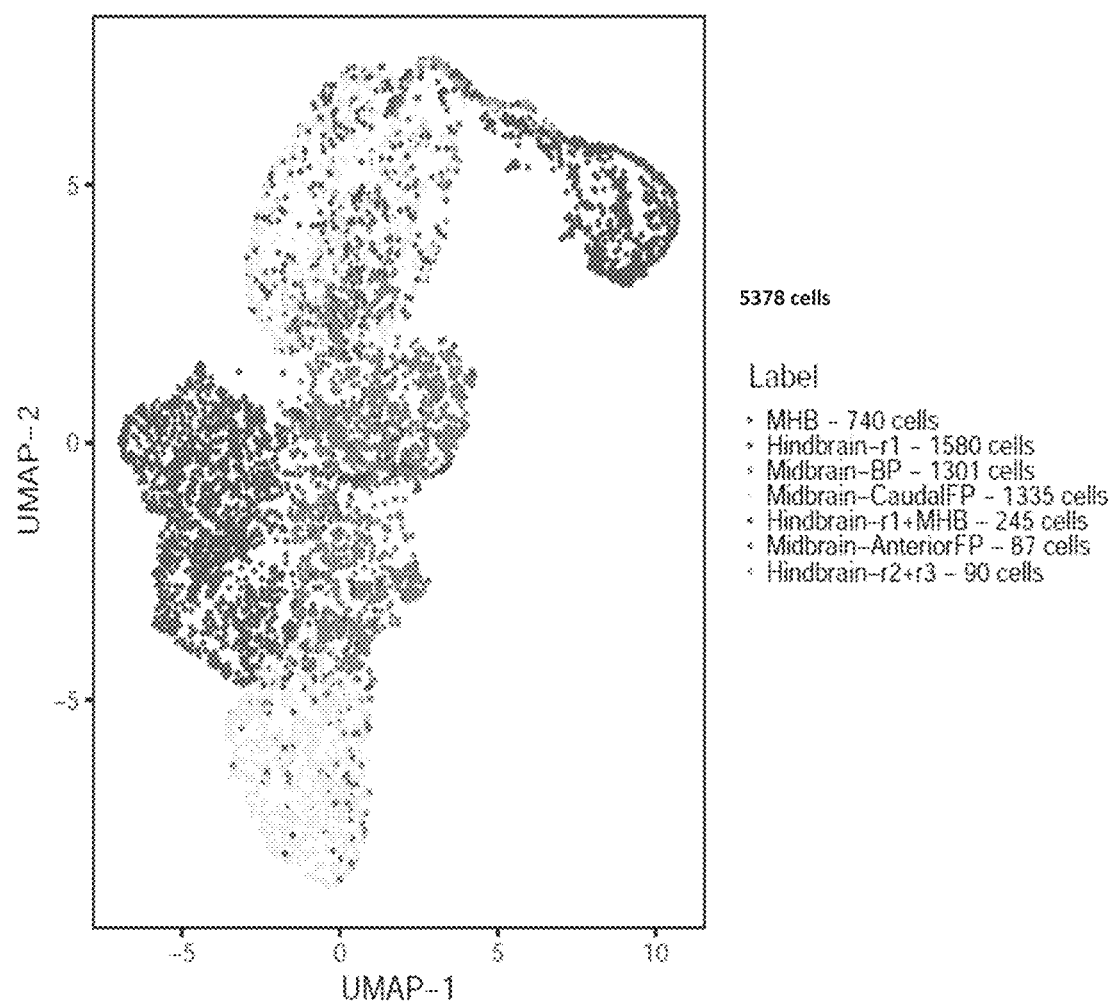
FIG. 3A is a visualization of clustering results of imDAP single cell RNA sequencing data using UMAP.
Figure 3B:
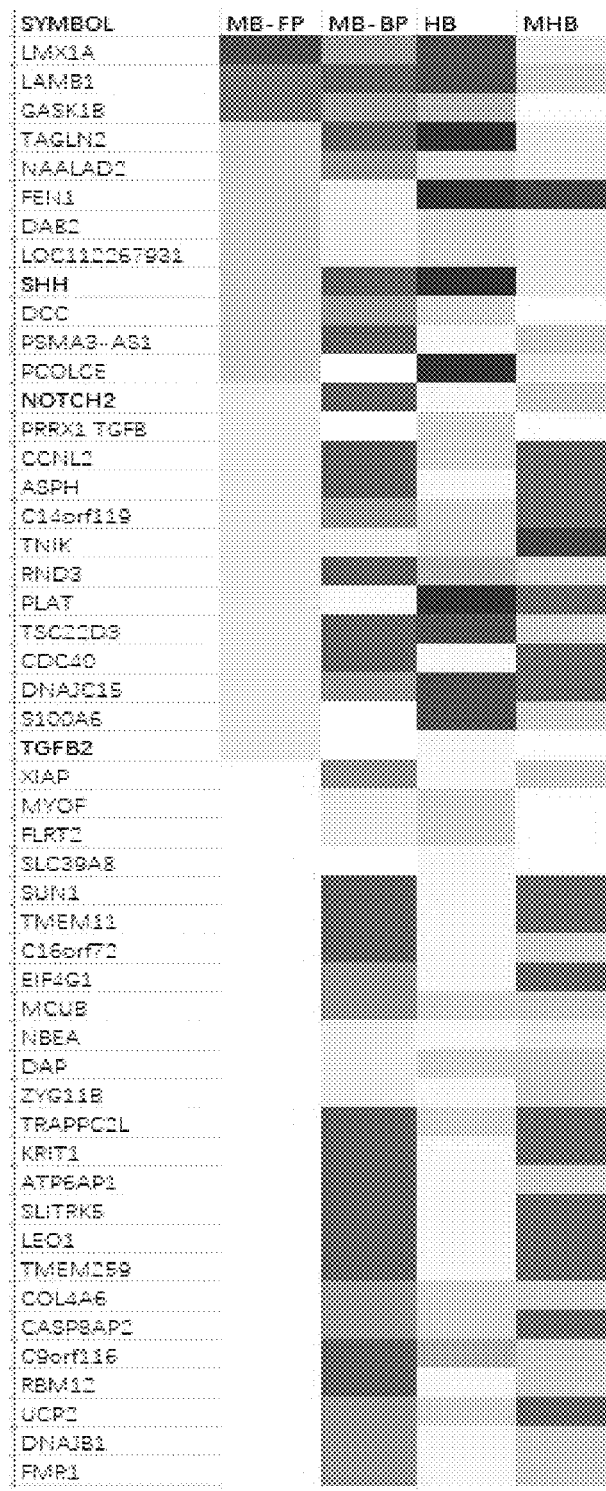
FIG. 3B is a heatmap of subsets of genes that are enriched in imDAPs, wherein MB-FP: midbrain floor plate; MB-BP: midbrain basal plate; HB: hindbrain; MHB: midbrain-hindbrain boundary.

For downstream analyses after initial Cell Ranger metric assessment, cells with low-quality sequencing data were removed. Genes with reads either greater than or equal to 3 in all cells were considered to be ubiquitously expressed in all cell types in the sample, thus removed prior to further analysis. The cells in the following brain regions appeared to be absent in the sample: Forebrain, Diencephalon, Dorsal midbrain, Lateral midbrain, Hindbrain r2,3. Cells clustering were done in the following order: (1) Midbrain-hindbrain boundary (MHB, FGF8+), (2) Hindbrain r1 (HB r1, GBX2+), (3) Midbrain basal plate (MBP, OTX2+/NKX6.1+, OTX2+/NKX2.2+, OTX2+/PITX2+), (4) Midbrain caudal floor plate (MFP, EN1+/LMX1A+/FOXA2+/OTX2+), (5) Leftover cells. The leftover cells were then grouped into one of the first 4 clusters with closest overall gene expression pattern. For visualization and clustering, manifolds were calculated using UMAP methods (FIG. 3A). Using the differentially expressed gene signatures, it was found that NOTCH2/TGFβ2 were enriched in MFP cells (FIG. 3B). Manipulations of these signaling pathways might allow efficient imDAP expansion while maintaining mDAP phenotypes.

Figure 4A:
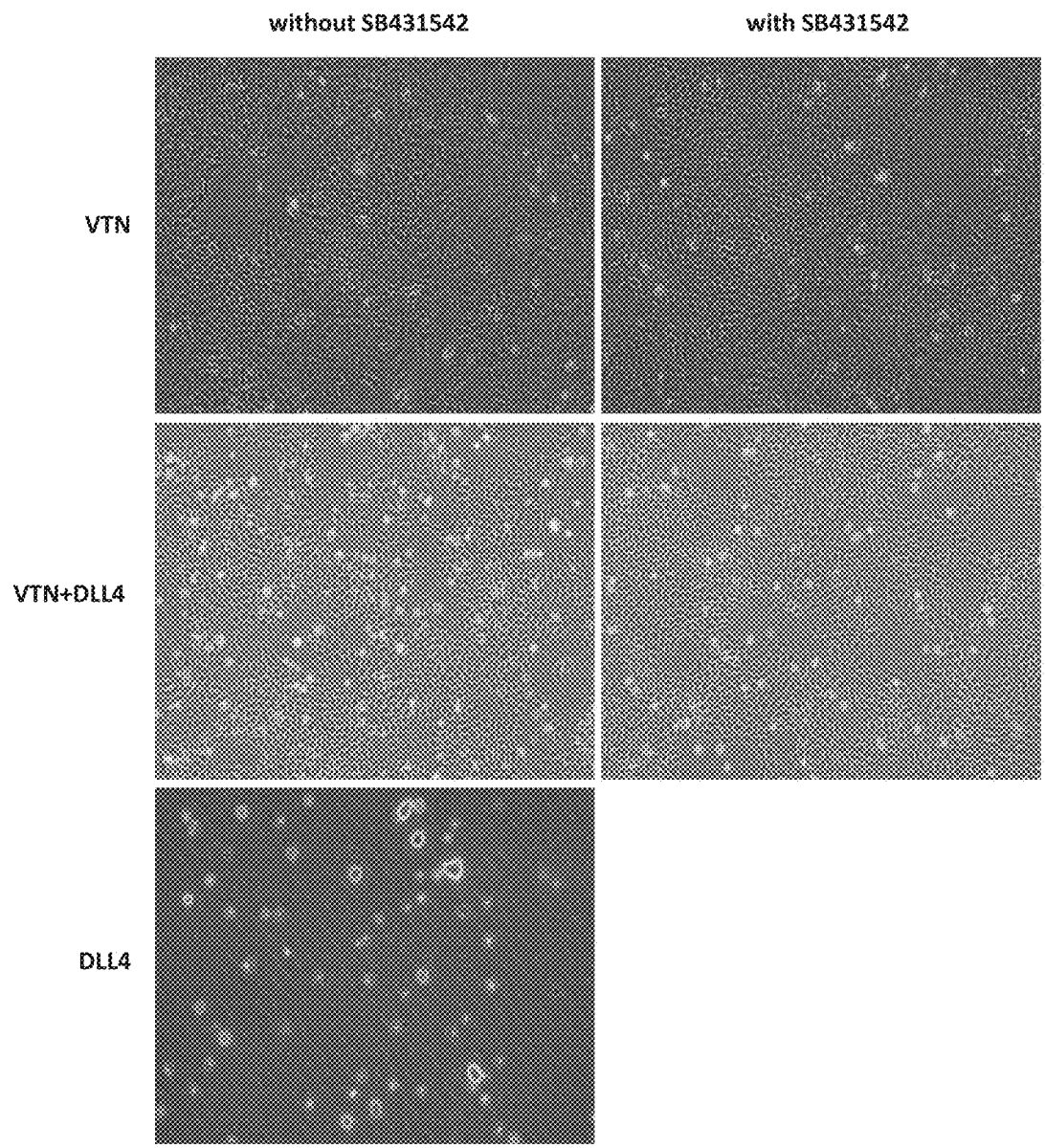
FIG. 4A shows the morphologies of imDAPs expanded with SB431542 and without SB431542 on a culture surface coated with VTN, VTN+DLL4, or DLL4.
Figure 4B:
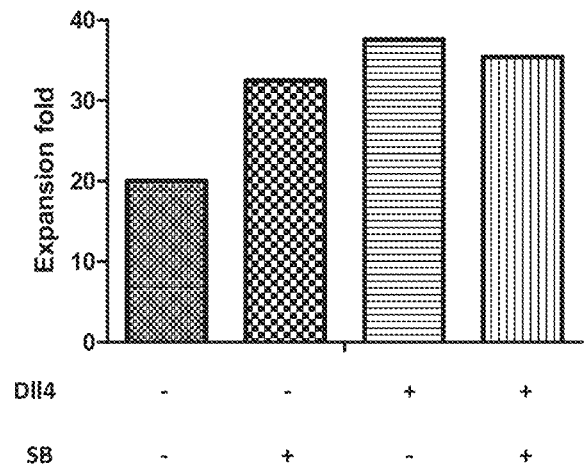
FIG. 4B shows the effects of DLL4 and SB431542 on imDAP expansion efficiency.
Figure 4C:
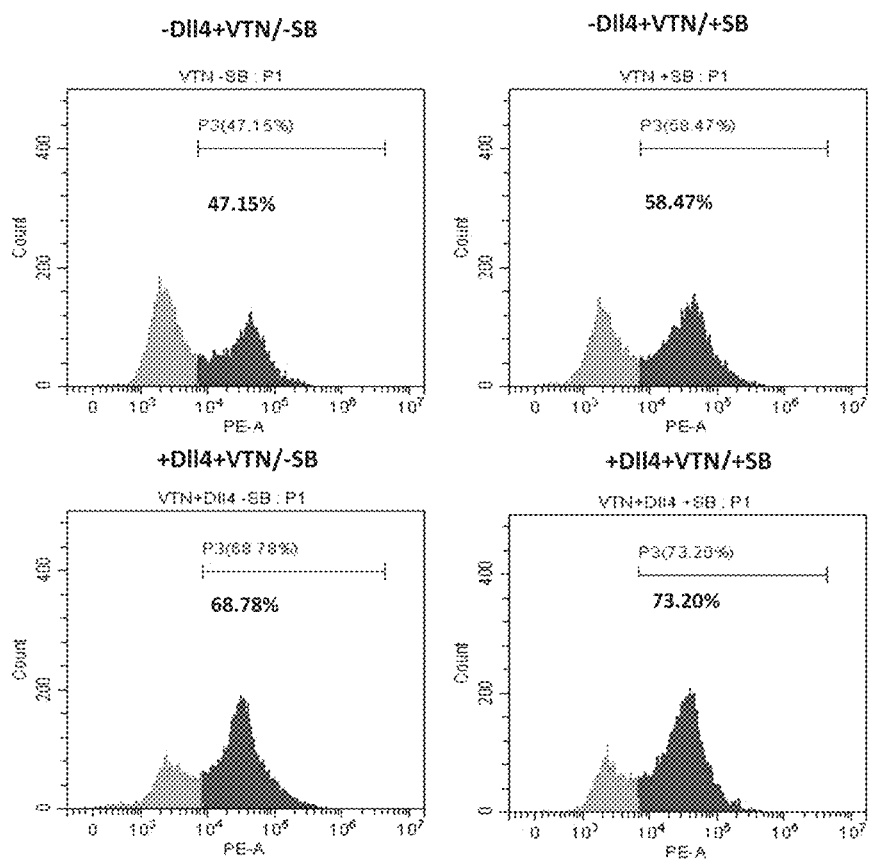
FIG. 4C shows the results of FACS analysis of FOXA2 expression in imDAPs expanded with SB431542 and without SB431542 on a culture surface coated with VTN or VTN+DLL4.

Example 8 NOTCH Activation and/or TGF-β Inhibition Supported Better imDAP Expansion The example showed that NOTCH activation (e.g., using DLL4) and TGF-β inhibition (e.g., using SB431542) supported better expansion of imDAPs.

imDAPs were produced according to the method described in CN201910169525.0. The imDAPs (PO) were seeded on DLL4-coated (1 µg/cm$^2$), VTN-coated (1 µg/cm$^2$) and DLL4/VTN-coated (1 µg/cm$^2$ for each) plates at a low density of $1\times10^4$ cells/cm$^2$ respectively, and cultured in the expansion medium in the absence or presence of 5 µM SB431542. Medium was replaced every 3$^{rd}$ day until reaching 100% confluence (6 days) for cell collection. The typical cell morphology on day 4 was recorded (FIG. 4A). The cell number of each group was counted by Vi-cell cytometer (FIG. 4B). The cells of each group were stained with Foxa2-PE antibody (BD, #561589), the percentage of Foxa2+ imDAPs were analyzed by flow cytometry (FIG. 4C). The expansion medium used in this example contained the following components: 50% DMEM/F12, 50% Neurobasal™ medium, 1% (v/v) Glutamax, 1% (v/v) B27, 50 µg/ml ascorbic acid, 0.2 µM LDN193189, 100 ng/ml FGF8b, 3 µM CHIR99021 and 10 µM Y27632.

Here, the effect of DLL4 and SB431542 on supporting imDAPs expansion as a homogeneous population was examined. The results were shown in FIG. 4. Specifically, FIG. 4A showed that DLL4 alone could not support the attachment of imDAPs. The imDAPs on VTN showed flattened morphology. The imDAPs cultured on the surface coated with both VTN and DLL4 were more homogeneous during expansion. FIG. 4B showed that DLL4 alone, SB431542 alone or their combination could greatly improve the imDAP expansion efficiency (about 32 fold or more) as compared with the expansion without both DLL4 and SB431542 (about 20 fold or more). In FIG. 4C, by comparing the result of -DLL4+VTN/-SB with the result of -DLL4+VTN/+SB and by comparing the result of +DLL4+VTN/-SB with the result of +DLL4+VTN/+SB, it was shown that SB431542 alone could improve FOXA2 expression, and by comparing the result of -DLL4+VTN/-SB with the result of +DLL4+VTN/-SB and by comparing the result of -DLL4+VTN/+SB with the result of +DLL4+VTN/+SB, it was shown that DLL4 alone could improve FOXA2 expression. In particular, the combination of DLL4/VTN with SB431542 maintained best FOXA2 expression during expansion.

Example 9 LDN193189, FGF8b and/or FGF2 Had No Additional Effects on imDAP Expansion In order to further demonstrate whether LDN193189, FGF8b and FGF2 are essential for imDAP expansion, the present example examined the effects of LDN193189, FGF8b and FGF2 on imDAP expansion.

imDAPs were produced according to the method described in CN201910169525.0. The imDAPs (P0) were seeded on DLL4/VTN-coated (1 µg/cm$^2$ for each) plates at a low density of 1×10$^4$ cells/cm$^2$, and cultured in the expansion medium (EM1, EM2, EM3, EM4). Medium was replaced every 3$^{rd}$ day until reaching 100% confluence (6 days) for cell collection. EM1 used in Example 9 contained the following components: 50% DMEM/F12, 50% Neurobasal™ medium, 1% (v/v) Glutamax, 1% (v/v) B27 (50×), 50 µg/ml ascorbic acid, 3 µM CHIR99021, 5 µM SB431542 and 10 µM Y27632. EM2 used in Example 9 contained the following components: 50% DMEM/F12, 50% Neurobasal™ medium, 1% (v/v) Glutamax, 1% (v/v) B27 (50×), 50 µg/ml ascorbic acid, 0.2 µM LDN193189, 3 µM CHIR99021, 5 µM SB431542 and 10 µM Y27632. EM3 used in Example 9 contained the following components: 50% DMEM/F12, 50% Neurobasal™ medium, 1% (v/v) Glutamax, 1% (v/v) B27 (50×), 50 µg/mL ascorbic acid, 0.2 µM LDN193189, 100 ng/ml FGF8b, 3 µM CHIR99021, 5 µM SB431542 and 10 µM Y27632. EM4 used in Example 9 contained the following components: 50% DMEM/F12, 50% Neurobasal™ medium, 1% (v/v) Glutamax, 1% (v/v) B27 (50×), 50 µg/ml ascorbic acid, 0.2 µM LDN193189, 10 ng/ml FGF2, 3 µM CHIR99021, 5 µM SB431542 and 10 µM Y27632.

Figure 5A:
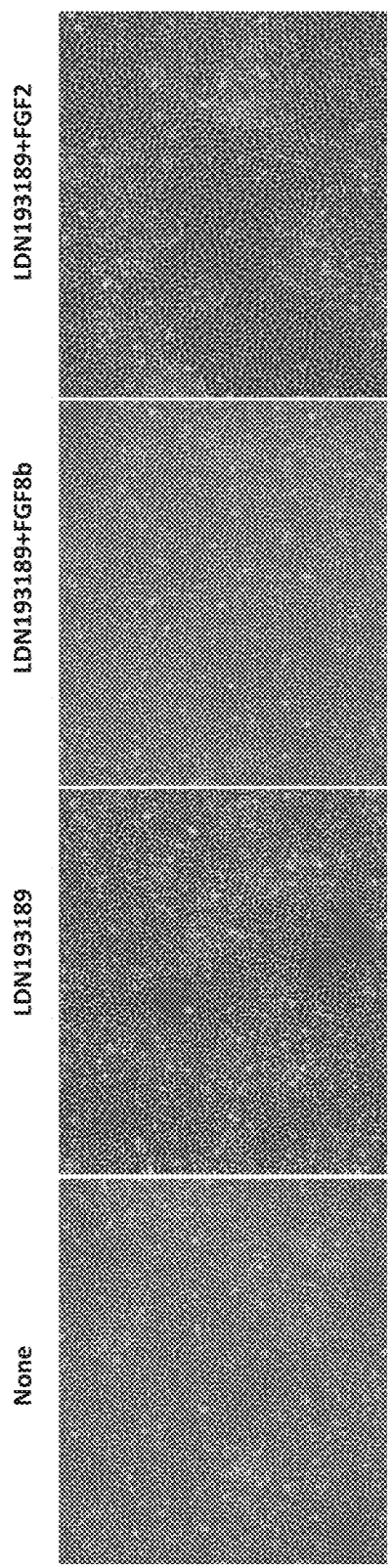
FIG. 5A shows the morphologies of imDAPs expanded with LDN193189, LDN193189+FGF8b, LDN193189+FGF2 and without any of them (Scale bar: 50 μm)
Figure 5B:
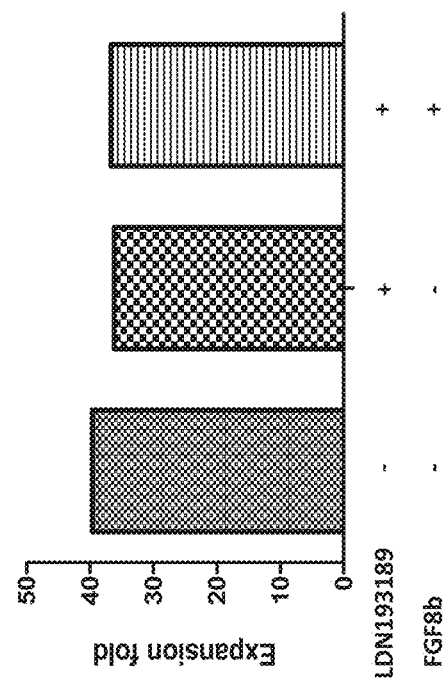
FIG. 5B shows the effects of LDN193189 and/or FGF8b on imDAP expansion efficiency.
Figure 5C:
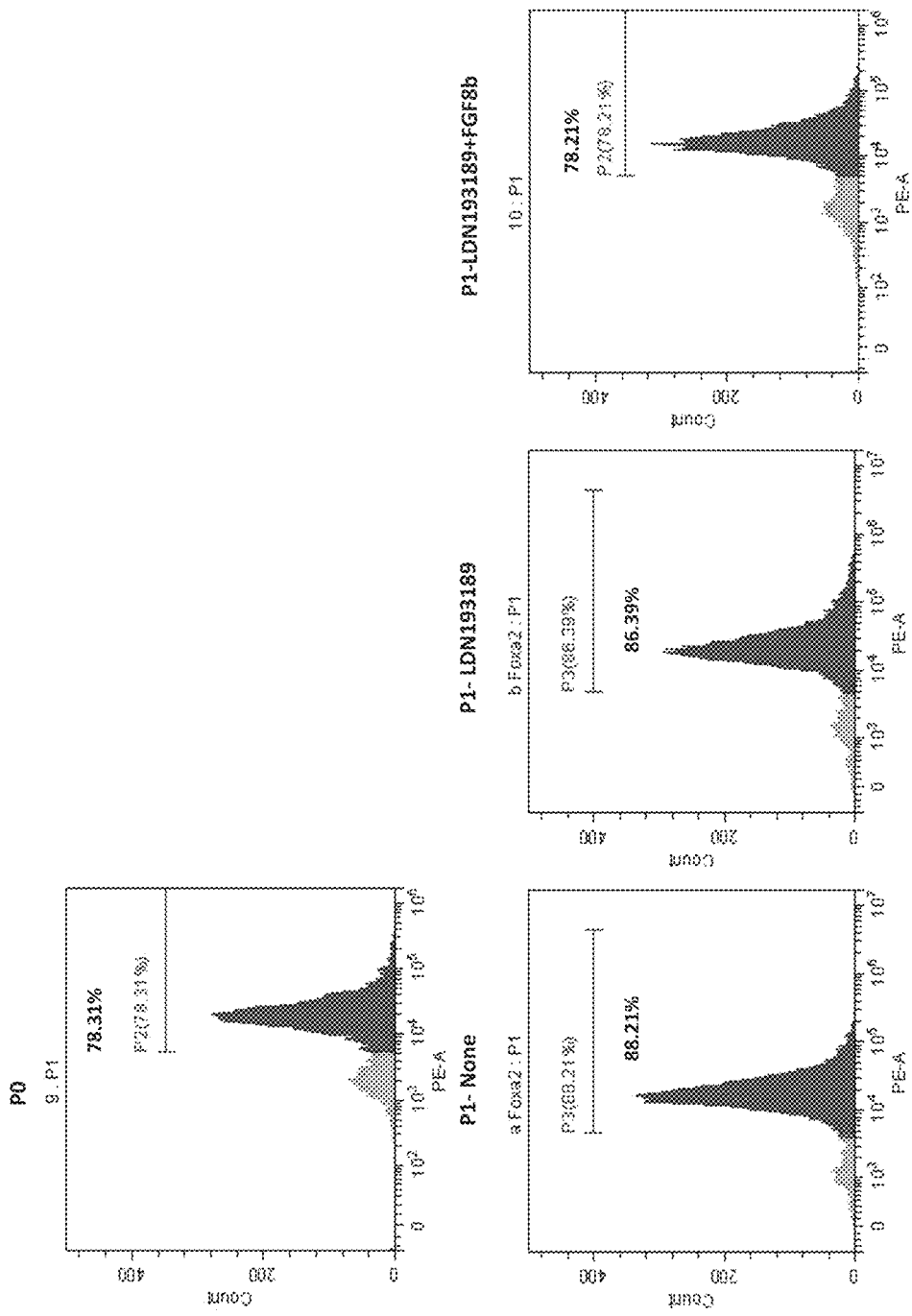
FIG. 5C shows the results of FACS analysis of FOXA2 expression in imDAPs expanded with LDN193189 or LDN193189+FGF8b and without any of them.

FIG. 5A showed the typical cell morphology on day 5. As shown in FIG. 5A, some obvious heterogeneous cells were observed when cells were cultured with FGF2. The cell number of each group was counted by Vi-cell cytometer (FIG. 5B). As shown in FIG. 5B, adding LDN193189 and/or FGF8b had no additional effect on increasing the cell number during expansion. The cells of each group were stained with Foxa2-PE antibody (BD, #561589), the percentage of Foxa2+ imDAPs were analyzed by flow cytometry (FIG. 5C). As shown in FIG. 5C, as compared with P0 cells, the expansion medium without LDN193189 and FGF8b could maintain or even improve the expression of Foxa2 for P1 cells, and although the expansion medium with LDN193189 and/or FGF8b could still maintain or even improve the expression of Foxa2 for P1 cells, addition of FGF8b and/or LDN193189 slightly decreased the expression of FOXA2 for imDAPs. The results demonstrated that LDN193189, FGF8b and/or FGF2 had no additional effects on imDAP expansion, and were not essential for imDAP expansion.

Example 10 NOTCH Activation in Combination with TGF-β Inhibition Supported imDAP Long-Term Expansion This example showed that the novel combination of CHIR99021, SB431542 and Y27632 supported imDAP long-term expansion on VTN/DLL4-coated surface.

imDAPs were produced according to the method described in CN201910169525.0. The imDAPs (P0) were seeded on DLL4/VTN-coated (1 µg/cm$^2$ for each) plates at a low density of 1×10$^4$ cells/cm$^2$ in the expansion medium. Medium was replaced every 3$^{rd}$ day until reaching 100% confluence (6 days) for cell passaging. imDAPs were passaged enzymatically with 1× TrypLE, centrifuged at 250 g for 5 minutes, counted and plated on new DLL4/VTN-coated plates at a density of 1×10$^4$ cells/cm$^2$ in the expansion medium. imDAPs were expanded and maintained in the expansion medium for 6 passages. The expansion medium used in Example 10 contained the following components: 50% DMEM/F12, 50% Neurobasal™ medium, 1% (v/v) Glutamax, 1% (v/v) B27 (5×), 50 µg/mL ascorbic acid, 3 µM CHIR99021, 5 µM SB431542 and 10 µM Y27632.

Figure 6A:
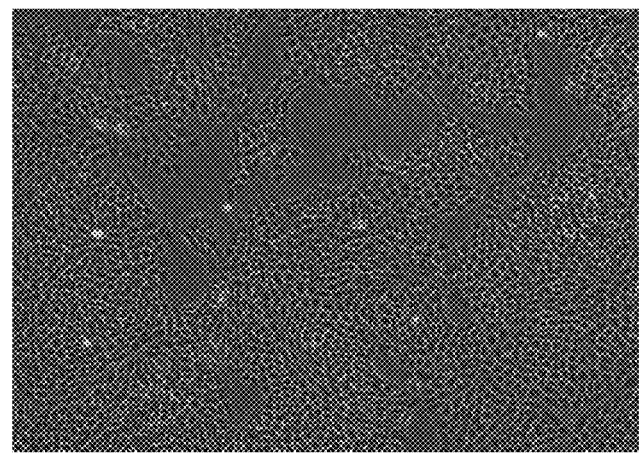
FIG. 6A shows the typical morphology of P3 imDAPs on day 5 (Scale bar: 50 μm)
Figure 6B:
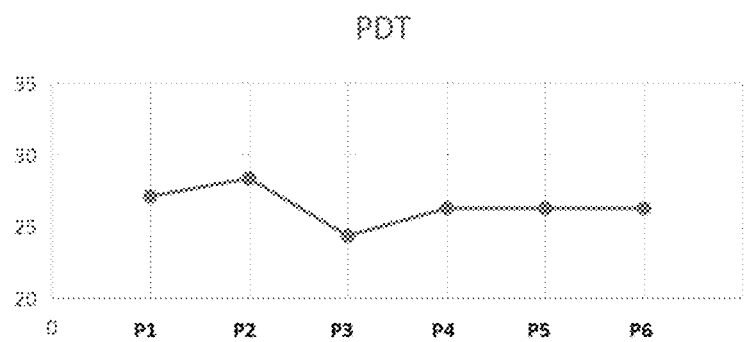
FIG. 6B shows representative PDT of imDAPs at each passage (P1~P6) during long-tem expansion.

FIG. 6A showed the typical cell morphology of P3 on day 5. Cells at each passage were collected on day 6. The cell number was counted by Vi-cell cytometer, and FIG. 6B showed the imDAP PDT at each passage (P1-P6). As shown in FIG. 6B, the expanded imDAPs maintained similar PDT at a significantly lower value of about 25-28 hrs from P1 to P6 as compared with FIG. 1F. The shorter PDT at each passage meant a higher expansion efficiency at each passage, and similar PDT at each passage meant that the expansion capability of cells at each passage could be better maintained. FIG. 6C showed the percentage of FOXA2+ cells at P0, P1, P2, P3, P4 and P5. As shown in FIG. 6C, the expansion medium with the combination of CHIR99021, SB431542 and Y27632 could maintain or even improve FOXA2 expression during long-term expansion on VTN/DLL4-coated surface. FIG. 6D showed the gene expression analysis for key mDAP markers (P0~P6). As shown in FIG. 6D, the expressions of LMX1A, FOXA2, EN1, OTX2 and SOX6 were substantially maintained during long-term expansion. The data showed that the expansion medium with the above combination could support imDAP long-term expansion on VTN/DLL4-coated surface. It not only significantly improved the expansion efficiency (its expansion fold for each passage was 8 times as high as that of the expansion medium in Example 5) and substantially maintained the improved expansion efficiency at same or similar level during cell expansion and passaging, but also maintained or improved the expression of imDAP-specific markers (e.g., Foxa2) or cell purity (e.g., FOXA2+ cells) during cell expansion and passaging.

Example 11 Development of the imDAP Maturation Medium

B27 is commonly used as a medium supplement for neuron maturation in the literature. This example showed that, when B27 was replaced with hPLT or HhPLT, the maturation with hPLT or HhPLT gave rise to higher proportion of TH+ neurons in comparison to the maturation with B27.

imDAPs were produced according to the method described in CN201910169525.0, and expanded as described in Example 10. The expanded imDAPs were seeded on VTN-coated (1 µg/cm$^2$) plates at a density of 5×10$^5$ cells/cm$^2$ (Day 0), and cultured in the maturation medium (MM-P, MM-H, MM-B) supplemented with 1 µM IWR1. MM-P used in Example 11 contained the following components: Neurobasal™ medium, 1% (v/v) Glutamax, 0.5 mM Db-cAMP sodium salt, 200 µM ascorbic acid, 20 ng/ml BDNF, 20 ng/ml GDNF, 1 ng/ml TGF-β 3, 10 µM DAPT, hPLT (0.5%, 1%, 2%). MM-H used in Example 11 contained the following components: Neurobasal™ medium, 1% (v/v) Glutamax, 0.5 mM Db-cAMP sodium salt, 200 µM ascorbic acid, 20 ng/ml BDNF, 20 ng/ml GDNF, 1 ng/ml TGF-β 3, 10 µM DAPT, HhPLT (0.5%, 1%, 2%). MM-B used in Example 11 contained the following components: Neurobasal, 1% (v/v) Glutamax, 0.5 mM Db-cAMP sodium salt, 200 μM ascorbic acid, 20 ng/ml BDNF, 20 ng/ml GDNF, 1 ng/ml TGF-β 3, 10 μM DAPT, 2% (v/v) B27 (50×) (as control). The above HhPLT was produced from hPLT as follows. The hPLT was centrifuged at 3000 g for 30 min at 4° C. to obtain the supernatant, which was heated to 56° C. for 30 min. The suspension was finally cooled down to 4° C. at least 5 min, and spun at 3000 g for 30 min at 4° C. to obtain the HhPLT supernatant. Aliquots were prepared and stored at −80° C. until use. The above Medium was changed every $3^{rd}$ day. On day 7, the imDAPs at early maturation stage were dissociated enzymatically with 1× TrypLE, centrifuged at 250 g for 5 minutes.

Figure 7C:
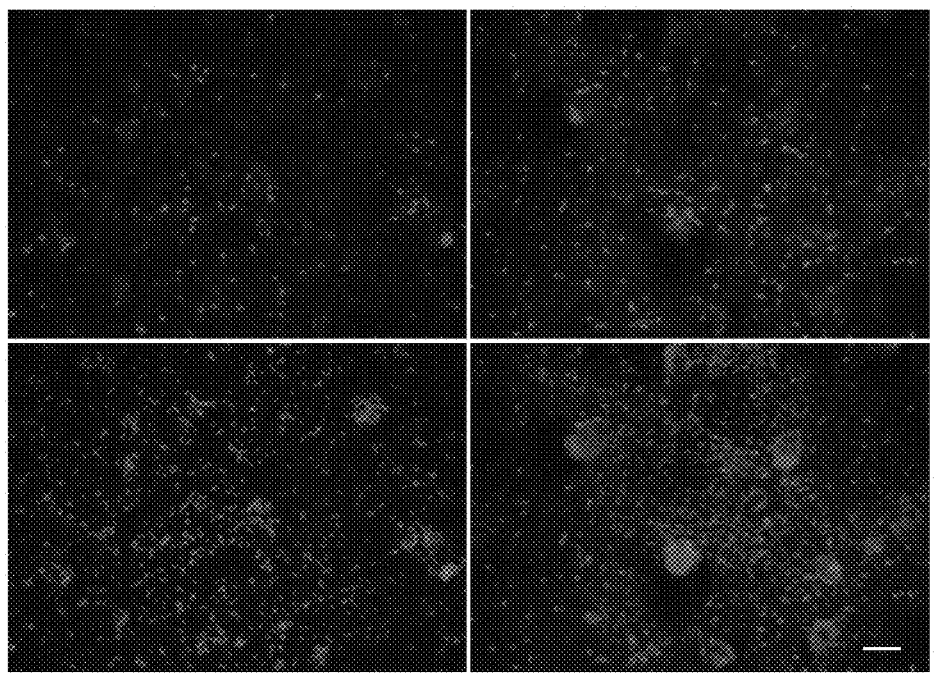

FIG. 7A showed the typical cell morphology on day 7. As shown in FIG. 7A, treatment with hPLT induced imDAP contraction obviously, which increased the difficulties for imDAP dissociation and collection after maturation, and imDAPs cultured with HhPLT and B27 appeared less compact, and obvious neural fibers were readily observed. Cells were counted and stained with TH (1° Ab: TH, Pel freez, #P40101. 2° Ab: Abcam, #ab130805) for flow cytometry analysis (FIG. 7B). As shown in FIG. 7B, compared to B27, the addition of hPLT greatly improved imDAP maturity (TH+ cell %), and the addition of HhPLT could further improve imDAP maturity (TH+ cell %) as compared with hPLT. Some cells were also plated on Laminin/poly-L-Ornithine (PLOH)-coated plates for 21-day additional maturation before staining with TH antibody (1° Ab: TH, Pel freez, #P40101. 2° Ab: Invitrogen, #A11012) for immunocytochemistry analysis (FIG. 7C). As shown in FIG. 7C, immunocytochemical analysis of TH in mDA neurons generated by using 1% HhPLT showed higher proportion of TH+ neurons compared to B27.

Example 12 WNT Inhibitor-Supplemented Medium LED to Higher Proportion of TH+ Neurons This example showed that IWR1 (a WNT inhibitor) could further improve the maturity for imDAPs.

imDAPs were produced according to the method described in CN201910169525.0, and expanded as described in Example 10. The expanded imDAPs were seeded on VTN-coated (1 μg/cm$^2$) plates at a density of 5×10$^5$ cells/cm$^2$ (Day 0), and cultured in the maturation medium supplemented with or without 1 μM IWR1. Medium was changed every $3^{rd}$ day. On day 7, the imDAPs at early maturation stage were dissociated enzymatically with 1× TrypLE, centrifuged at 250 g for 5 minutes. Cells were collected for RT-qPCR analysis of EN1, LMX1A, FOXA2, NURR1, SOX6 and TH gene expression. The maturation medium used in Example 12 contained the following components: Neurobasal™ medium, 1% (v/v) Glutamax, 1% (v/v) HhPLT, 0.5 mM Db-cAMP sodium salt, 200 μM ascorbic acid, 20 ng/mL BDNF, 20 ng/mL GDNF, 1 ng/mL TGF-03, 10 μM DAPT.

Figure 7D:
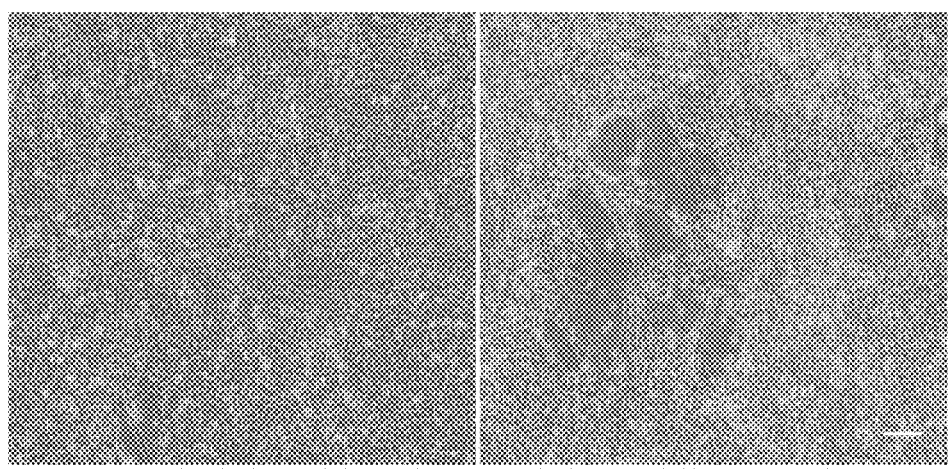
Figure 7E:
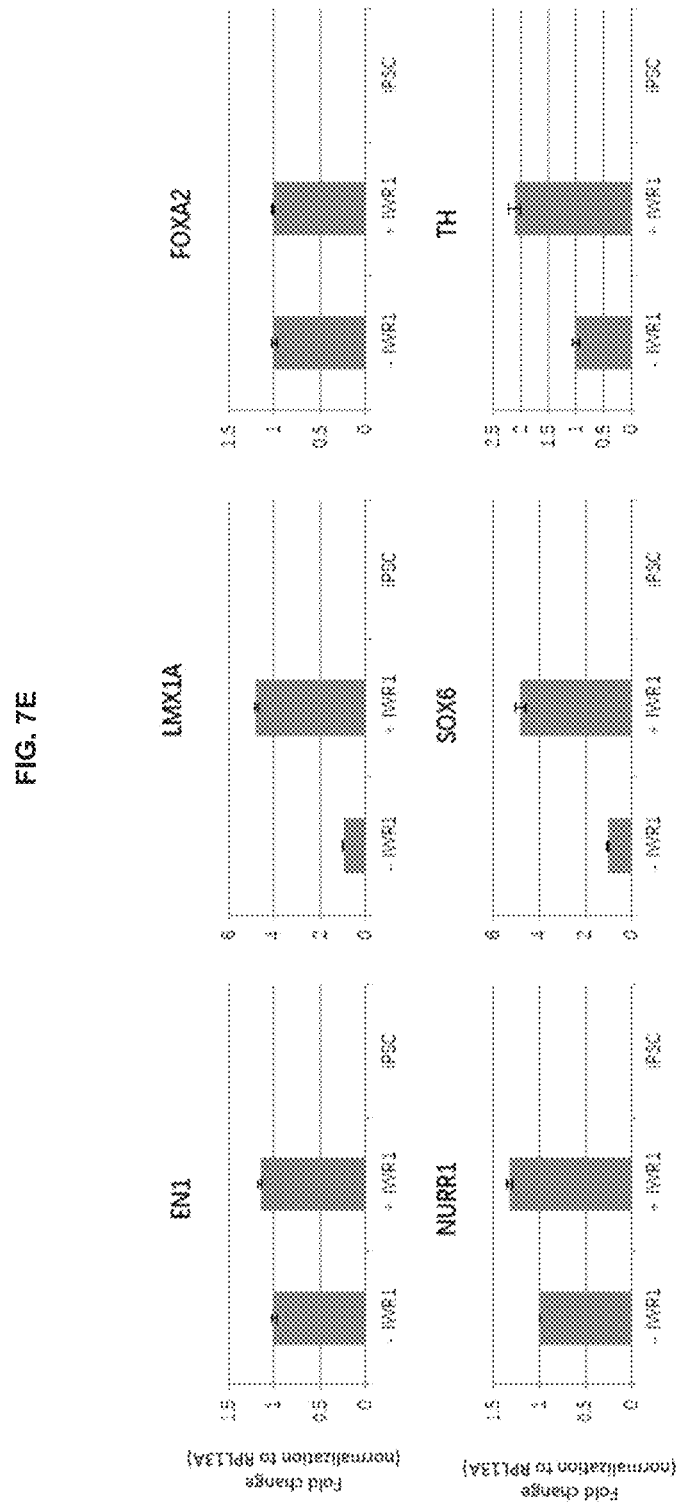

FIG. 7D showed the effect of IWR1 on cell morphology on day 7 during maturation. As shown in FIG. 7D, imDAPs matured in the presence of IWR1 for at least 3 days showed more obvious neural fibers. In addition, qRT-PCR analysis of mDA maturation associated markers such as NURR1, SOX6 and TH was performed (FIG. 7E). As shown in FIG. 7E, the expression of NURR1, SOX6 and TH were increased in cells treated with IWR1 compared to those without IWR1, which suggested better maturation.

Example 13 Use of a ROCK Inhibitor in Conjunction with Coating Matrix VTN/PLLH or VTN/PLOH Promoted imDAP Maturation Laminin/PLOH is commonly used as a matrix for mDA neuron maturation, but the cost is too high for large-scale mDA neuron production. In order to promote imDAP maturation while reducing cost, several different matrices were tested. This example showed that use of Y27632 (a ROCK inhibitor in the medium) in conjunction with coating matrix VTN/PLLH (Poly-L-Lysine hydrobromide) or VTN/PLOH (Poly-L-Ornithine hydrobromide) could promote imDAP maturation.

imDAPs were produced according to the method described in CN201910169525.0, and expanded as described in Example 10. The expanded imDAPs were seeded on different matrix-coated plates (VTN, VTN+PLLH, VTN+PLOH, and Laminin+PLOH) (1 μg/cm$^2$ for each) at a density of 5×10$^5$ cells/cm$^2$ (Day 0), and cultured in the maturation medium. In addition to inclusion of 10 μM or 0 μM Y27632, the maturation medium used in Example 13 further contained the following components: Neurobasal™ medium, 1% (v/v) Glutamax, 1% (v/v) HhPLT, 1 μM IWR1, 0.5 mM Db-cAMP sodium salt, 200 μM ascorbic acid, 20 ng/ml BDNF, 20 ng/ml GDNF, 1 ng/ml TGF-β 3, 10 μM DAPT. Medium was changed every $3^{rd}$ day. On day 3, IWR1 was removed from the maturation medium. On day 7, the imDAPs at early maturation stage were dissociated enzymatically with 1× TrypLE, centrifuged at 250 g for 5 minutes. Cells were collected and counted by Vi-cell cytometer. The cells were analyzed by RT-qPCR for EN1, LMX1A, FOXA2, NURR1, SOX6 and TH gene expression. And the cells also were seeded on coverslips in a 48-well plate at a density of 5×10$^4$ cells/cm$^2$ for immunostaining with LMX1A and SOX6 antibodies (LMX1A: Millipore, #MAB10533. SOX6: Proteintech, #14010-1-AP).

Figure 8B:
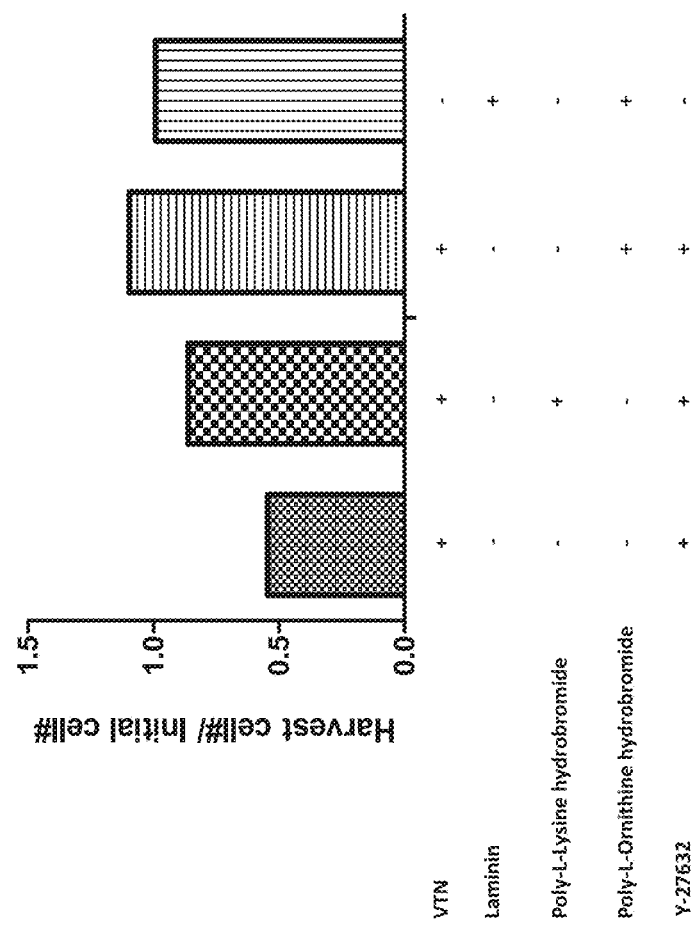
Figure 8C:
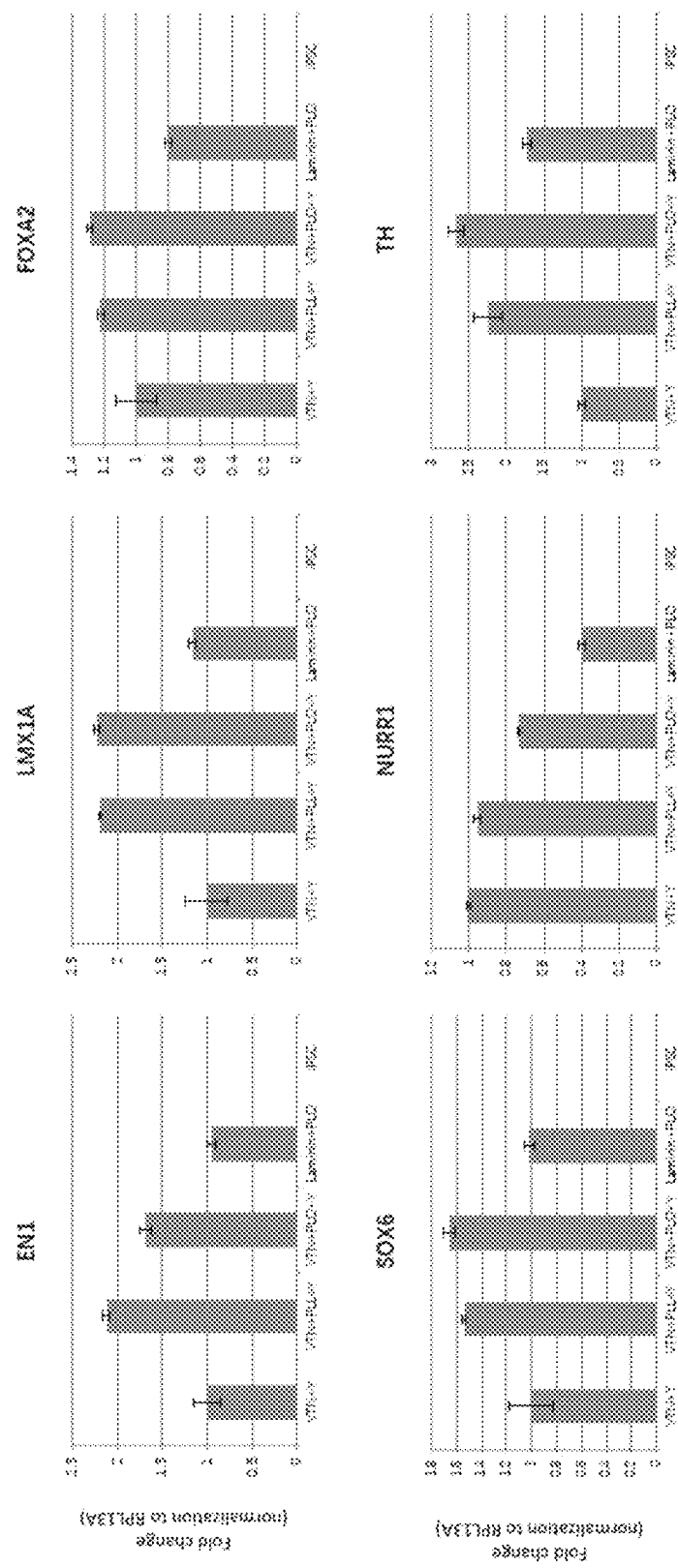

FIG. 8A showed the typical cell morphology on day 7 for the combinations of VTN+Y (control 1), VTN+PLLH (control 2), VTN+PLLH+Y, VTN+PLOH (control 3), VTN+PLOH+Y, and Laminin+PLOH (control 4). As shown in FIG. 8A, the cells plated on VTN/PLLH or VTN/PLOH were detached from the dishes in maturation media without Y27632. When the maturation media were supplemented with Y27632, the cells plated on VTN, VTN/PLLH or VTN/PLOH could grow normally, which suggested that Y27632 could promote cell adhesion at a certain degree. FIG. 8B showed the ratio of imDAP cell numbers following 7-day maturation compared to the input cell number. As shown in FIG. 8B, there was no significant difference in cell yield among the combinations VTN/PLLH+Y27632, VTN/PLOH+Y27632 and Laminin/PLOH, all of which were higher than the combination VTN+Y27632. FIG. 8C showed qRT-PCR analysis of mDA maturation associated markers following 7-day maturation. As shown in FIG. 8C, VTN/PLLH+Y27632 and VTN/PLOH+Y27632 outperformed Laminin/PLOH or VTN+Y in the gene expression of NURR1, SOX6 and TH at the early stage of maturation, which suggested that VTN/PLLH+Y27632 (or PLLH) as well as VTN/PLOH+Y27632 (or PLOH) could support better maturation.

Here, it was shown that use of Y27632 in the medium in conjunction with VTN/PLLH or VTN/PLOH was found to not only promote imDAP maturation, but also have a lower cost, and thus was more suitable for large-scale clinical production.

Example 14 Maturation Potential of imDAPs Cultured by Using a ROCK Inhibitor in Conjunction with Coating Matrix VTN/PLLH or VTN/PLOH at the Late Stage of Maturation This example showed that imDAPs cultured by using Y27632 in conjunction with VTN/PLLH or VTN/PLOH coated plate at the early stage of maturation had similar potential for terminal maturation.

The imDAPs following 7-day maturation in Example 13 were dissociated enzymatically with 1× TrypLE, centrifuged at 250 g for 5 minutes. Cells were collected and counted by Vi-cell cytometer. The cells were aggregated into 3D suspension culture (neurospheres) for further maturation. For this, the cells were resuspended at a density of $5 \times 10^5$ cells/mL and seeded into poly-HEMA coated (1 µg/cm$^2$) T25 flasks in 6 mL maturation medium-ND supplemented with 10 µM Y27632. To induce aggregation, T25 flask was plated on a Belly dancer at 15 rpm (Day 0). On day 1, the medium was changed with maturation medium-ND. The next day, half of the medium was replaced with maturation medium-BC. From day 3 onward, neurospheres were cultured in maturation medium-BC and the medium was changed every 3$^{rd}$ day. On day 21, the neurospheres were collected and fixed in 4% PFA in PBS for overnight at 4° C. followed by overnight incubation in 30% sucrose. Next, neurospheres were embedded in an OCT block and subjected to cryosectioning (20 µm) using a Cryostat. The cryosections of neurospheres were further immunostained with TH antibody (1° Ab: TH, Millipore, #MAB318. 2° Ab: Invitrogen, #A11029). The maturation medium-ND used in Example 14 contained the following components: Neurobasal™ medium, 1% (v/v) Glutamax, 1% HhPLT, 0.5 mM Db-cAMP sodium salt, 200 µM ascorbic acid, 20 ng/mL BDNF, 20 ng/mL GDNF, 1 ng/mL TGF-β 3, 10 µM DAPT. The maturation medium-BC used in Example 14 contained the following components: BrainPhys™ medium, 1% (v/v) Glutamax, 1% HhPLT, 0.5 mM Db-cAMP sodium salt, 200 µM ascorbic acid, 20 ng/mL BDNF, 20 ng/mL GDNF, 1 ng/mL TGF-β3, 1 µM Compound E (N—[N-(3,5-difluorophenacetyl)]-L-alanyl-3-(S)-amino-1-methyl-5-phenyl-1,3-dihydro-benzo[E](1,4)diazepin-2-one).

Figure 8D:
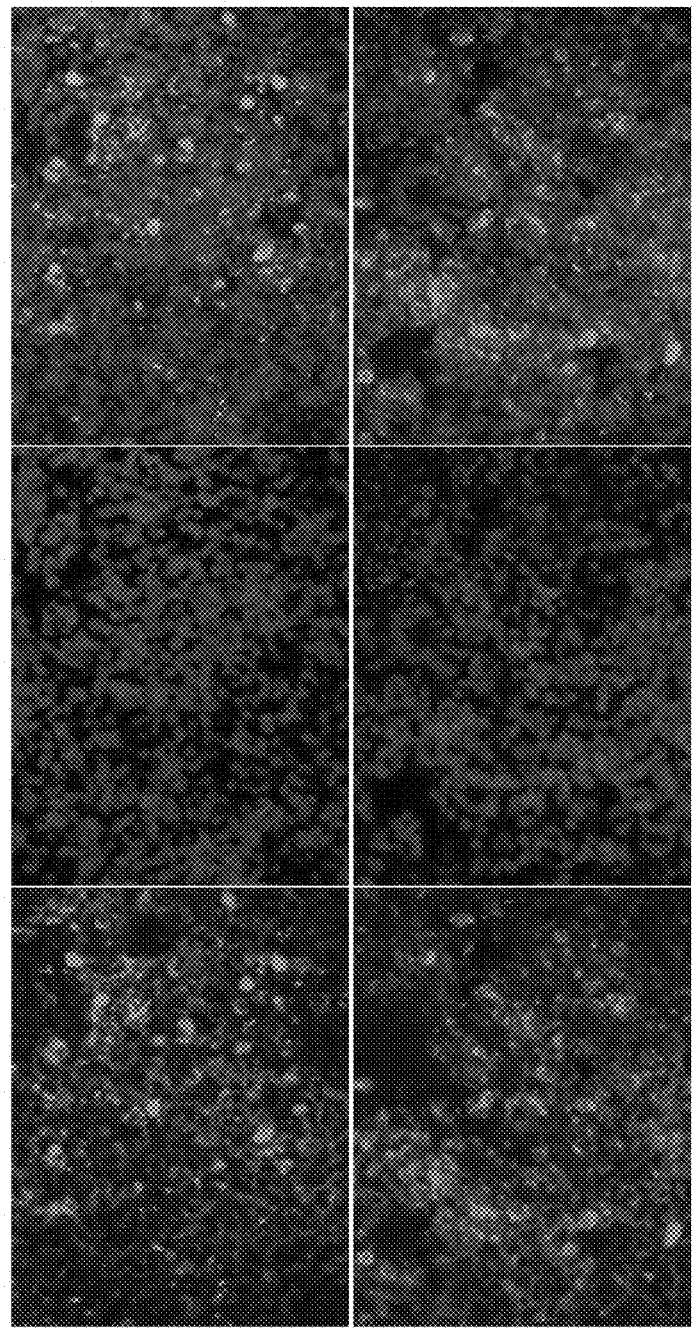
FIG. 8D shows the results of immunocytochemical analysis (Green light: TH; Blue light: DAPI (nucleus)) of the cryosections of neurospheres according to the Example 14 of the present disclosure (Scale bar: 20 μm).

FIG. 8D showed immunocytochemical analysis of the cryosections of neurospheres further matured from cells following 7-day maturation using Y27632 in conjunction with VTN/PLLH or VTN/PLOH. As shown in FIG. 8D, the imDAPs cultured by using Y27632 in conjunction with VTN/PLLH or VTN/PLOH at the early stage of maturation had the similar potential for terminal maturation.

Example 15 Expanded imDAPs at Early and Late Passage Maintained Similar High Capability to Differentiate into mDA Neurons at the Early-Stage Maturation This example showed that the expanded imDAPs at early and late passage could retain similar high ability to differentiate into mDA neurons at the early-stage maturation.

Figure 9C:
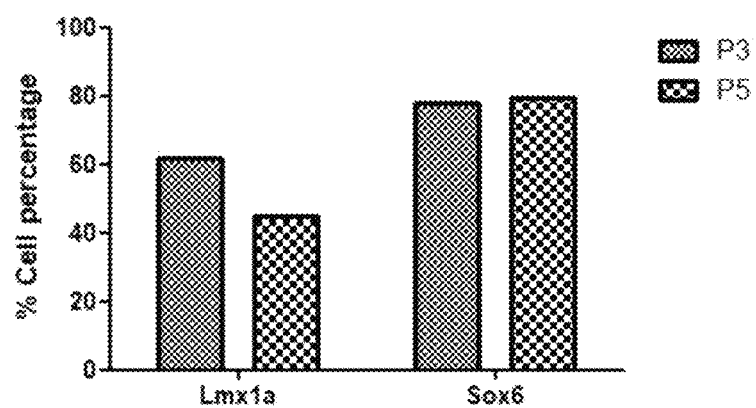
FIG. 9C shows the results of quantification of LMX1A- and SOX6-expressing mDA neurons matured from expanded P3 and P5 imDAPs.

Expanded P3, P5 and P6 imDAPs in Example 10 were seeded on VTN/PLOH coated (1 µg/cm$^2$ for each) plates at a density of $5 \times 10^5$ cells/cm$^2$ (Day0), and cultured in the maturation medium supplemented with 10 µM Y27632 and 1 µM IWR1. From day 3 onward, the above maturation medium was changed with the maturation medium supplemented with 10 µM Y27632 only. Changed the medium every 3$^{rd}$ day. On day 7, the imDAPs at early maturation stage were dissociated enzymatically with 1× TrypLE, centrifuged at 250 g for 5 minutes. Cells matured from expanded P3 and P6 imDAPs were collected and counted by Vi-cell cytometer. The cells were analyzed by RT-qPCR for EN1, LMX1A, FOXA2, NURR1, SOX6 and TH gene expression (FIG. 9A). And the cells matured from expanded P3 and P5 imDAPs also were seeded on coverslpis in a 48-well plate for immunostaining with LMX1A and SOX6 antibodies (LMX1A: Millipore, #MAB10533. SOX6: Proteintech, #14010-1-AP) (FIGS. 9B and 9C). The maturation medium used in Example 15 contained the following components: Neurobasal™ medium, 1% (v/v) Glutamax, 1% (v/v) HhPLT, 0.5 mM Db-cAMP sodium salt, 200 µM ascorbic acid, 20 ng/ml BDNF, 20 ng/ml GDNF, 1 ng/ml TGF-β3, 10 M DAPT.

FIG. 9A showed the results of RT-qPCR analysis of the expression of specific markers, EN1, LMX1A, FOXA2, NURR1, SOX6 and TH, in early-stage mDA neurons matured from expanded P3 and P6 imDAPs. The results showed no significant difference between the expanded P3 and P6 imDAPs. FIG. 9B showed the results of immunocytochemical analysis of the expression of LMX1A and SOX6 in early-stage mDA neurons matured from expanded P3 and P5 imDAPs. FIG. 9C showed the results of quantification of the LMX1A- and SOX6-expressing mDA neurons matured from P3 and P5 imDAPs at early maturation stage. The results showed no differences between the expanded P3 and P5 imDAPs. The results showed that the expanded imDAPs generated with this novel expansion method described herein could be passaged several times and also retain the high ability to differentiate into mDA neurons.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

What is claimed is:

1. A culture system comprising midbrain Dopaminergic Progenitor cells (mDAPs) and a cell culture substrate coated with a coating matrix combination that promotes the expansion of the mDAPs, wherein said coating matrix combination comprises:

(a) a first coating matrix that supports cell adhesion for the mDAPs, wherein the first coating matrix is selected from the group consisting of vitronectin (VTN), collagen, proteoglycan, fibronectin, entactin, elastin, laminin, a functional fragment of any preceding protein, hyaluronic acid, gelatin, and a combination thereof; and, (b) a second coating matrix that improves the expression of mDAP-specific markers during the expansion and passaging of the mDAPs as compared to that in the absence of the second coating matrix, wherein the second coating matrix comprises a Notch agonist.

2. The culture system of claim 1, wherein the first coating matrix is VTN.

3. The culture system of claim 1, wherein the Notch agonist is selected from the group consisting of Delta-Like 4 (DLL4), Delta-Like 1 (DLL1), Jagged-1, Jagged-2, a variant thereof, and a combination thereof.

4. The culture system of claim 1, wherein the coating matrix combination comprises VTN and DLL4.

5. The culture system of claim 1, wherein the culture system further comprises a culture medium.

6. The culture system of claim 5, wherein the culture medium comprises:
(a) a basal medium;
(b) a neural growth supplement;
(c) a WNT signaling pathway activator;
(d) a Rho Kinase (ROCK) inhibitor; and
(e) a Transforming Growth Factor β (TGF-β) inhibitor.

7. The culture system of claim 6, wherein the WNT signaling pathway activator is selected from the group consisting of Kenpaullone, 1-Azakenpaullone, CHIR99021, CHIR98014, NP031112, TWS119, AZD2858, AZD1080, SB415286, LY2090314, AR-A014418, SB216763, BIO (GSK 3 Inhibitor IX), BIO-Acetoxime, (5-Methyl-1H-pyrazol-3-yl)-(2-phenylquinazolin-4-yl)amine, 2-Thio(3-iodobenzyl)-5-(1-pyridyl) [1,3,4]-oxadiazole, alpha-4-Dibromoacetophenone, 3-(1-(3-Hydroxypropyl)-1H-pyrrolo[2,3-b]pyridin-3-yl]-4-pyrazin-2-yl-pyrrole-2,5-dione, 2-Chloro-1-(4,5-dibromo-thiophen-2-yl)-ethanone, RO318220, GF109203X and a combination thereof.

8. The culture system of claim 6, wherein the ROCK inhibitor is selected from the group consisting of Y27632, HA100, H1152, HA-1077, and a combination thereof.

9. The culture system of claim 6, wherein the TGF-β inhibitor is selected from the group consisting of RepSox, A83-01, SB431542, D4476, GW788388, LY364947, SB525334, SB505124, SD208, GW6604, and a combination thereof.

10. The culture system of claim 6, wherein the neural growth supplement is selected from the group consisting of B27, N1, N2, and a combination thereof.

11. The culture system of claim 6, wherein the WNT signaling pathway activator is present in the culture medium at a concentration of about 0.5 μM to about 20 μM.

12. The culture system of claim 6, wherein the ROCK inhibitor is present in the culture medium at a concentration of about 1 μM to about 50 μM.

13. The culture system of claim 6, wherein the TGF-β inhibitor is present in the culture medium at a concentration of about 0.5 μM to about 50 μM.

14. The culture system of claim 6, wherein the neural growth supplement is present in the culture medium at a concentration of about 0.1% to about 20% by volume.

15. The culture system of claim 6, wherein the culture medium comprises:
(a) about 1 μM to about 10 μM of the WNT signaling pathway activator;
(b) about 1 μM to about 20 UM of the ROCK inhibitor;
(c) about 1 μM to about 20 UM of the TGF-β inhibitor; and,
(d) about 0.1% to about 10% by volume of the neural growth supplement in the basal medium.

16. The culture system of claim 6, wherein the culture medium comprises:
(a) about 1 μM to about 10 μM of CHIR99021;
(b) about 1 μM to about 20 μM of Y27632;
(c) about 1 μM to about 20 M of SB431542; and,
(d) about 0.1% to about 10% by volume of B27 in the basal medium.

17. The culture system of claim 6, wherein the culture medium does not comprise FGF8 and/or FGF2.

18. The culture system of claim 6, wherein the culture medium further comprises a glutamine or its derivative, wherein the Glutamine or its derivative is present in the culture medium at a concentration of about 0.1% to about 5% by volume.

19. The culture system of claim 6, wherein the culture medium further comprises an antioxidant, wherein the antioxidant is present in the culture medium at a concentration of about 5 μg/mL to about 200 μg/mL.

20. The culture system of claim 6, wherein the culture medium is a chemically defined serum-free expansion medium.

21. The culture system of claim 1, wherein the mDAPs are iPSC-derived Midbrain Dopaminergic Progenitor cells (imDAPs).

* * * * *